(12) United States Patent
Von Segesser

(10) Patent No.: US 10,864,015 B2
(45) Date of Patent: Dec. 15, 2020

(54) FLOW AND DELIVERY APPARATUS

(71) Applicant: Coraflo Ltd., Lausanne (CH)

(72) Inventor: Ludwig K. Von Segesser, Lausanne (CH)

(73) Assignee: Coraflo Ltd., Lausanne (CH)

( * ) Notice: Subject to any disclaimer, the term of this patent is extended or adjusted under 35 U.S.C. 154(b) by 243 days.

(21) Appl. No.: 15/548,993

(22) PCT Filed: Feb. 5, 2016

(86) PCT No.: PCT/IB2016/000368
§ 371 (c)(1),
(2) Date: Aug. 4, 2017

(87) PCT Pub. No.: WO2016/128840
PCT Pub. Date: Aug. 18, 2016

(65) Prior Publication Data
US 2018/0243004 A1 Aug. 30, 2018

Related U.S. Application Data

(60) Provisional application No. 62/156,413, filed on May 4, 2015, provisional application No. 62/113,890, filed on Feb. 9, 2015.

(51) Int. Cl.
*A61B 17/34* (2006.01)
*A61M 1/36* (2006.01)
(Continued)

(52) U.S. Cl.
CPC ...... *A61B 17/3439* (2013.01); *A61B 17/3431* (2013.01); *A61M 1/3661* (2014.02);
(Continued)

(58) Field of Classification Search
CPC . A61M 1/3661; A61M 16/04; A61B 17/3439; A61B 17/3431; A61B 2017/3488; A61B 2017/3433
See application file for complete search history.

(56) References Cited

U.S. PATENT DOCUMENTS 5,819,733 A * 10/1998 Bertram ............... A61M 16/04
128/207.15
8,679,053 B2 * 3/2014 von Segesser ..... A61B 17/3439
604/104
(Continued)

OTHER PUBLICATIONS

International Search Report dated Jul. 18, 2016 for International Application No. PCT/IB2016/000368, filed Feb. 5, 2016.

*Primary Examiner* — Nathan R Price
*Assistant Examiner* — Anh Bui
(74) *Attorney, Agent, or Firm* — Mintz Levin Cohn Ferris Glovsky and Popeo, P.C.

(57) ABSTRACT

A cannula and a method of using a cannula are disclosed. The cannula include a first portion having an interior lumen, a narrow portion coupled to the first portion and having an interior lumen, an expandable portion having an interior lumen and being coupled to the narrow portion, and a tip being disposed at a distal end of the expandable portion. The expandable portion is being capable of having an expanded configuration and a collapsed configuration. The interior lumens of the first portion, the narrow portion, and the expandable portion are communicatively coupled to allow passage of at least one of a fluid, a powder, a gas, an object, and a device.

52 Claims, 45 Drawing Sheets

(51) Int. Cl.
*A61M 25/06* (2006.01)
*A61M 16/04* (2006.01)
*A61B 17/00* (2006.01)

(52) U.S. Cl.
CPC .............. *A61M 25/0662* (2013.01); *A61B 2017/00367* (2013.01); *A61B 2017/00557* (2013.01); *A61B 2017/3433* (2013.01); *A61B 2017/3488* (2013.01); *A61M 1/3659* (2014.02); *A61M 16/04* (2013.01)

(56) References Cited

U.S. PATENT DOCUMENTS

| | | | | |
|---|---|---|---|---|
| 2005/0038408 | A1* | 2/2005 | von Segesser | A61M 1/3661 604/506 |
| 2005/0192602 | A1* | 9/2005 | Manzo | A61B 17/11 606/153 |
| 2007/0233041 | A1* | 10/2007 | Gellman | A61B 17/3439 604/523 |
| 2010/0324607 | A1* | 12/2010 | Davis | A61B 17/8625 606/313 |

* cited by examiner

Conventional Cannula

Conventional Cannula

Conventional Cannula

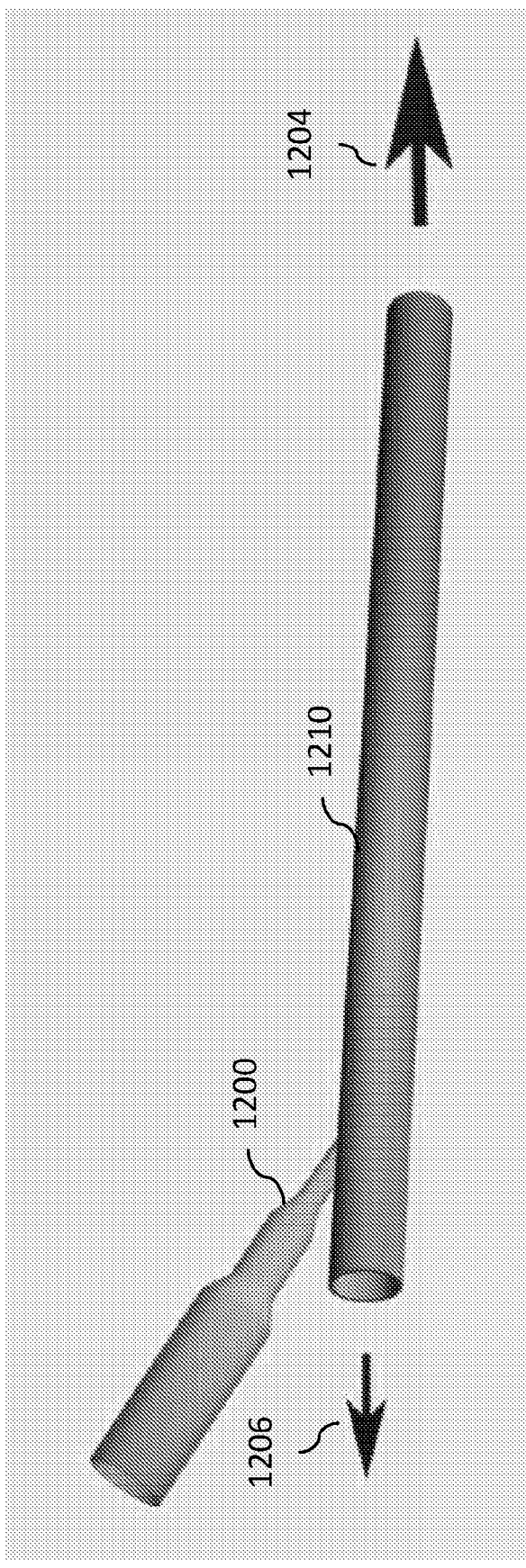
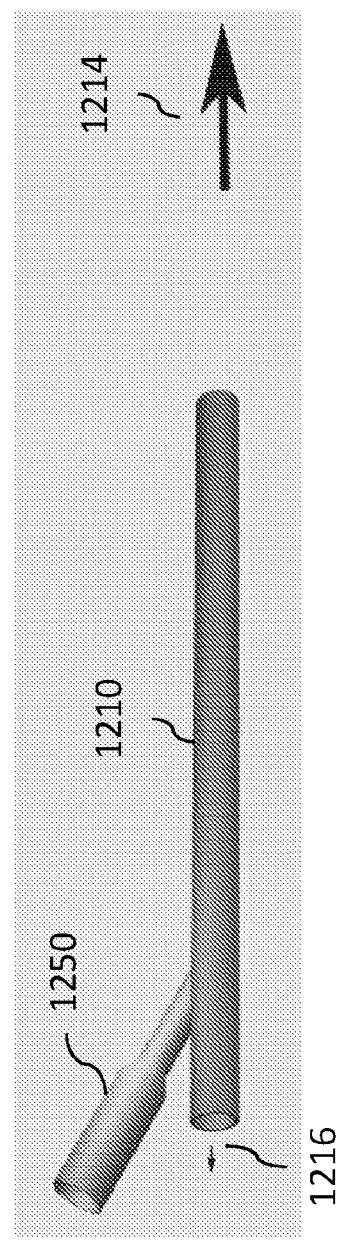
FIG. 12a.
FIG. 12b.

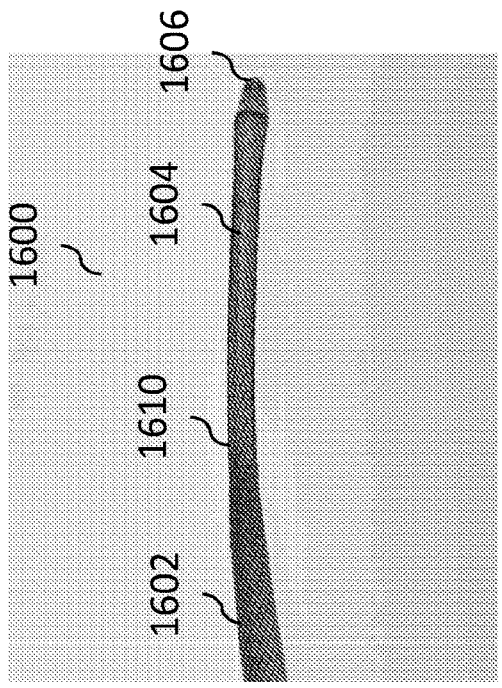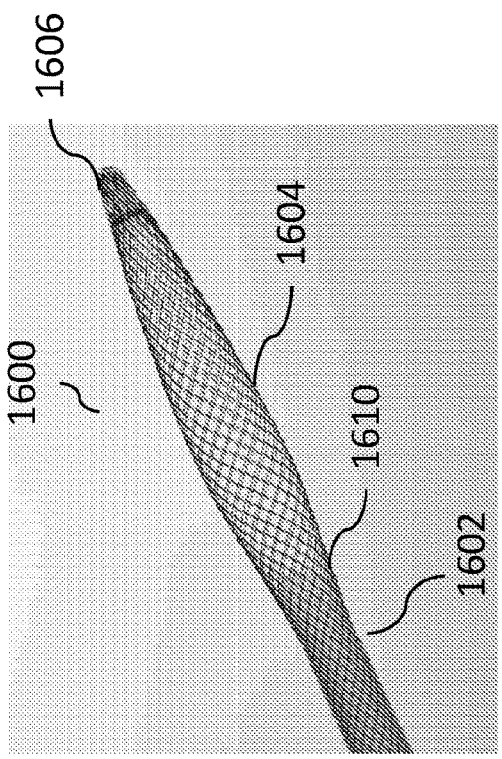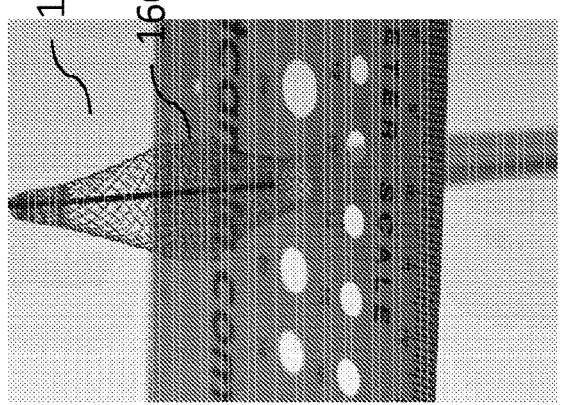

FLOW AND DELIVERY APPARATUS

CROSS-REFERENCE TO RELATED APPLICATIONS

The present application claims priority to and is a national stage entry, filed under 35 U.S. C. § 371, of International Application No. PCT/IB2016/000368, filed on Feb. 5, 2016, which claims priority to U.S. Provisional Patent Application No. 62/113,890 to von Segesser, filed Feb. 9, 2015, and entitled "Bidirectional Cannula", and to U.S. Provisional Patent Application No. 62/156,413 to von Segesser, filed May 4, 2015, and entitled "Locking Unidirectional and Bi-directional Cannulas," and incorporates their disclosures herein by reference in their entireties.

TECHNICAL FIELD

In some implementations, the current subject generally relates to a single/multiple flow and delivery apparatus and a method. More specifically, the current subject matter generally relates to cannulas, and in particular to bidirectional cannulas providing antegrade and/or retrograde flow. In some implementations, the current subject matter relates to locking unidirectional and/or bidirectional cannulas providing antegrade and/or retrograde flow(s). In some implementations, the current subject matter relates to a self-expandable sheath for delivery of objects, devices, fluids, etc.

BACKGROUND

Cannulation is essential for extra-corporeal circulation in order to drain blood towards the life support system prior to reinjection into the circulation. For high flow applications like cardio-pulmonary bypass, extra-corporeal membrane oxygenation etc., performance of a cannula can be very important, because it is usually the narrowest part in the perfusion circuit. Conventional cannula designs are typically based on rectilinear designs, i.e., straight tubes. Thus, the resistance of such cannulas is increasing with cannula length in linear fashion. Hence, shorter cannulas can offer better performance. However, with venous cannulas, the tip of the cannula has to be positioned in the right atrium in order to avoid cannula orifice obstruction, thereby creating additional complications.

As a result, two approaches have been developed to improve venous drainage. One approach relates to making the cannula wall thinner in order to get a larger cross sectional area and thus, providing less resistance. Another approach involves use of augmented venous drainage accomplished through a centrifugal pump or vacuum. However, increased suction resulted in cannula orifice obstruction 100, as shown in FIG. 1, which illustrates a percutaneous cannula being advanced into the right atrium for cardio-pulmonary bypass with remote venous cannulation. Increased suction on the venous line results in cannula orifice obstruction and shut off of venous drainage. This phenomenon is a typical finding in clinical cases undergoing minimal-invasive heart surgery with remote cannulation. The consequences of cannula orifice obstruction due to increased suction can also be demonstrated in vitro.

Thus, there is a need for an improved cannula design that can allow for an improved drainage of vessels. The improved design can have a unidirectional and/or bi-directional design allowing an antegrade and/or retrograde flow(s).

SUMMARY

In some implementations, the current subject matter relates to a cannula. The cannula can include an upper part for connection to a bypass tube, a segment (which can be narrow) connected to the upper part, and a lower part. The diameter of the segment can be smaller than the upper part, thereby facilitating insertion using a smaller diameter access point in a vessel. The segment can be inserted in a contracted state and can be capable of expanding subsequent to insertion. The upper part and the segment may (or may not) be covered with a thin water-tight coating. The segment can also be self-expanding and/or virtually wall-less. The upper part (or connecting part located outside of the body) and the segment can be covered whereas the lower or intravascular part may or may not be covered with a thin water-tight coating. This segment can also be self-expanding and/or virtually wall-less.

In some implementations, the current subject matter relates to a cannula that can provide a bidirectional flow and/or a unidirectional flow of fluids through a vessel. The cannula can include a locking mechanism that can be used to lock a configuration of the cannula in the vessel. The mechanism can be an active locking mechanism and/or a passive locking mechanism.

In some implementations, the current subject matter relates to an apparatus, such as a cannula. The apparatus can include a first portion having an interior lumen, a narrow portion coupled to the first portion and having an interior lumen, an expandable portion having an interior lumen and being coupled to the narrow portion, the expandable portion being capable of having an expanded configuration and a collapsed configuration, and a tip being disposed at a distal end of the expandable portion. The interior lumens of the first portion, the narrow portion, and the expandable portion are communicatively coupled to allow passage of at least one of a fluid, a gas, a powder, an object, and a device.

In some implementations, the current subject matter can include one or more of the following optional features. A diameter of the narrow portion can be smaller than a diameter of the first portion. The first portion can be configured to be connectable to bypass tubing. In the collapsed configuration, the narrow portion and the expandable portion can have substantially equal diameters. In the collapsed configuration, the expandable portion can be inserted through an access orifice having a diameter substantially equal to or greater than the diameter of the expandable portion in the collapsed configuration, the access orifice being disposed on a target object configured to receive the device. Upon insertion of the expandable portion through the access orifice, the expandable portion can be advanced to a target location in the target object, wherein, at the target location, the expandable portion can be expanded into the expandable configuration.

In some implementations, the tip can include at least one orifice. The expandable portion can include at least one orifice as well. The orifice in the expandable portion can be positioned proximate the tip.

In some implementations, the apparatus can include a coating for covering at least a part of at least one of the following: the narrow portion, the expandable portion, and the tip. The coating can be a watertight coating.

In some implementations, the apparatus can permit flow of fluid through interior lumens of at least one of the following: the first portion, the narrow portion, the expandable portion, and the tip. The flow of fluid can be in at least one of the following directions: a single direction and multiple directions. The flow of fluid can be in at least one of the following directions: a retrograde direction and an antegrade direction. The flow of fluid in the retrograde direction can be substantially equal and/or not equal to the flow of fluid in the antegrade direction.

In some implementations, the apparatus can be a cannula (a bidirectional use cannula and/or unidirectional use cannula). The cannula can be at least one of the following: an arterial cannula and a venous cannula.

In some implementations, the expandable portion can include at least one diffuser for directing flow of fluid out of the apparatus. The expandable portion can include at least one deflector for deflecting flow of fluid out of the apparatus.

In some implementations, at least one of the narrow portion, the expandable portion, and the tip can be self-expanding.

In some implementations, at least one of the narrow portion, the expandable portion, and the tip can include a plurality of flexible filaments allowing the diameters of the at least one of the narrow portion, the expandable portion, and the tip to be varied using at least one mechanism. At least one mechanism can, upon actuation, serve to alter the configuration of at least one of the narrow portion, the expandable portion, and the tip between the collapsed configuration and the expanded configuration. The plurality of flexible filaments can include one or more materials that include at least one of the following: metal, shape-memory metal, alloy, plastic, textile fiber, natural fiber, synthetic fiber, and/or any combinations thereof. The plurality of flexible filaments can have a shape including at least one of the following: round, oval, flattened, triangular, rectangular and/or any combinations thereof. The plurality of flexible filaments can include at least one of the following: elastic flexible filaments, non-elastic flexible filaments, textile fibers, flexible filaments that are braided together, flexible filaments that are knitted together, flexible filaments that are interwoven, flexible filaments that are interlaced, and/or any combination thereof. At least one flexible filament in the plurality of flexible filaments can be a covered flexible filament. At least one flexible filament in the plurality of flexible filaments can be an uncovered flexible filament. The mechanism can include at least one of the following: a mandrel, a bougie, a balloon, a pressurization mechanism, a retraction mechanism, an electric motor, a change in pressurization, a wrapping string, a tip capture device, a balloon and a sheath.

In some implementations, the cannula can be insertable into at least one of the following: a hollow body and a solid body. The hollow body can include at least one of the following: a hollow organ in a patient, a vein, an artery, a urethra, a ureter, an intestine, an esophagus, a trachea, a bronchial tube, a pleural space, a peritoneum, and a vessel within a solid organ in the patient and/or another access device. The plurality of flexible filaments can form a plurality of openings in the cannula, the at least one of the hollow body and the solid body can be configured to at least partially cover at least one opening in the plurality of openings when the cannula is inserted into the at least one of the hollow body and the solid body.

In some implementations, the cannula can be a wall-less cannula. The cannula can be configured to be used in at least one of the following: a medical context, a non-medical context, percutaneous insertion, central cannulation, a tracheal tube, a chest tube, a drainage catheter, a heart surgery, hemofiltration, hemodialysis, and a dialysis.

In some implementations, the tip can include at least one basket to stabilize placement of the tip at a target location. The basket can have a shape including at least one of the following: a bulb, a ball, a cylinder with round, an oval, an asymmetric shape, a triangular shape, a square shape, a pentagonal shape, a hexagonal shape, a heptagonal shape, an octagonal shape, a pyramid, a cone, a double cone, an inverted cone, an inverted double cone, a bell shape, a single layer shape, a dual layer shape, a multiple layer shape, single or multiple, uni- and/or multidirectional folds shape, plications, an inverted tulip-like structure, a tulip-like structure with a single or multiple small or large distal opening(s), a uniform shape, an asymmetric shape, and any combination thereof.

In some implementations, the expanded configuration can include at least one first expanded configuration and at least one second expanded configuration. A diameter of the expandable portion in the at least one second expanded configuration is greater than a diameter of the expandable portion in the at least one first configuration. In some implementation, this can allow for over-expansion of the cannula once the cannula is inserted beyond the access orifice. In some implementations, the expandable portion can include at least one portion having an elastic property to allow expansion of the expandable portion into at least one of the following: the at least one first expanded configuration and the at least one second expanded configuration. The expandable portion can also include at least one non-elastic section.

In some implementations, at least one of the expandable portion and the tip can include at least one portion containing at least one opening, wherein the at least one opening is configured for passing at least one of a fluid, a powder, a gas, an object, a device, and/or any combination thereof. That portion can be a non-elastic portion.

In some implementations, the expandable portion can be placed in the collapsed configuration using traction. The collapsed configuration can allow removal of the expandable portion from a target location.

In some implementations, the expandable portion can be placed in at least one of the collapsed configuration and the expanded configuration using at least one of the following mechanisms: a mandrel, a bougie, a balloon, a pressurization mechanism, a retraction mechanism, an electric motor, a change in pressurization, a wrapping string, a balloon, a sheath, and any combination thereof. The collapsed configuration can allow at least one of the placement and removal of at least the expandable portion from a target location.

In some implementations, the tip can include a basket having at least one expanded configuration and at least one collapsed configuration. The tip can be advanced to the target location in the collapsed configuration and expanded into the expandable configuration using the at least one of the mechanisms at the target location. Using at least one of the mechanisms, the tip can be placed into the collapsed configuration for removal from the target location. The basket can include at least one traction member for retaining the basket in the at least one expanded configuration. Release of the traction member can place the basket in the collapsed configuration.

In some implementations, the basket can include at least one locking mechanism (as discussed above) for retaining the basket in at least one expanded configuration, the locking mechanism is configured to stabilize the basket in the expanded configuration at the target location. The locking mechanism can include at least one of the following: an active locking mechanism, a passive locking mechanism, and any combination thereof. The locking mechanism can be configured to irreversibly retain the basket in the expanded configuration, thereby preventing the basket from being returned to the collapsed configuration. The locking mechanism can be configured to reversibly retain the basket in the expanded configuration, thereby allowing the basket to be returned into the collapsed configuration.

In some implementations, the apparatus can be a sheath. The sheath can be self-expandable. The sheath can be configured for delivery of at least one of the following: a fluid, a powder, a gas, an object, a device, and any combination thereof, to a target location. The sheath can include at least one of the following: at least one elastic section, at least one non-elastic section, at least one permanently deformable section, at least one temporarily deformable section, and/or any combination thereof. The sheath can include at least one lumen. The lumen can allow passage of at least one of the following: a fluid, a powder, a gas, an object, a device, and any combination thereof. The lumen in the sheath can include at least one of the following: a pressurized lumen, a depressurized lumen, a valve, a side arm, a split and any combination thereof.

In some implementations, the sheath can include a coating covering at least one portion of the sheath. The coating can be configured to change at least one property of the sheath including at least one of the following: a physical property, a chemical property, a mechanical property, a pharmaceutical property and any combination thereof.

In some implementations, the current subject matter relates to a cannula. The cannula can include a cannula housing having at least one lumen and at least one expandable portion. The expandable portion can have at least one expanded configuration and at least one collapsed configuration. A diameter of the lumen in the expanded configuration is greater than a diameter of the lumen in the collapsed configuration. In the expanded configuration, the lumen can allow passage of at least one of a fluid, a powder, a gas, an object, a device and any combination thereof. The expandable portion can be a self-expandable portion. The cannula housing can include a plurality of lumens. The cannula housing can include at least one orifice. The cannula housing can include at least one self-expanding tip.

In some implementations, the current subject matter relates to a sheath. The sheath can include a sheath housing having at least one lumen and at least one expandable portion. The expandable portion can have at least one expanded configuration and at least one collapsed configuration. A diameter of the lumen in the expanded configuration is greater than a diameter of the lumen in the collapsed configuration. In the expanded configuration, the lumen can allow passage of at least one of a fluid, a powder, a gas, an object, a device and any combination thereof. The expandable portion can be a self-expandable portion. The sheath housing can include a plurality of lumens. The sheath housing can include at least one orifice. The sheath housing can include at least one self-expanding tip.

In some implementations, the current subject matter relates to a method for using the above apparatus. The method can include placing the expandable portion in the collapsed configuration, inserting the expandable portion at a point of insertion on a body, and expanding the expandable portion into the expanded configuration, wherein in the expanded configuration, the expandable portion expands up to at least one of the following: a surface of an interior wall of the body, the surrounding environment and the maximum diameter of the at least one lumen.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

FIG. 12a illustrates an exemplary arterial bidirectional cannula, according to some implementations of the current subject matter;

FIG. 12b illustrates a conventional arterial cannula;

FIGS. 16a-e illustrate use of an exemplary bidirectional flow cannula, according to some implementations of the current subject matter;

DETAILED DESCRIPTION

To address deficiencies of some of the existing cannula designs, some exemplary implementations of the current subject matter provide for an improved cannula design that can allow for bidirectional flow, i.e., antegrade and/or retrograde flow(s). In some implementations, the current subject matter relates to locking unidirectional and/or bidirectional cannulas providing antegrade and/or retrograde flow(s). In some implementations, the current subject matter relates to cannula locking mechanism. In some implementations, the current subject matter relates to self-expandable sheaths.

I. Bidirectional Cannula

In some implementations, the current subject matter relates to an optionally self-expanding, optionally virtually wall-less cannula having a short (e.g., few millimeters to few centimeters long) narrow segment (which can be covered and/or can be self-expanding, in such a way, that the cannula does not completely fill an access vessel at the point of insertion. The cannula can provide a bi-directional flow of fluids in a vessel.

Figure 1:
FIG. 1 illustrates a conventional percutaneous cannula being advanced into the right atrium for cardio-pulmonary bypass with remote venous cannulation.
Figure 2:
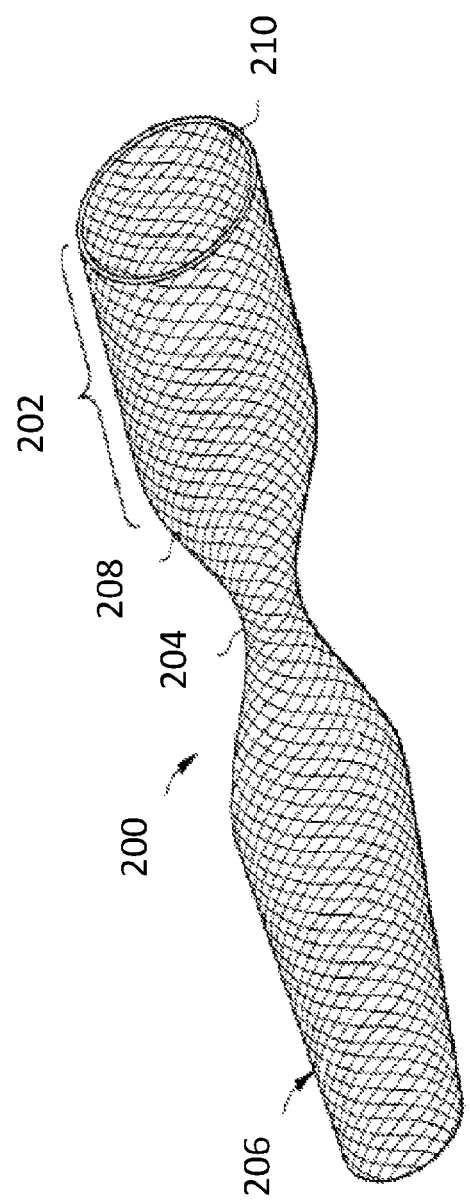
FIG. 2 illustrates a self-expanding cannula.

An exemplary self-expanding cannula is disclosed in the co-owned U.S. Pat. No. 8,992,455 to von Segesser, issued on Mar. 31, 2015, and entitled "Methods, apparatuses and systems for caval stenting for venous drainage," and co-owned U.S. Pat. No. 8,679,053 to von Segesser, issued Mar. 25, 2014, and entitled "High performance cannulas," the disclosures of which are reiterated and incorporated herein by reference in their entireties. An exemplary self-expanding cannula 200 is shown in FIG. 2. The cannula 200 can allow for superior performance on both, the venous and/or the arterial, sides due to the increased cross-sectional area of the cannula body and absence of flow restricting orifices.

In some implementations, the self-expanding cannula 200 can have virtually no wall (e.g., wall-less), as it can be a supporting structure, where the seal can be provided by the cannulated vessel itself. The cannula 200 can include a cannula body 208 having a proximal end 202 having a diameter 210 and a distal end 206. A point of insertion 204 can be disposed between the proximal end 202 and the distal end 206. The end 202 can be disposed outside of a vessel connecting to a venous line at the tip 210. The portion 204 can be within the vessel access orifice. The portion 204 can expand automatically to the access vessel's diameter (e.g., 8 mm for a vein and 7 mm for an artery). Portion 206 can be an intra-venous part, which can expand up to the vessel's diameter (e.g., 24 French ("F") for a vein and 21 F for an artery). The virtually wall-less and self-expanding cannula 200 provides numerous advantages over the conventional designs, some of which are discussed below with reference to FIGS. 3a-5f.

A. Conventional Cannulas

FIGS. 3a-5f illustrate various existing cannulas along with their corresponding structural parameters and/or sizes.

Figure 3A:
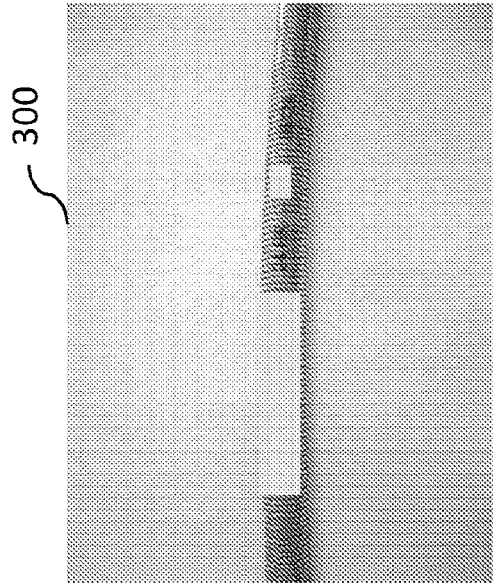
FIGS. 3a-d illustrate conventional rectilinear wire wound cannulas.
Figure 3B:
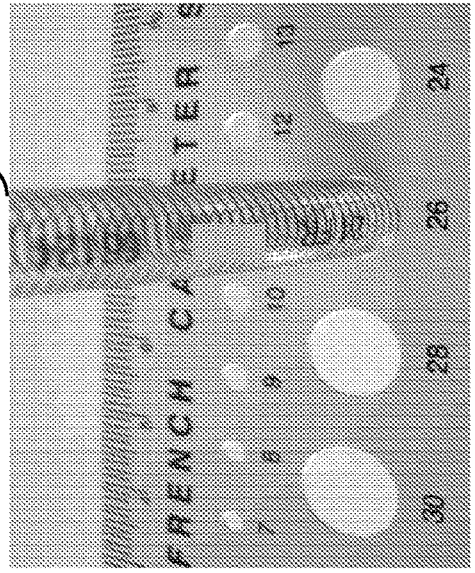
Figure 3C:
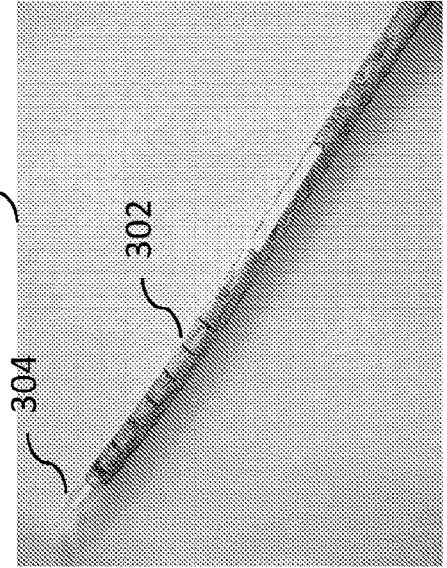
Figure 3D:
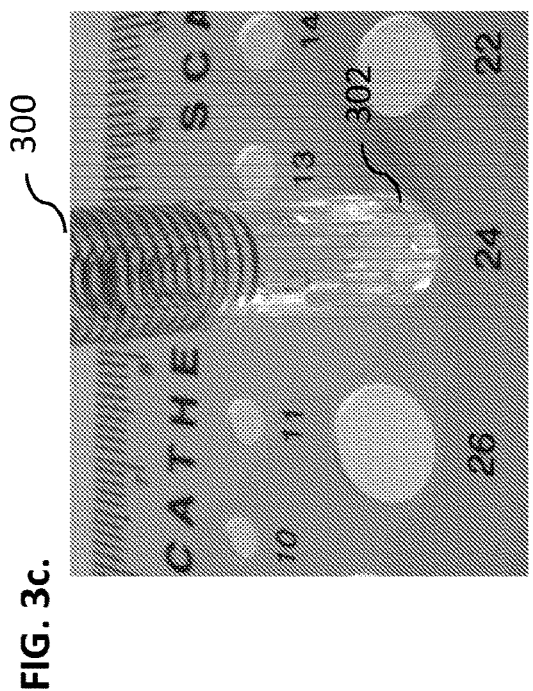

In particular, FIGS. 3a-d illustrate conventional rectilinear wire wound cannulas. As shown in FIG. 3a, the cannula 300 can include a wire 302 wound and embedded within the cannula body, where the cannula has a lighthouse tip 304. The cannula 300 has a 24 F diameter. FIG. 3b illustrates the conventional 24 F cannula 300, where the cannula has a wall thickness of slightly less than 1 millimeter ("mm"). In conventional practice, peripheral cannulation procedures can be performed using cannula 300 (as shown in FIGS. 3a and 3b). FIG. 3c illustrates that the conventional cannula 300 is unable to pass through a 24 F orifice, which can be a typical problem with various conventional cannulas. FIG. 3d illustrates that the actual diameter of the 24 F conventional cannula 300 is approximately 26 F, thus, the cannula 300 will not be able to pass through a 24 F vessel. It is likely that in order to pass through a 24 F vessel, the conventional cannula size would have to be approximately 22 F. This can severely reduce effectiveness of the cannula by reducing the amount flow that can pass through the cannula, thereby rendering the cannula substantially ineffective.

Figure 4B:
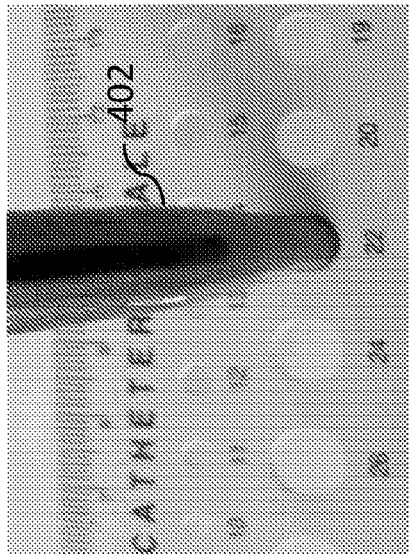
FIGS. 4a-c illustrate conventional percutaneous cannulas.
Figure 4A:
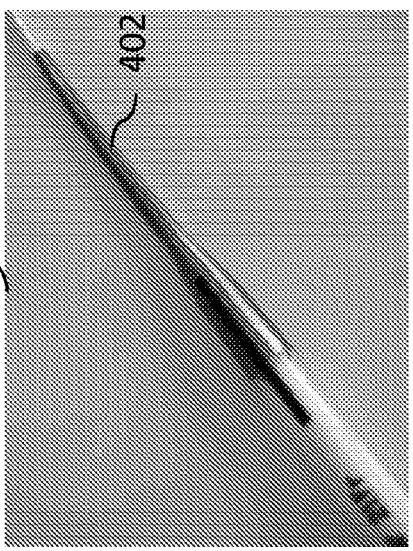
Figure 4C:
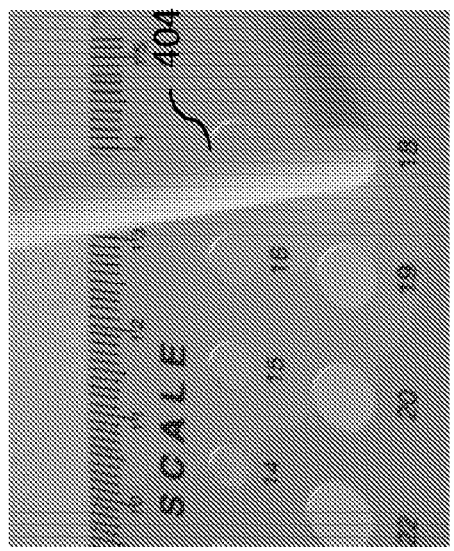

FIGS. 4a-c illustrate conventional percutaneous cannulas. Such cannulas are typically used for minimally-invasive surgery, where remote venous and arterial cannulation using such percutaneous cannulas is a preferred approach. As shown in FIG. 4a, the conventional cannula 400 includes a flat wire 402 wound and/or imbedded within the cannula body having a wall thickness of approximately 1 mm. The conventional percutaneous cannula 400, shown in FIG. 4a, has a diameter of 21 F. As shown in FIG. 4b, the actual size of the conventional percutaneous 21 F cannula 400 is 22 F. Thus, the cannula 400 would not be able to pass through a 20 F orifice. FIG. 4c illustrates a mandrel 404 of the 21 F percutaneous cannula 400 shown in FIG. 4a. The mandrel can pass through an 18 F orifice. Hence, the wall thickness of the cannula 400 is slightly less than 1 mm.

FIGS. 5a-5f illustrate various existing self-expanding cannulas. Exemplary self-expanding cannulas are disclosed in co-owned U.S. Pat. No. 8,992,455 to von Segesser, issued on Mar. 31, 2015, and entitled "Methods, apparatuses and systems for caval stenting for venous drainage," and co-owned U.S. Pat. No. 8,679,053 to von Segesser, issued Mar. 25, 2014, and entitled "High performance cannulas," the disclosures of which are reiterated and incorporated herein by reference in their entireties.

Figure 5C:
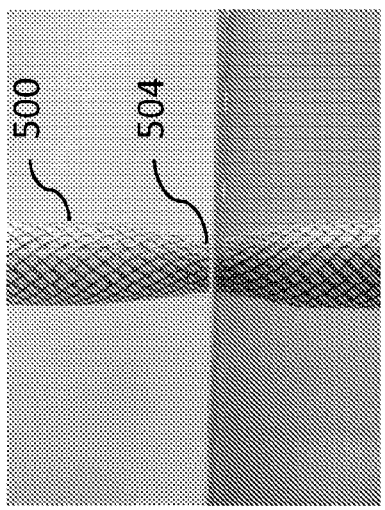
FIGS. 5a-5f illustrate various existing self-expanding cannulas.
Figure 5B:
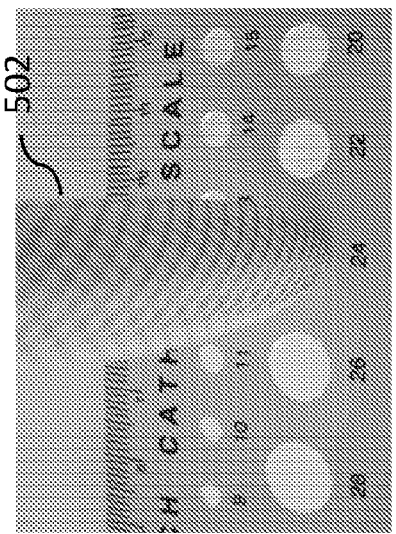
Figure 5A:
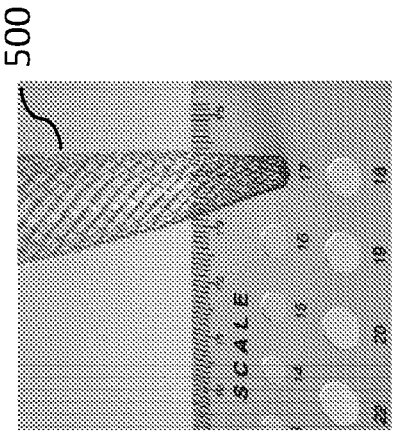
Figure 5F:
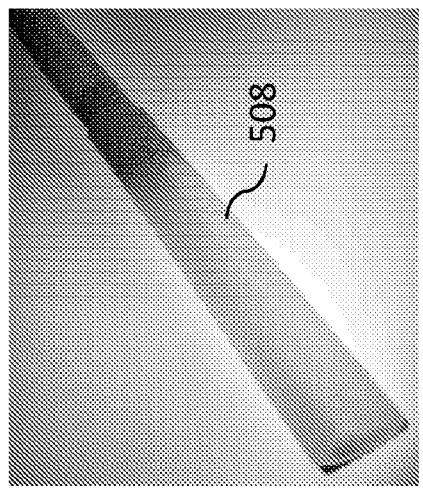
Figure 5E:
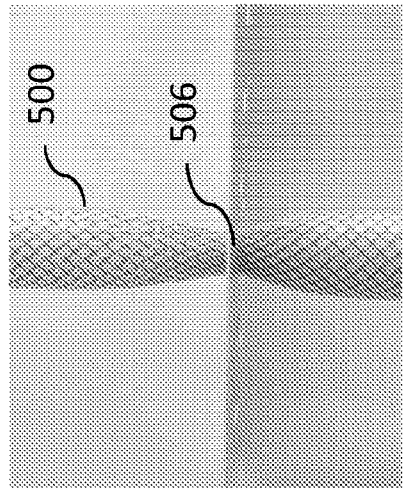
Figure 5D:
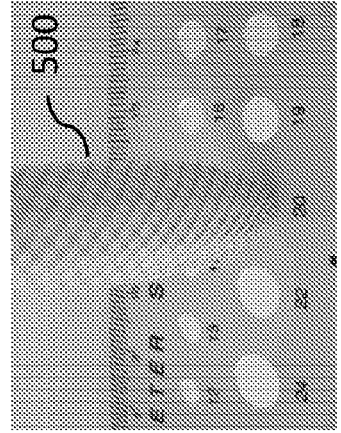

FIG. 5a illustrates an exemplary cannula 500 having a tip of approximately 36 F in diameter. As disclosed in the above co-owned patents, the cannula 500 can be placed in a normal or expanded configuration and a collapsed configuration. The collapsed configuration can be used for placement of the cannula into a vessel. The normal or expanded configuration can be used while the cannula is inside the vessel and expansion of the cannula is desired for the purposes of providing flow of fluids (e.g., blood). In view of the self-expandable abilities of the cannula 500, the cannula 500 can be capable of passing through a 17 F orifice, as indicated by the measuring ruler in FIG. 5a. FIG. 5b illustrates a body 502 of the 36 F self-expanding cannula 500 shown in FIG. 5a. The body 502 of the cannula 500 can pass through a 24 F orifice, as shown by the measuring ruler in FIG. 5b. FIG. 5c illustrates the 36 F self-expanding cannula 500 having a waist 504, which can be created upon passing of the cannula 500 through an access orifice. As shown in FIG. 5c, the orifice has a 24 F diameter, indicating that at the waist 504, the cannula 500 can be collapsed. In view of the self-expanding capabilities of the cannula 500, it is capable of passing through smaller orifices. FIG. 5d illustrates the exemplary 36 F self-expanding cannula 500 passing through a 20 F access orifice, as indicated by the ruler in FIG. 5d. Since the cannula 500 has passed through a smaller access orifice, its waist 508 (as shown in FIG. 5e) is smaller waist 506 (as shown in FIG. 5c). FIG. 5f illustrates that all attachments 508 (e.g., expansion mechanisms, etc.) that may be required for connection of the self-expanding cannula 500 can be located outside of the vessel, where space may not be an issue.

B. Bidirectional Cannulas

As stated above, conventional rectilinear cannulas used for peripheral cannulation can usually require a full cross-sectional area of the access vessel at the point of insertion. This can cause lack of performance associated with these cannulas and has severe drawbacks, including, absence of perfusion of the distal part of the access vessel, if the vessel is an artery (which can result in a moderate to absolute leg ischemia for cannulation of the femoral artery causing an irreversible damage and subsequent amputation in some cases), and/or absence of drainage of the distal part of the access vessel, if the vessel is a vein (which can result in some degree of venous stasis which may lead to deep vein thrombosis and further complications).

In some implementations, the current subject matter relates to a cannula, which can be a peripheral cannula. The cannula can be also self-expanding and/or virtually wall-less. In some implementations, the cannula can include a plurality of flexible filaments allowing the diameters of the at least one portion of the cannula to be varied (e.g., expanded, over-expanded, collapsed, etc.). The variation of the diameters can be accomplished using at least one mechanism. The mechanism can include at least one of the following: a mandrel, a bougie, a balloon, a pressurization mechanism, a retraction mechanism, an electric motor, a change in pressurization, a wrapping string, a balloon, a sheath and/or any combination thereof. The flexible filaments can be manufactured from one or more materials that include at least one of the following: metal, shape-memory metal, alloy, plastic, textile fiber, synthetic fiber, natural fiber, and combinations thereof. The filaments can be flexible, elastic, non-elastic, rigid, semi-rigid, and/or any combination thereof. The filaments can have a shape including at least one of the following: round, oval, flattened, triangular, rectangular and/or any combination thereof. In some implementations, the filaments can include at least one of the following: an elastic flexible filament, a non-elastic flexible filament, a textile fiber, flexible filaments that are braided together, flexible filaments that are knitted together, flexible filaments that are interwoven, flexible filaments that are interlaced, and any combination thereof. In some implementations, at least one flexible filament can be covered and/or uncovered. Further, the flexible filaments form a plurality of openings in the cannula. Once the cannula inserted into a target location (e.g., a hollow body, a solid body, a vessel, a lumen, a tube, etc.), the wall structure of the target location can partially and/or fully cover one or more openings.

In some implementations, the cannula can be inserted into a hollow body, a solid body, and/or any combination thereof. The hollow body can include at least one of the following: a hollow organ in a patient, a vein, an artery, a urethra, a ureter, an intestine, an esophagus, a trachea, a bronchial tube, a pleural space, a peritoneum, and a vessel within a solid organ in the patient and/or another access device. The solid body can be any organ in a body (e.g., of a patient, animal, etc.).

In some implementations, the cannula can include a short (e.g., a few millimeters to a few centimeters long) narrow covered segment. In some exemplary implementations, for open cannulation (e.g., direct cannulation of the access vessel), the exemplary length of the short narrow segment can be 30±10 mm. For percutaneous cannulation with an 80 mm hollow needle, the exemplary length of the short narrow segment can be 100±10 mm. This can ensure that a section of the short narrow segment can be positioned within an access vessel in order to provide a seal. The segment can be self-expanding. The cannula can be so designed that it does not completely fill an access vessel at the point of insertion. The current subject matter's cannula, along with an optional self-expanding design and/or optional virtually wall-less configuration, can provide a superior performance, e.g., unidirectional flow, bidirectional flow, increased flow, etc.

Figure 6B:
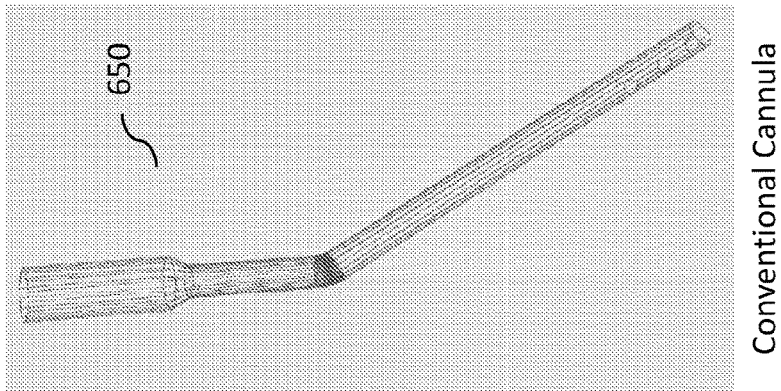
FIGS. 6b and 6d illustrate conventional cannulas.
Figure 6A:
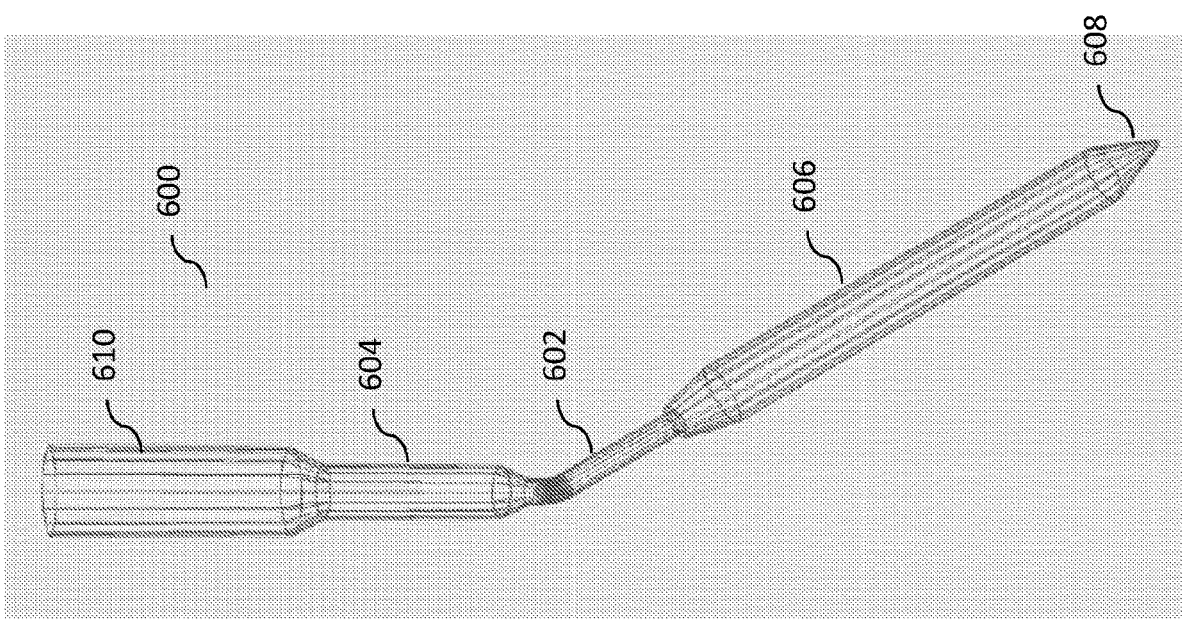
FIGS. 6a and 6c illustrate exemplary cannulas, according to some implementations of the current subject matter.

FIG. 6a illustrates an exemplary cannula 600, according to some implementations of the current subject matter. By contrast, FIG. 6b illustrates a conventional rectilinear cannula 650, which can be used for percutaneous insertion. The cannula 600 can be self-expanding, virtually wall-less bidirectional cannula. The cannula can be used for insertion into a target or access vessel (not shown in FIG. 6a). The cannula 600 can include a narrow segment 602, an upper portion 604, and a lower portion 606. At its proximate end, the narrow segment 602 can be coupled to the upper portion 604 and, at its distal end, the narrow segment 602 can be coupled to the lower portion 606. The diameter of the narrow segment 602 can be smaller than the upper portion 604 and smaller than the diameter of the lower portion 606 when the lower portion 606 is in an expanded state, as shown in FIG. 6a. The lower portion 606 can also include a distal tip 608, which can be used for entry into the target vessel. The upper portion 604 of the cannula 600 can be designed for connection to the bypass tubing 610. The lower portion 606 of the cannula 600 is capable of contracting and expanding and, thereby can achieve diameter that is larger than the diameter of the narrow segment 602 and/or the diameter of the upper portion 604. In some exemplary non-limiting and illustrative implementations having a cannula with a collapsed tip of 18 F, the diameter can expand from approximately 24 F to approximately 45 F. In some exemplary non-limiting and illustrative implementations having a cannula with a collapsed tip of 12 F, the diameter can expand between approximately 16 F and approximately 24 F. In some exemplary non-limiting and illustrative implementations having a cannula with a collapsed tip of 6 F, the diameter can expand between approximately 10 F to approximately 16 F. Other exemplary implementations are possible. The narrow segment 602 can also be collapsed prior to insertion, and re-expanded in situ, in order to minimize its diameter prior to entry into the target vessel. In some implementations, the upper portion 604 and the narrow segment 602 can be covered with a thin water-tight coating. The coating can include at least one of the following: elastic plastics, polyurethane, silicone, rubber, synthetic rubber, Lycra, PET, thin film, a woven cloth, knitted tube, etc. and/or any combination thereof. The lower portion 606 can be positioned within the target vessel and can be un-coated and/or virtually wall-less. In some implementations, the cannula 600 can allow a flow of fluids in any direction (e.g., antegrade, retrograde, and/or both).

In some implementations, the upper portion 604 can be a connector to the bypass tubing and/or other attachments. It can be located outside of the target vessel and can have any dimension that may be needed to provide sufficient flow.

Figure 6D:
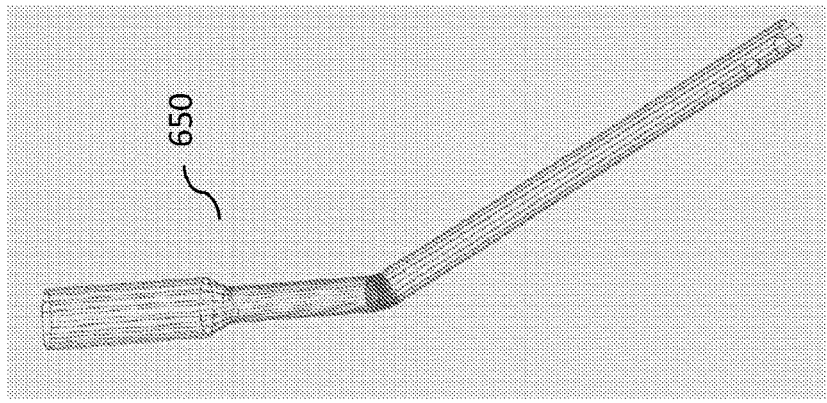
Figure 6C:
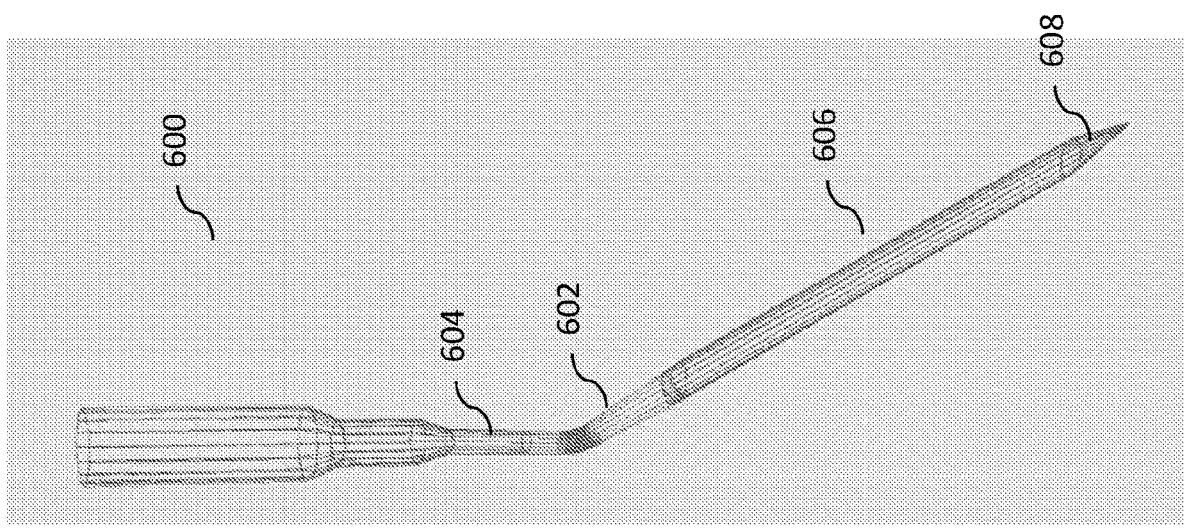

In some implementations, in order to insert the cannula 600 into the target vessel, the lower portion 606 and/or the narrow segment 602 can be collapsed to their respective smallest possible diameters (and/or any other desired diameters). FIG. 6c illustrates cannula 600 having the lower portion 606 and/or segment 602 in a collapsed configuration (FIG. 6d illustrates the conventional cannula 650, which is unable to achieve a similar collapsed configuration). Then, the cannula 600 can be advanced through an access orifice (not shown in FIG. 6a) that may be created in a wall of the target vessel (and/or any other access vessel that may be connected to the target vessel). The narrow segment 602 can be advanced through the vessel wall bud might not completely fill the interior of the access vessel in order to allow for flow through it in one direction and parallel to it in the other direction. Once the lower portion 606 is inserted into the target vessel (which can be confirmed through, for example, x-ray, and/or any other scanning or imaging technology, and/or upon receiving an indication from a sensor that can be disposed on the cannula), the lower portion 606 can be expanded up to a desired size (e.g., the surface of an interior wall of the target vessel). The cannula can be inserted over a guidewire and can be contracted (and/or stretched) and/or collapsed using a mandrel, a bougie, a balloon, a pressurization mechanism, a retraction mechanism, and/or any other suitable device. The expandable portion 606 and/or the entire cannula and/or any component thereof can have any desired size, shape, curvature, length, flexibility, etc.

In some exemplary implementations, the cannula 600 can have a diabolo shape (short narrow part within the access orifice and/or the access vessel), and/or any other desired shape. Further, the cannula 600 can have a self-expanding design, which can provide a performance increase, which can compensate for a possible decrease in fluid pressure because of existence of the narrow segment 602.

In some implementations, the cannula 600 can be used as an arterial cannula and/or as a venous cannula. The arterial cannula 600 can be inserted into the femoral artery from the groin towards the aorta. Conventional arterial cannulas allow retrograde flow (i.e., the direction of the natural blood flow) but not much antegrade perfusion towards a limb. By contrast, the arterial cannula 600 can allow for a bidirectional flow, which can allow for perfusion in both directions: a retrograde towards an aorta and an antegrade towards a limb. With reference to the antegrade flow within the arterial cannula coming from the pump-oxygenator, the perfusion of the limb can be retrograde.

The venous cannula 600 can be inserted into the femoral vein from the groin towards the vena cava and the right atrium. Conventional venous cannulas allow retrograde flow (i.e., the direction of the natural flow), but not much antegrade drainage from the limb. The venous cannula 600 can allow drainage in both directions: retrograde from the vena cava and antegrade from the limb. With reference to the retrograde flow within the venous cannula 600 (towards the pump), the drainage from the limb can be antegrade.

Figure 7B:
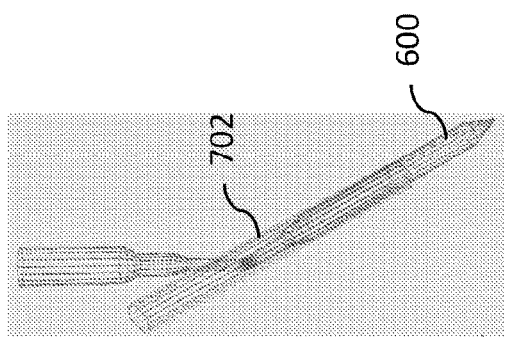
FIGS. 7a-b illustrate an exemplary cannula being inserted into a vessel, according to some implementations of the current subject matter.
Figure 7A:
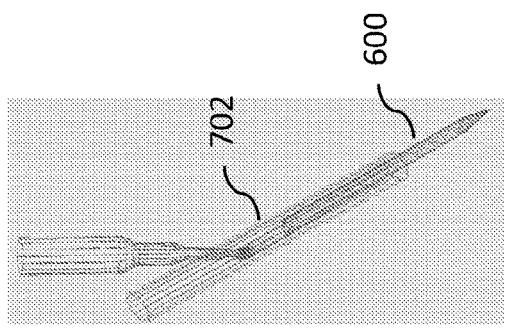
Figure 7D:
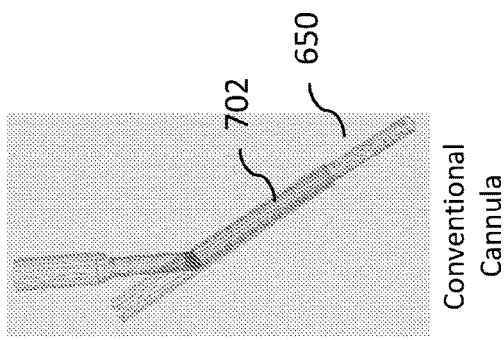
FIGS. 7c-d illustrate a conventional percutaneous rectilinear cannula being inserted into the vessel.
Figure 7C:
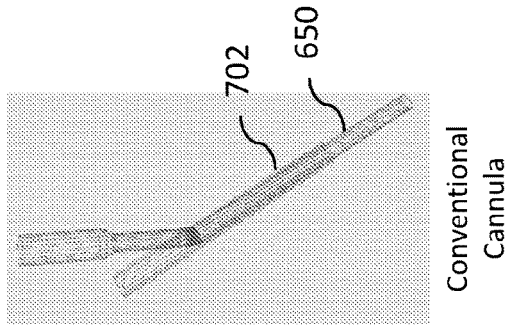

FIGS. 7a-b illustrate cannula 600 (as shown in FIG. 6a) being inserted into a vessel 702, according to some implementations of the current subject matter. By contrast, FIGS. 7c-d illustrate a conventional percutaneous rectilinear cannula 650 (as shown in FIG. 6b) being inserted into the vessel 702. Referring back to FIG. 7a, the cannula 600 can be placed into a collapsed or contracted configuration for placement through an access orifice created in a wall of the access vessel 702. The diameter of the bidirectional cannula 600 at the point of insertion can be smaller than the diameter of the conventional percutaneous rectilinear cannula 650 (as shown in FIG. 7c).

Once inside the vessel 702, the cannula's bottom portion 606 and/or the segment 602 can be expanded up to the surface of the interior wall of the vessel 702. Such expansion can be accomplished despite the small access orifice of the vessel 702. Once inserted, the diameter of the bidirectional cannula 600 at the point of insertion can be smaller than the diameter of the conventional percutaneous rectilinear cannula 650 (as shown in FIG. 7d). The diameter of the bidirectional cannula 600 within the target vessel 702 can be larger than the diameter of the conventional percutaneous rectilinear cannula 650.

Figure 8B:
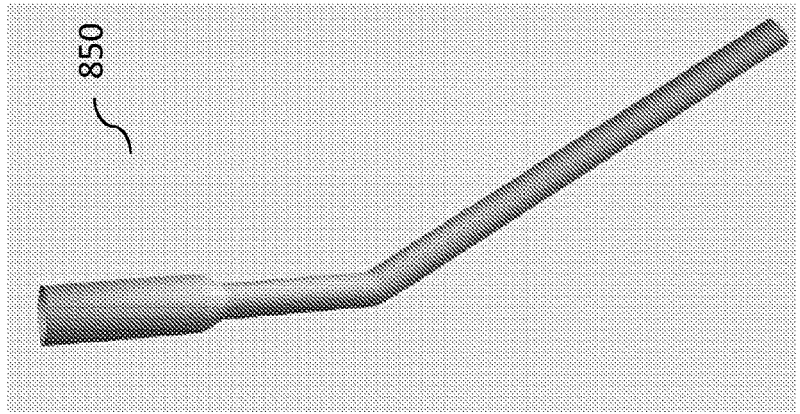
FIGS. 8b and 8d illustrate conventional cannulas.
Figure 8A:
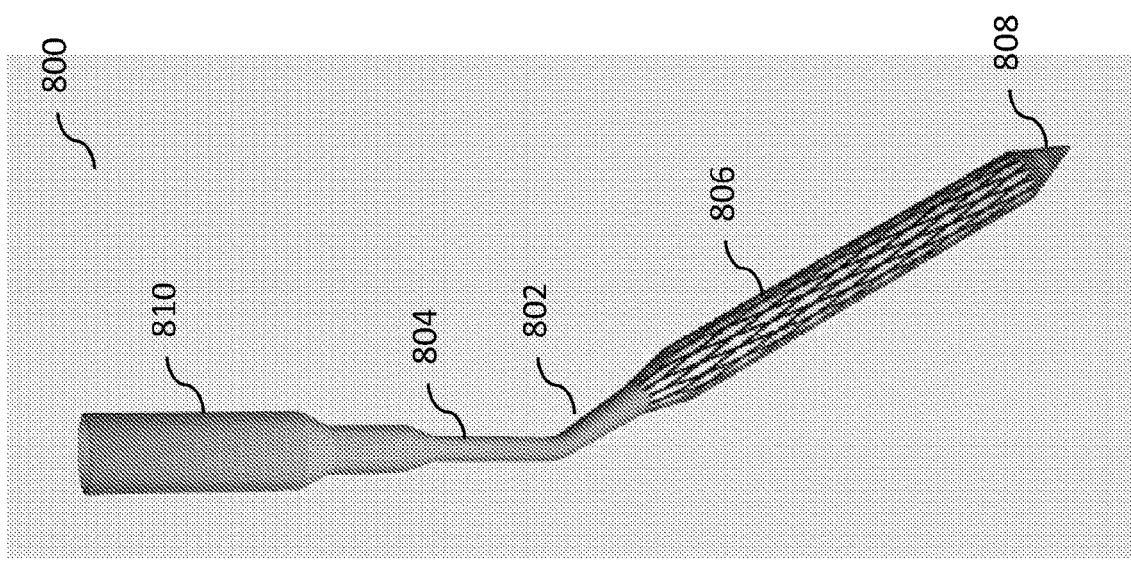
FIGS. 8a and 8c illustrate exemplary cannulas, according to some implementations of the current subject matter.

FIG. 8a illustrates an exemplary cannula 800, according to some implementations of the current subject matter. By contrast, FIG. 8b illustrates a conventional rectilinear cannula 650, which is used for percutaneous insertion. Similar to cannula 600 shown in FIG. 6a, the cannula 800 can be a bidirectional cannula. The cannula 800 can be self-expanding and/or virtually wall-less. The cannula 800 can include a narrow segment 802, an upper portion 804, and a lower portion 806. At its proximate end, the narrow segment 802 can be coupled to the upper portion 804 and, at its distal end, the narrow segment 802 can be coupled to the lower portion 806. The diameter of the narrow segment 802 can be smaller than the upper portion 804 and smaller than the diameter of the lower portion 806 when the lower portion 806 is in an expanded state, as shown in FIG. 8a. The lower portion 806 can also include a distal tip 808, which can be used for entry into the target vessel. The upper portion 804 of the cannula 800 can be designed for connection to the bypass tubing 810. The lower portion 806 of the cannula 800 is capable of contracting and expanding and, thereby can achieve diameter that is larger than the diameter of the narrow segment 802 and/or the diameter of the upper portion 804. The narrow segment 802 can also be collapsed prior to insertion, and re-expanded in situ. This can be helpful in minimizing a diameter of an access orifice created in a wall of the access vessel (not shown in FIG. 8a). In some implementations, the upper portion 804 and the narrow segment 802 can be covered with a thin water-tight coating. The lower portion 806 can be positioned within the vessel. It can be un-coated and/or virtually wall-less.

Figure 8D:
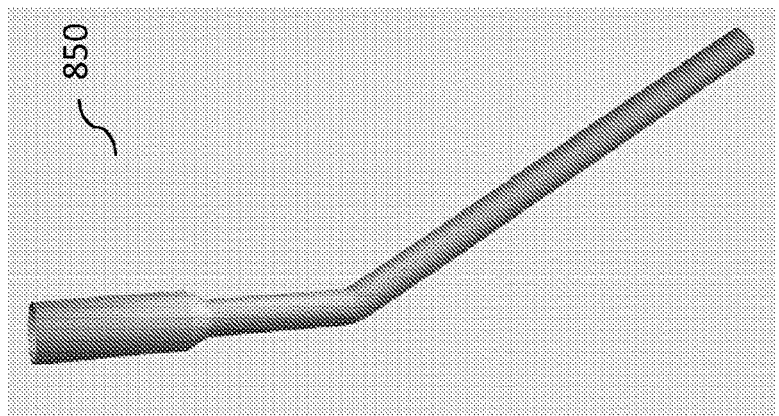
Figure 8C:
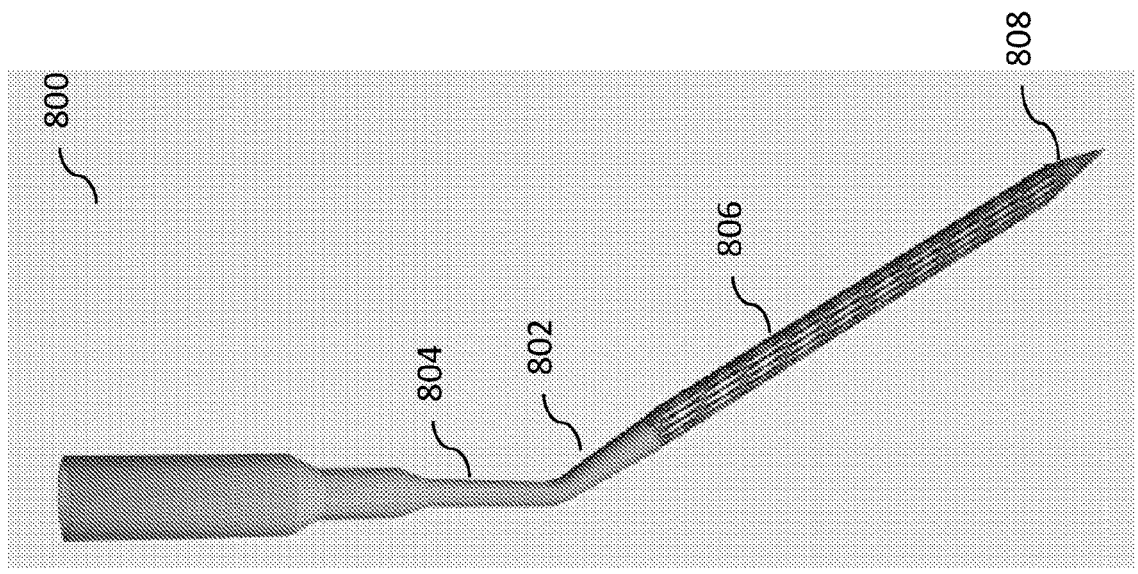

FIG. 8a illustrates the cannula 800 in an expanded configuration, where the lower portion 806 has been expanded (e.g., when placed inside the target vessel). FIG. 8c illustrates the bidirectional cannula 800 in collapsed configuration, according to some implementations of the current subject matter. In the collapsed configuration, the diameter of the lower portion 806 can be smaller than the diameter of the lower portion 806 in an expanded configuration (shown in FIG. 8a). The diameter of the lower portion 806 in the collapsed configuration can be smaller than the access orifice of the vessel. The diameter can be varied and/or can be dynamically adjustable as desired. By contrast, FIG. 8d illustrates the conventional rectilinear cannula 850. As shown in FIGS. 8c-d, the diameter of the collapsed bidirectional cannula 800 can be made smaller than the diameter of the conventional percutaneous rectilinear cannula 850.

Figure 9B:
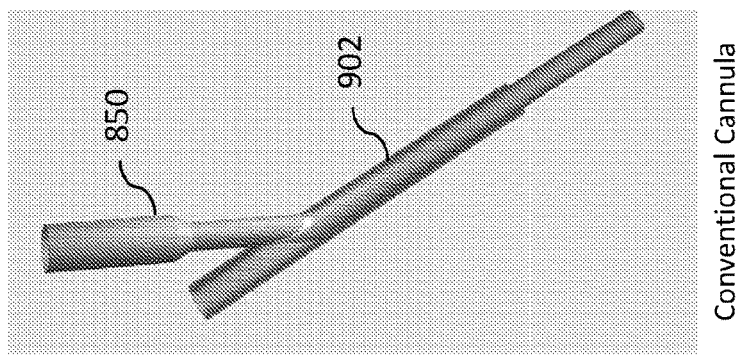
FIG. 9b illustrates a conventional cannula.
Figure 9A:
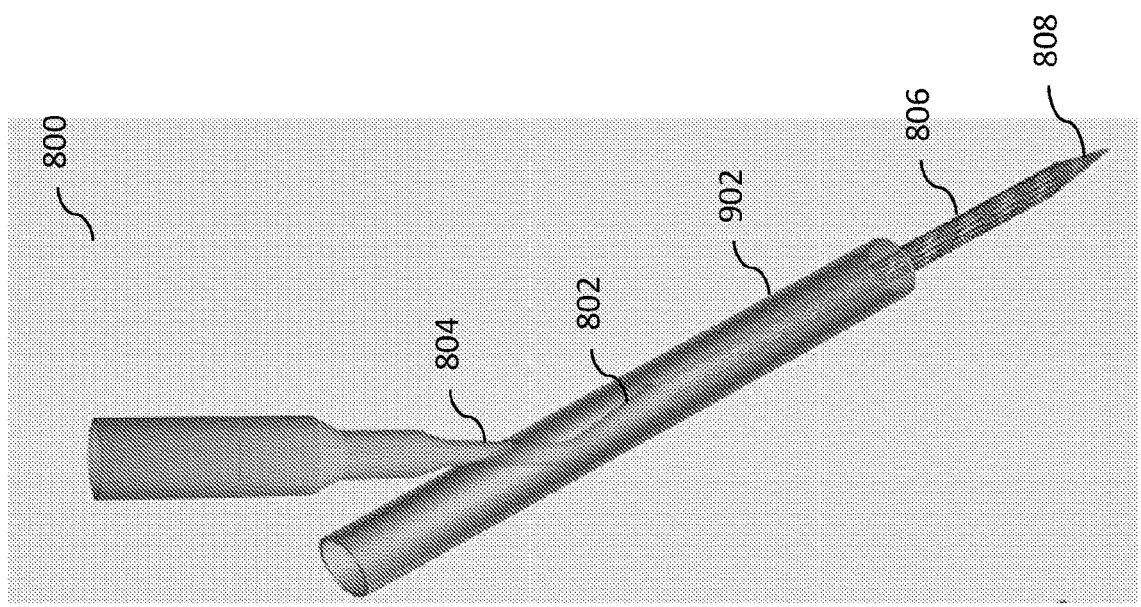
FIG. 9a illustrates an exemplary cannula, according to some implementations of the current subject matter.

FIGS. 9a-b illustrate cannula 800 (as shown in FIG. 8a) being inserted into a vessel 902, according to some implementations of the current subject matter. By contrast, FIGS. 9c-d illustrate a conventional percutaneous rectilinear cannula 850 (as shown in FIG. 8b) being inserted into the vessel 902. As shown in FIG. 9a, the cannula 800 can be placed into a collapsed or contracted configuration for insertion through an access orifice created in a wall of the vessel 902. The diameter of the bidirectional cannula 800 at the point of insertion can be smaller than the diameter of the conventional percutaneous rectilinear cannula 850 (as shown in FIG. 9c).

Once inside the vessel 902, the cannula's bottom portion 806 and/or the segment 802 can be expanded up to the surface of the interior wall of the vessel 902. Once inserted, the diameter of the bidirectional cannula 800 at the point of insertion can be smaller than the diameter of the conventional percutaneous rectilinear cannula 850 (as shown in FIG. 9d). The diameter of the bidirectional cannula 800 within the target vessel 902 can be larger than the diameter of the conventional percutaneous rectilinear cannula 850.

Figure 10B:
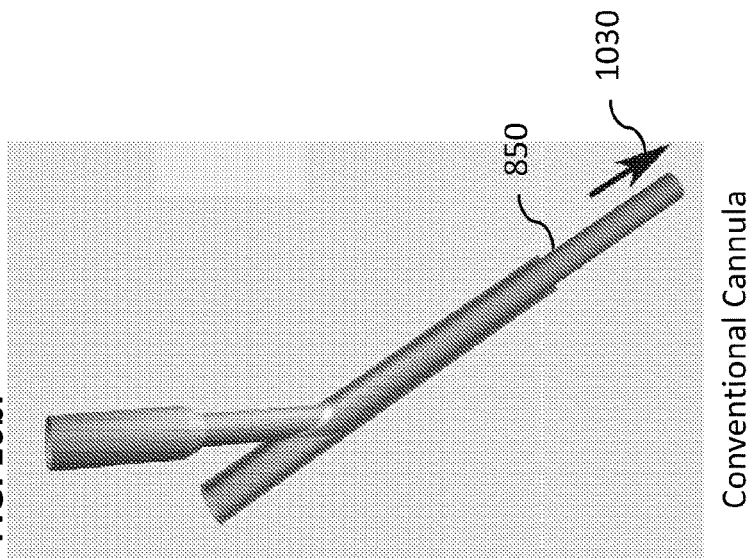
FIG. 10b illustrates a conventional cannula.
Figure 10A:
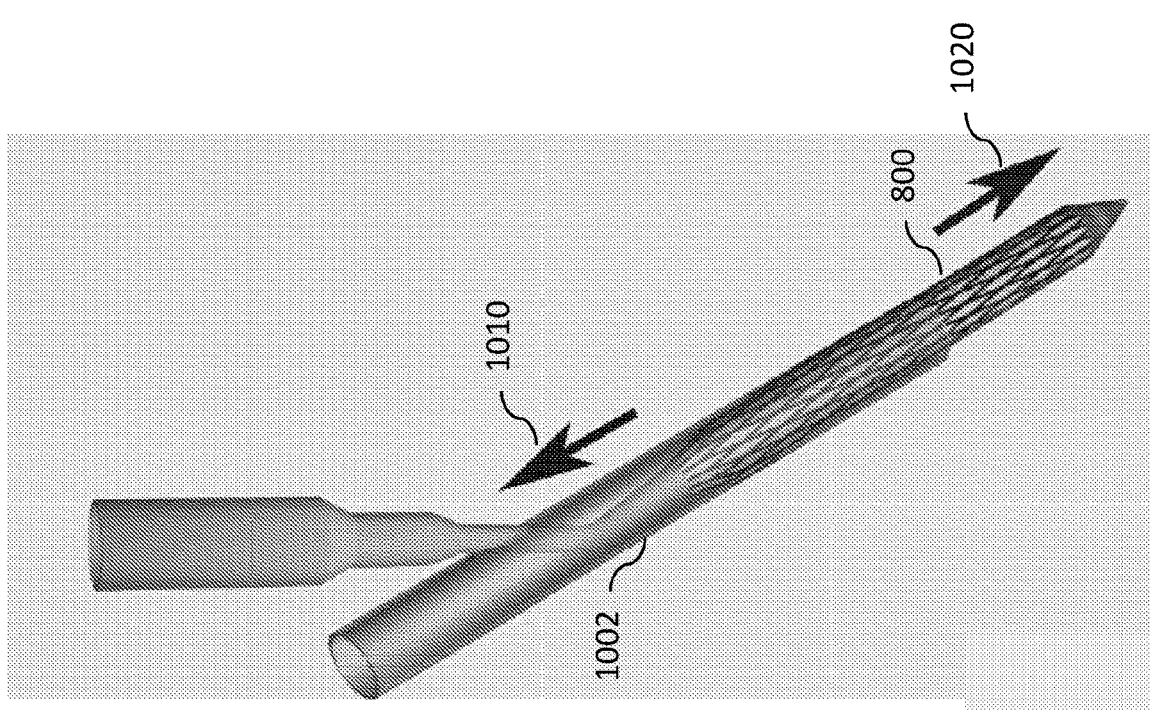
FIG. 10a illustrates an exemplary arterial cannula being placed in a vessel for accommodating an arterial flow, according to some implementations of the current subject matter.

FIG. 10a illustrates an exemplary arterial cannula 800 (as shown in FIG. 8a) being placed in a vessel 1002 for accommodating an arterial flow, according to some implementations of the current subject matter. By contrast, a conventional cannula 850 (as shown in FIG. 8b) for providing arterial flow is shown in FIG. 10b. As stated above, the diameter of the bidirectional cannula 800 at the point of insertion can be smaller than the diameter of the conventional percutaneous rectilinear cannula 850 (as shown in FIG. 10b). The diameter of the bidirectional cannula 800 within the target vessel can be larger than the diameter of the conventional percutaneous rectilinear cannula 850.

In some implementations, using the virtually wall-less design of the current subject matter's bi-directional cannula 800, perfusion can be achieved in both directions for the arterial side, as shown by arrows 1010 (antegrade direction) and 1020 (retrograde direction) in FIG. 10a, In contrast, conventional percutaneous rectilinear cannula 850 can typically provide only unidirectional flow 1030, as shown in FIG. 10b, due to the fact that the entire vessel lumen available at the point of access is occupied by the cannula respectively its wall.

Figure 11B:
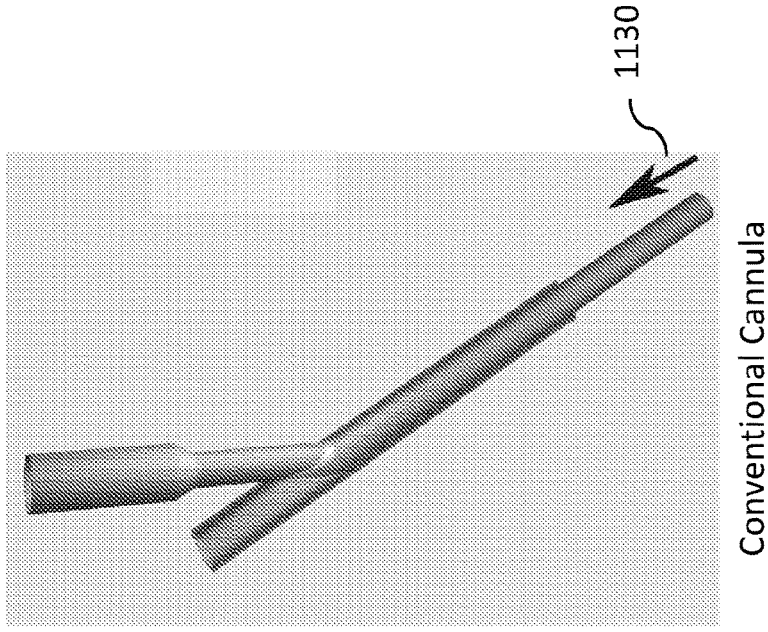
FIG. 11b illustrates a conventional cannula.
Figure 11A:
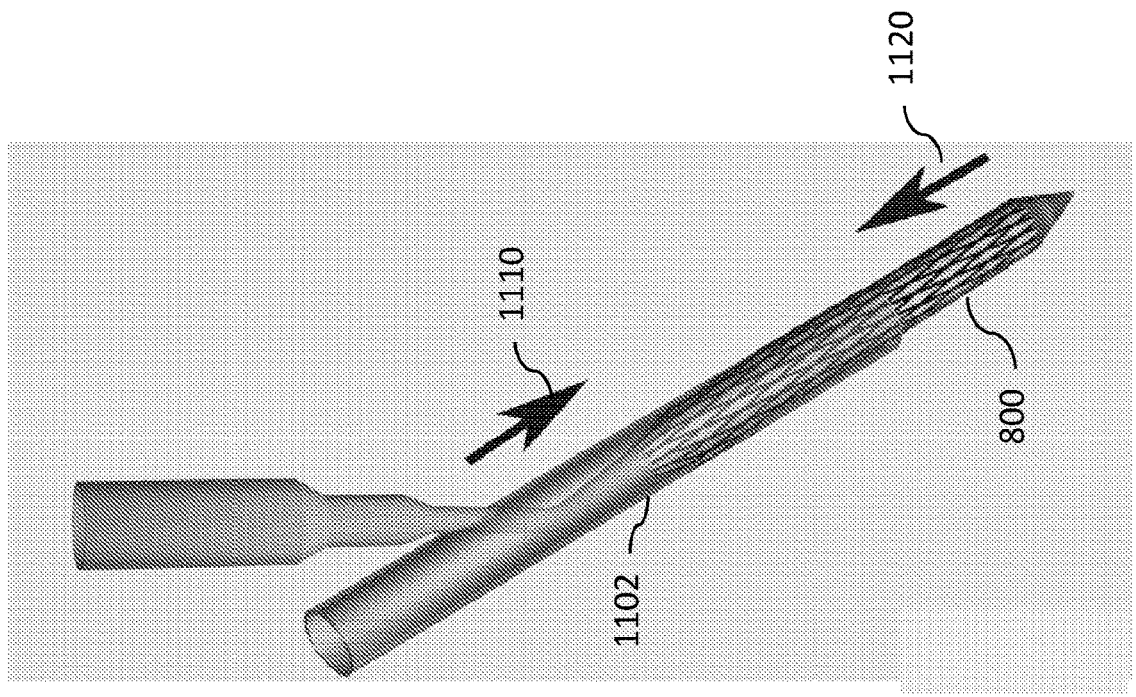
FIG. 11a illustrates an exemplary venous cannula being placed in a vessel for accommodating venous drainage, according to some implementations of the current subject matter.

FIG. 11a illustrates an exemplary venous cannula 800 (as shown in FIG. 8a) being placed in a vessel 1102 for accommodating venous drainage, according to some implementations of the current subject matter. By contrast, a conventional venous cannula 850 (as shown in FIG. 8b) for providing venous drainage is shown in FIG. 11b. As stated above, the diameter of the bidirectional cannula 800 at the point of insertion can be smaller than the diameter of the conventional percutaneous rectilinear cannula 850 (as shown in FIG. 11b). The diameter of the bidirectional cannula 800 within the target vessel can be larger than the diameter of the conventional percutaneous rectilinear cannula 850.

In some implementations, using the virtually wall-less design of the current subject matter's bi-directional cannula 800, venous drainage can be achieved in both directions, as shown by arrows 1110 (antegrade direction from the limb) and 1120 (retrograde direction from vena cava) in FIG. 11a. The directions are opposite of those shown in FIG. 10a for the arterial flows. In contrast, conventional percutaneous rectilinear cannula 850 can typically provide only unidirectional flow 1130, as shown in FIG. 11b, due to the fact that the entire vessel lumen available at the point of access is occupied by the cannula respectively its wall.

In some implementations, the current subject matter can include one or more of the following inventive features and/or advantages. The current subject matter's cannula can be a bidirectional cannula with a short narrow segment, which, upon insertion of the cannula through an access orifice or a point of insertion in the vessel, can be disposed at the point of insertion. The cannula can have a pre-formed diabolo shape. The bidirectional cannula can have a self-expanding design, which can take advantage of the venous anatomy over its entire length. The bidirectional cannula can be collapsed and/or re-expanded in the short narrow segment and/or any other portion of the cannula. The bidirectional cannula can have a virtually wall-less design in immediate proximity to the short narrow segment and/or anywhere else in the cannula design. The self-expanding design might not include circumscription orifices, can act as a scaffold, and, hence, can have no wall. The absence of cannula wall in the vicinity to its narrow segment (or anywhere else in the cannula) can allow for antegrade and/or retrograde flow (bidirectional perfusion on the arterial side, bidirectional drainage on the venous side). The self-expanding design can act as a temporary stent with the vessel wall providing the seal. In some implementations, the current subject matter cannula can include a dual lumen configurations (as disclosed in co-owned U.S. Pat. No. 8,992,455 to von Segesser, issued on Mar. 31, 2015, and entitled "Methods, apparatuses and systems for caval stenting for venous drainage," and co-owned U.S. Pat. No. 8,679,053 to von Segesser, issued Mar. 25, 2014, and entitled "High performance cannulas," the disclosures of which are reiterated and incorporated herein by reference in their entireties).

Further, the current subject matter's bi-directional design can have a preformed diabolo-shape in order to have its diameter restricted at a fraction of the access vessel diameter at the point of insertion (and/or immediately proximate to it) so that significant flow within the native vessel remains possible, despite the presence of the bidirectional cannula. Moreover, the current subject matter's cannula does not require dual cannulation, which is in contrast to conventional percutaneous rectilinear cannulas that typically require the entire access vessel diameter in order to achieve acceptable flow.

In some implementations, the current subject matter cannula can be used during at least one of the following procedures: percutaneous cannulation for cardiac surgery, open cannulation, ECMO, ECLS, hemofiltration, hemodialysis, other forms of dialysis, life supporting systems, draining and/or injecting blood, and/or other bodily fluids and gases, as well as suitable applications in non-medical fields, etc. The current subject matter cannula can provide a solution to a high pressure flow problems that are associated with these procedures as well as an increase of cannula diameter, which can be an issue with any vascular access device. Typically, dual lumen hemofiltration catheters sizes are 14 F and 11 F. The current subject matter cannula can achieve the same flow of existing dual lumen hemofiltration catheters of 14 F and 11 F sizes, by using an 11 F and 9 F catheters, respectively. The current subject matter cannula achieves this flow using a short narrow segment at the insertion point, thereby reducing bleeding complications at the time of removal (i.e., the smaller the orifice, the lesser the bleeding).

In some implementations, the current subject matter's cannula can include an upper portion for connection to a bypass tube, a narrow segment connected to the upper portion, and a lower portion. The diameter of the narrow segment can be smaller than the upper portion, thereby facilitating insertion using a smaller diameter access point in a vessel. The narrow segment can be inserted in a contracted state and can be capable of expanding subsequent to insertion. The upper portion and the segment may (or may not) be covered with a thin water-tight coating. The segment can also be self-expanding and/or virtually wall-less. The upper portion (or connecting portion located outside of the body) and the narrow segment can be covered whereas the lower or intravascular portion may or may not be covered with a thin water-tight coating. This segment can also be self-expanding and/or virtually wall-less. In some implementations, more or less than 5% of the cannula surface can be covered from the caval stenting application.

In some implementations, the cannula can be manufactured from a braid, to which a thin coating can be applied on one side (i.e., the covered part for insertion), imbedded the covered part at the end in silicone (i.e., the connecting part), and made a tip at the other end. However, if it is desired to drain blood with a femoral venous cannula from a (cardiac) cavity, e.g., the left atrium, a covered cannula can be used within the vena cava, and only after crossing a wall, e.g., the inter-atrial septum, an uncovered or covered tip can be used. An ability to expand the cannula over a long distance can improve cannula's performance.

In some implementations, the cannula can be expanded/contracted using mechanisms and/or methods disclosed in co-owned U.S. Pat. No. 8,992,455 to von Segesser, issued on Mar. 31, 2015, and entitled "Methods, apparatuses and systems for caval stenting for venous drainage," and co-owned U.S. Pat. No. 8,679,053 to von Segesser, issued Mar. 25, 2014, and entitled "High performance cannulas," the disclosures of which are reiterated and incorporated herein by reference in their entireties. Further, the materials, as well as some and/or all of the sizes of some or all portions of the cannula (except the pre-formed narrow segment) that can be used to can be similar to those disclosed in co-owned U.S. Pat. No. 8,992,455 to von Segesser, issued on Mar. 31, 2015, and entitled "Methods, apparatuses and systems for caval stenting for venous drainage," and co-owned U.S. Pat. No. 8,679,053 to von Segesser, issued Mar. 25, 2014, and entitled "High performance cannulas," the disclosures of which are reiterated and incorporated herein by reference in their entireties. In some implementations, the cannula can be bendable.

In some implementations, the cannula can be collapsed using a mandrel, inserted over a guide wire and expanded in situ (within the target vessel). This process can be similar to the processes disclosed in co-owned U.S. Pat. No. 8,992,455 to von Segesser, issued on Mar. 31, 2015, and entitled "Methods, apparatuses and systems for caval stenting for venous drainage," and co-owned U.S. Pat. No. 8,679,053 to von Segesser, issued Mar. 25, 2014, and entitled "High performance cannulas," the disclosures of which are reiterated and incorporated herein by reference in their entireties.

FIG. 12a illustrates an exemplary arterial bidirectional cannula 1200, according to some implementations of the current subject matter. By contrast, FIG. 12b illustrates a conventional arterial cannula 1250. Referring back to FIG. 12a, the cannula 1200 can be inserted into a tubing 1210 (e.g., a silicone tubing and/or any other tubing) for initiation of perfusion. The cannula 1200 can allow bidirectional flow of fluids (e.g., blood and/or any other fluids) once inserted into a vessel, which is shown by the arrows 1204, 1206. Arrow 1206 illustrates an antegrade flow and arrow 1204 illustrates a retrograde flow. In some exemplary non-limiting implementations, the outflow measured at both ends of the tubing 1210 with an afterload can be on the order of 60 mmHg. By contrast, the conventional cannula 1250 as shown in FIG. 12b produces substantially no antegrade flow 1216 and is capable of only producing retrograde flow 1214.

Figure 14:
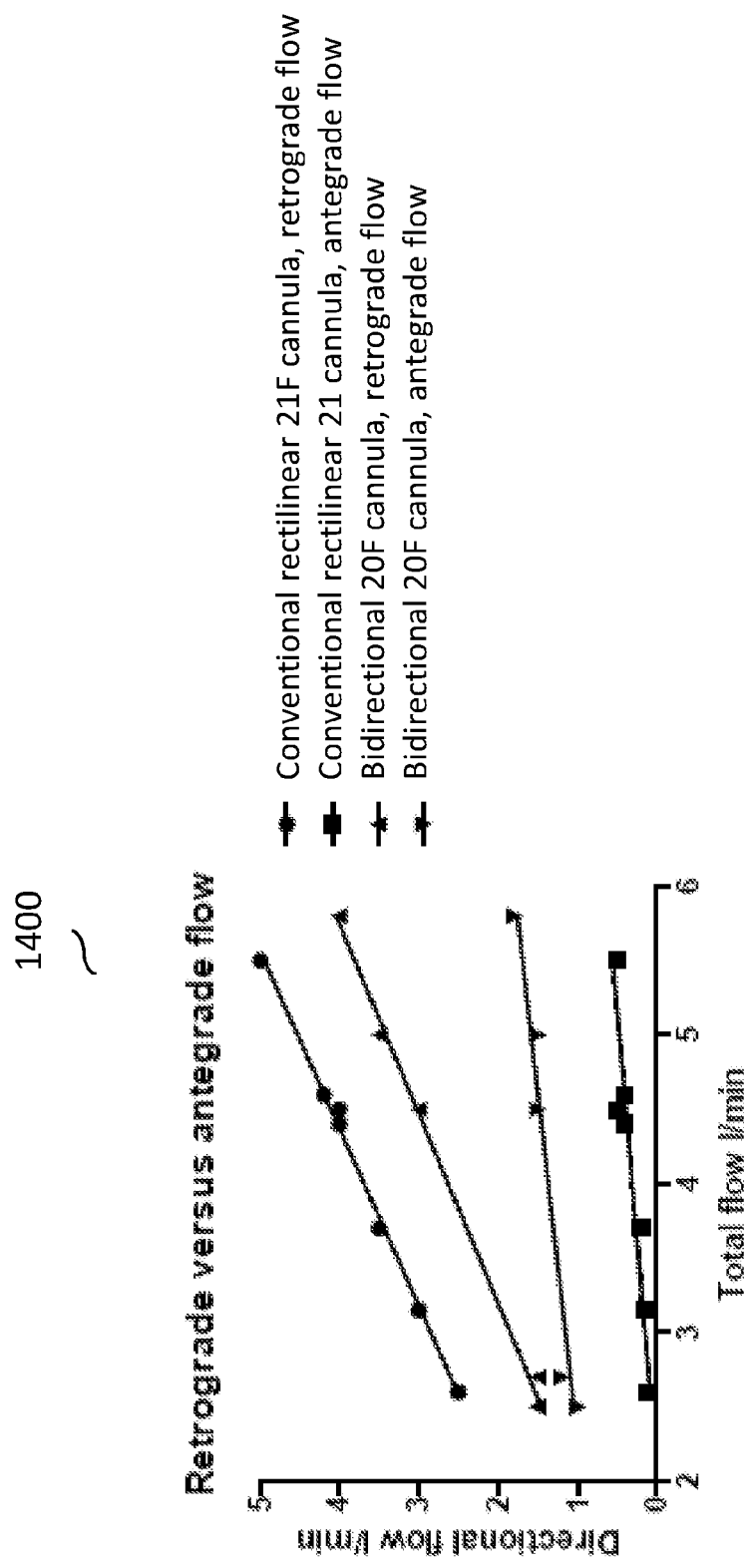
FIG. 14 illustrates an exemplary plot illustrating experimental flow measurements using the arterial cannula and a conventional rectilinear cannula.

FIG. 14 illustrates an exemplary plot 1400 illustrating experimental flow measurements using the arterial cannula 1200 and a conventional rectilinear cannula 1250. For each measurement, one of the cannulas 1200 and 1250 has been inserted into a vessel (or any other tubing) and connected to a pumping device. In this experimental measurement, cannula 1200 having a 20 F diameter was used and conventional rectilinear cannula 1250 having a 21 F diameter was used.

In the plot 1400, a pump flow is shown on the horizontal axis of the plot and directional flow is shown in the vertical axis. As shown in FIG. 14, outflow for the conventional rectilinear 21 F cannula is essentially retrograde (i.e., towards the aorta, as shown by "full circles" in FIG. 14). There is very little antegrade flow (i.e., towards the limb, as shown by "full squares" in FIG. 14). Outflow for the bidirectional cannula 1200 can be mainly retrograde (i.e., towards the aorta, as shown by "full triangles" in FIG. 14). However, approximatively one third of the flow can be antegrade (i.e., towards the limb, as shown by "full inverted triangles" in FIG. 14). As shown in FIG. 14, perfusion of the limb can be superior with the bidirectional cannula 1200 as compared to the conventional cannula 1250.

Figure 13A:
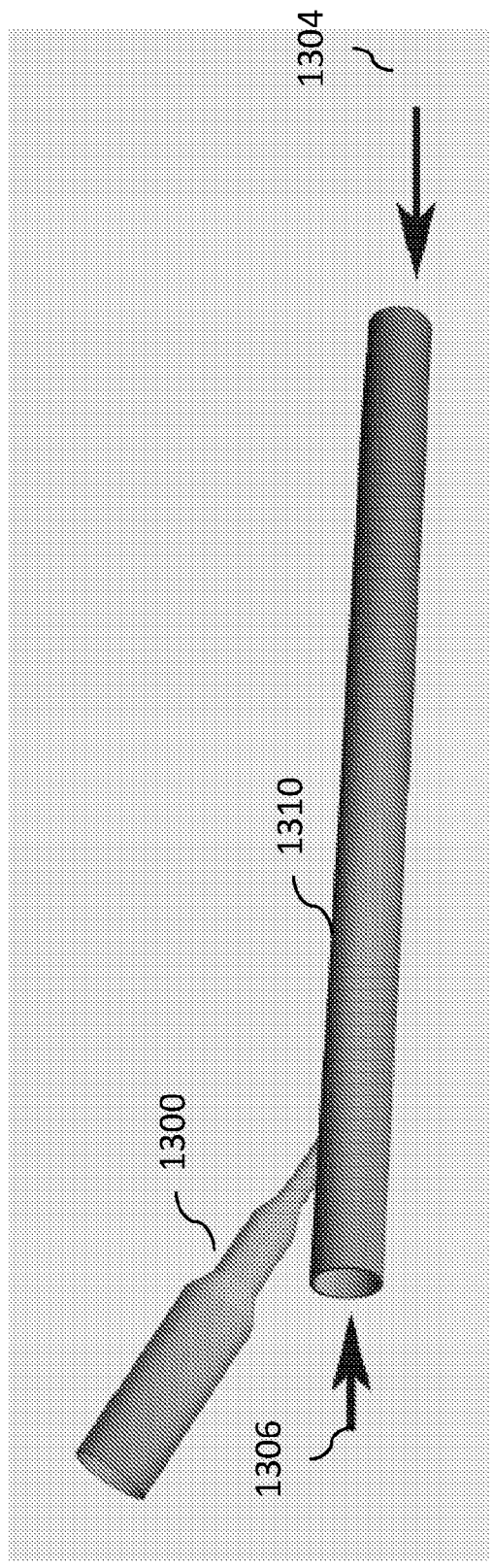
FIG. 13a illustrates an exemplary venous bidirectional cannula, according to some implementations of the current subject matter.
Figure 13B:
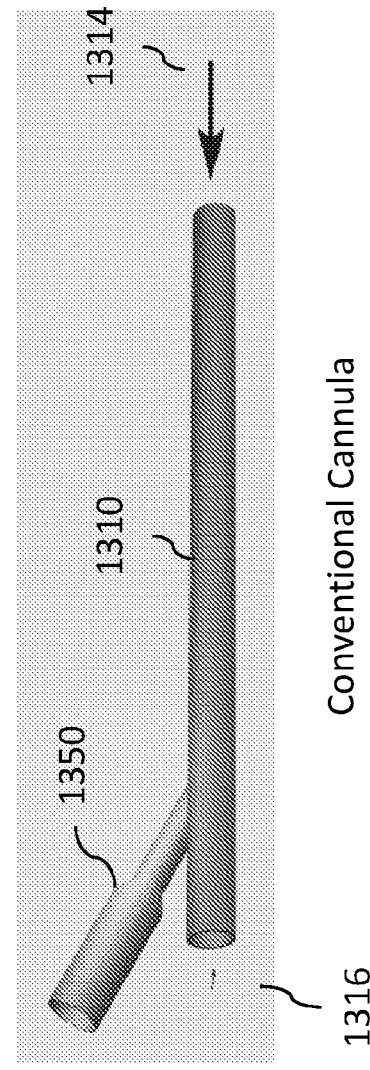
FIG. 13b illustrates a conventional arterial cannula.

FIG. 13*a* illustrates an exemplary venous bidirectional cannula 1300, according to some implementations of the current subject matter. By contrast, FIG. 13*b* illustrates a conventional arterial cannula 1350. As shown in FIG. 13*a*, the cannula 1300 can be inserted into a tubing 1310 (e.g., a silicone tubing and/or any other tubing) for initiation of drainage. The cannula 1300 can allow bidirectional flow of fluids (e.g., blood and/or any other fluids) once inserted into a vessel, which is shown by the arrows 1304, 1306. Arrow 1306 illustrates an antegrade flow (e.g., from the limb) and arrow 1304 illustrates a retrograde flow (e.g., from vena cava). By contrast, the conventional cannula 1350 as shown in FIG. 13*b* produces substantially no antegrade flow 1316 and is capable of only producing retrograde flow 1314.

Figure 15B:
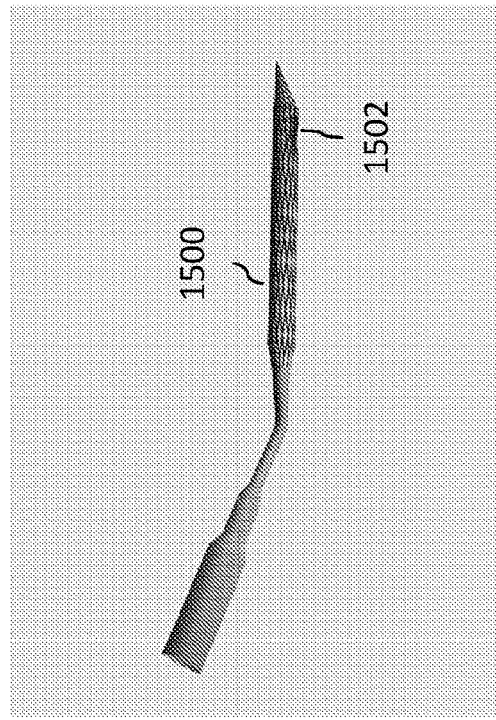
FIGS. 15a-e illustrate exemplary bidirectional cannulas cannula, according to some implementations of the current subject matter.
Figure 15A:
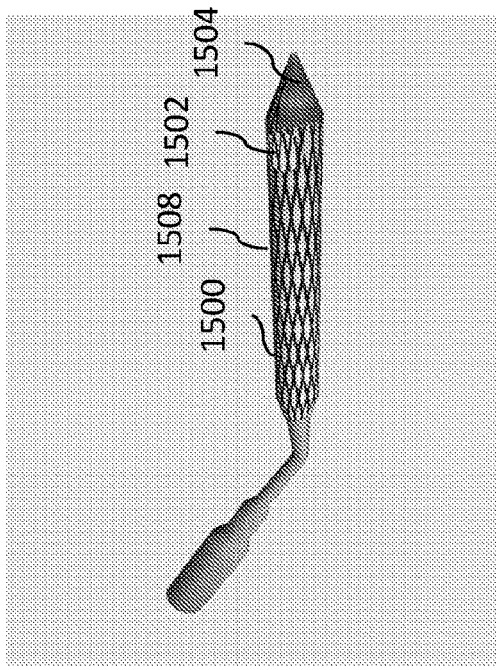
Figure 15C:
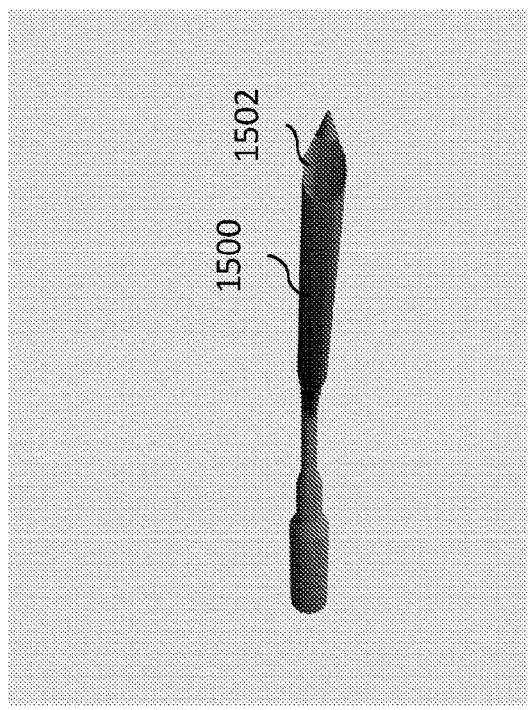

FIGS. 15*a-e* illustrate exemplary bidirectional cannulas, which can include one or more features of the bidirectional cannulas shown and discussed in connection with FIGS. 6*a*-14 above, and can include features that can provide directional and/or unrestricted flows. FIGS. 15*a-c* illustrate an exemplary cannula 1500 that can be used for providing a directional flow of fluids (FIG. 15*c* illustrates an exemplary covered cannula 1500 having a co-axial tip). The cannula 1500 can be self-expanding and can include at least one orifice 1502 and a tip 1504. The orifice 1502 can be disposed in the lower portion 1508 of the cannula 1500 and proximate to the tip 1504. The orifice 1502 can be positioned anywhere on the cannula. The orifice 1502 can be a lateral orifice. The orifice 1502 can provide a directional flow of fluids when the cannula is inserted into a vessel. The tip 1504 can include a mesh configuration, which can act as a diffuser when cannula is inserted into the vessel. One or more orifices that can have uniform and/or varying sizes and/or shapes can be disposed proximate to the cannula tip 1504 and can provide directional flows proximate to the tip of the cannula 1500. The direction of the flows can be varied based on at least one of the following: the position of the cannula 1500, size(s) of the orifice(s) 1502, shape(s) of the orifice(s) 1502, a number of orifices 1502, location(s) of the orifice(s) 1502, and/or any other factors, and/or any combination thereof.

Figure 15E:
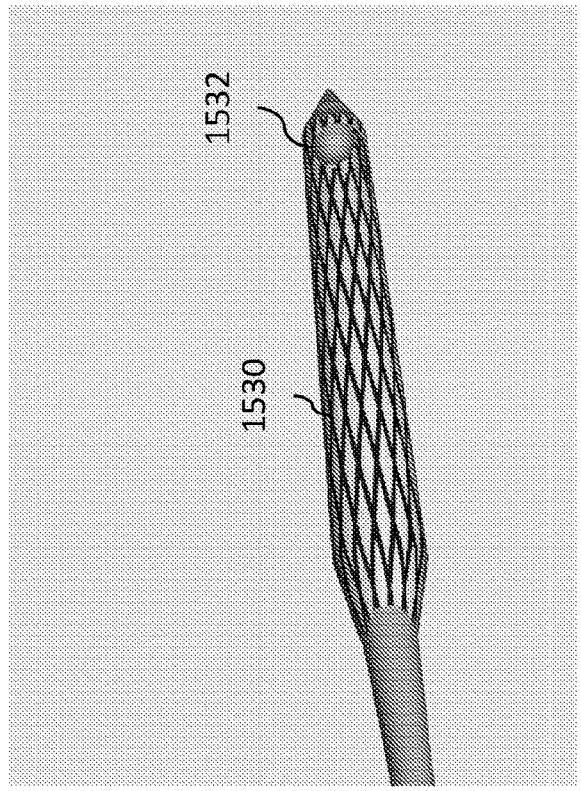
Figure 15D:
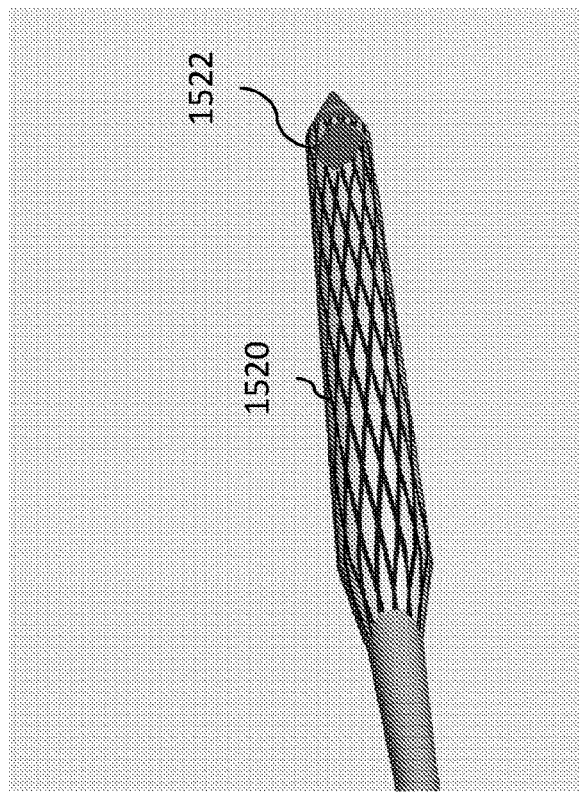

FIG. 15*d* illustrates an exemplary cannula 1520 having at least one deflector 1522 (e.g., an oblique plate), which can be disposed proximate to the tip of the cannula 1520. The location of the deflector(s) 1522 proximate to the tip of the cannula 1520 can result in a deflected outlet flow. In some implementations, the cannula 1520 can have any number of deflector(s) 1522, which can be have any shape, any size, location of the deflector(s), desired flow path, type of vessel receiving the cannula 1520, etc., and/or any combination thereof. Additionally, the deflector(s) 1522 can be mounted either by themselves and/or in combination with one or more lateral orifices (as described above with regard to FIGS. 15*a-c*).

FIG. 15*e* illustrates an exemplary cannula 1530 having at least one diffusor 1532 (e.g., a ball), which can be disposed proximate to the tip of the cannula 1530. The location of the diffusor(s) 1532 proximate to the tip of the cannula 1530 can result in a deflected and/or diffused outlet flow. In some implementations, the cannula 1530 can have any number of diffusor(s) 1532, which can be have any shape, any size, location of the diffusor(s), desired flow path, type of vessel receiving the cannula 1530, etc., and/or any combination thereof. Additionally, the diffusor(s) 1532 can be mounted either by themselves and/or in combination with one or more lateral orifices (as described above with regard to FIGS. 15*a-c*).

II. Bidirectional and Unidirectional Use Cannulas

In some implementations, the cannula can be used for providing a bidirectional flow of fluid and/or a unidirectional flow of fluid through a vessel. FIGS. 16*a-e* illustrate use of an exemplary bidirectional flow cannula, according to some implementations of the current subject matter. Bidirectional cannulas are also discussed above with regard to FIGS. 6*a*-15. FIGS. 17*a*-20 illustrate exemplary unidirectional flow cannulas, according to some implementations of the current subject matter.

A. Bidirectional Use Cannula

FIGS. 16*a-e* illustrate an exemplary bidirectional use cannula 1600, according to some implementations of the current subject matter. The cannula 1600 can include a cannula body 1610, a narrow segment 1602 (which can be short), an expandable section 1604, and a tip 1606. Similar to the cannulas discussed above in connection with FIGS. 6*a*-15, the cannula 1600 can be inserted into a vessel through an access orifice in a collapsed or unexpanded state and then expanded up to the surface of an interior wall of the vessel. The cannula 1600 can be coupled to various tubing, a pumping mechanism, and/or any other equipment that may be used for performing various medical procedures (e.g., cardiovascular procedures and/or any other type of procedures). The cannula can be used for arterial perfusion and/or venous drainage and/or both.

The expandable section 1604 can be disposed between the narrow segment 1602 and the tip 1606. The tip 1606 can be sized to fit through an access orifice and vessel. The cannula 1600 in a collapsed configuration can have a diameter that is smaller than the diameter(s) of the access orifice and/or access vessel and/or the target vessel. The relatively small diameter can allow advancement of the cannula in a collapsed state (as shown in FIG. 16*b*) through much smaller orifices/vessels and expansion of the cannula in situ. Additionally, the structure of the cannula 1600 and its ability to expand and contract can allow for simultaneous perfusion/drainage in one and/or both directions (i.e., bidirectional flow), i.e., antegrade and/or retrograde flows. This can avoid peripheral ischemia in an arterial applications and/or peripheral stasis of blood in venous applications.

Figure 16E:
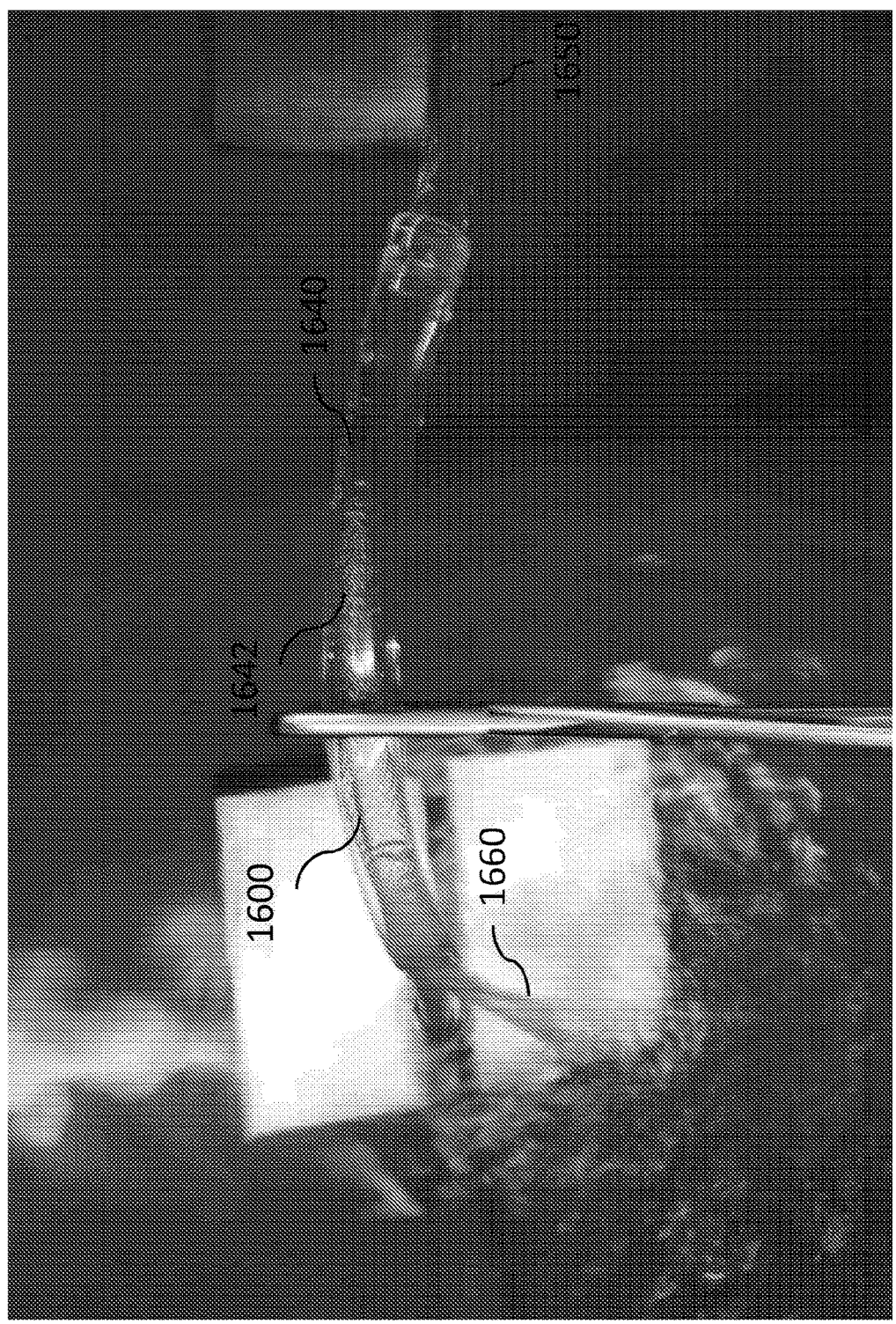

In some implementations, the narrow segment 1602 and/or the portion 1604 can be collapsed and passed through a small orifice and then re-expanded in situ using a mandrel a bougie, a balloon, a pressurization mechanism, a retraction mechanism, and/or any other device (not shown in FIGS. 16*a-e*). Further, in some exemplary implementations, the tip 1606 can include an orifice that can accommodate passage of a guidewire 1612 (as shown in FIG. 16*c*), whereby using the tip's orifice and a hollow mandrel, the bidirectional cannula 1600 can be inserted into a vessel over the guidewire 1612. After insertion through a small access orifice of a vessel and removal of the mandrel, the bidirectional cannula 1600 can be re-expanded to its original size and/or up to the surface of the interior wall of the target vessel (as shown in FIG. 16d) and/or any other desired size. As shown in FIG. 16d, the cannula 1600 can be passed through a 22 F orifice (which, for example, can be a point of insertion or access orifice) and its section 1604 can be expanded to a much larger size than the access orifice.

In some implementations, bidirectional perfusion (i.e., antegrade and retrograde) can be possible if the diameter of the narrow segment 1602 of the bidirectional cannula 1600 at the point of insertion has a cross diameter less than the diameter of the access vessel. As shown in FIG. 16e (which illustrates exemplary bench tests using the bidirectional cannula 1600 having the narrow segment 1602 being inserted in a larger tube 1640), the bidirectional cannula 1600 can be inserted from one side of the tube 1640 having a diameter greater than the diameter of the access orifice. In some exemplary implementations, the main flow produced by the cannula 1600 can be antegrade (i.e., from left to right) as shown by the large flow 1650 in FIG. 16e. FIG. 16e also shows that there is a backward flow 1660 (i.e., retrograde—from right to left). The experimental results comparing performance of the cannula 1600 having a 20 F diameter and a conventional 21 F cannula are illustrated in FIG. 14 and discussed above.

B. Unidirectional Use Cannula

As stated above, FIGS. 17a-20 illustrate exemplary unidirectional flow cannulas, according to some implementations of the current subject matter. The unidirectional flow cannulas, similar to the bidirectional flow cannulas, can be inserted through an access orifice in a contracted configuration and then expanded in situ up to the surface of an interior wall of the vessel and/or any other desired size. The cannula can be inserted over a guidewire and can be contracted (and/or stretched) and/or collapsed using a mandrel a bougie, a balloon, a pressurization mechanism, a retraction mechanism, and/or any other suitable device.

Figure 17B:
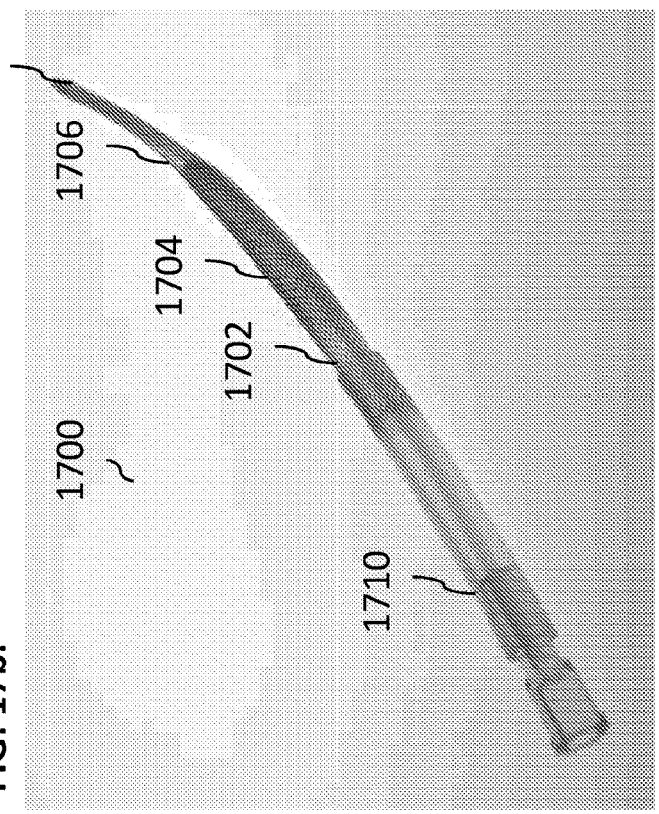
FIGS. 17a-b illustrate an exemplary unidirectional flow cannula, according to some implementations of the current subject matter.
Figure 17A:
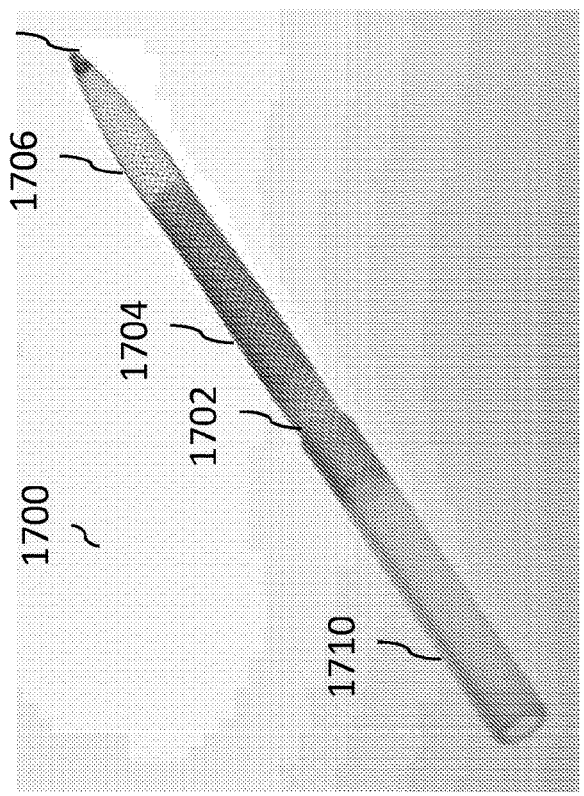

FIGS. 17a-b illustrate an exemplary unidirectional flow cannula 1700, according to some implementations of the current subject matter. The cannula 1700 can include a cannula body 1702, an upper portion 1704, an expandable portion 1706 and a tip 1708. The upper portion 1704 of the cannula 1700 can be coupled to various tubing 1710 (and/or a pump, and/or any other devices). In some implementations, the tip 1708 can include an orifice through which a guidewire can be inserted.

The expandable portion 1706 can assume an expanded configuration (as shown in FIG. 17a) and/or contracted configuration (as shown in FIG. 17b). In the expanded configuration, the expandable portion 1706 can have a larger diameter than in the contracted configuration. In the contracted configuration (as shown in FIG. 17b, the cannula 1700 can be inserted through an access orifice in a vessel for advancement to the target vessel and/or target location. Once the cannula has been placed in the target vessel and/or target location (which can be confirmed through, for example, x-ray, and/or any other scanning technology, and/or upon receiving an indication from a sensor that can be disposed on the cannula), the expandable portion 1706 can be expanded to a desired size (e.g., up to the surface of an interior wall of the target vessel). The expandable portion 1706 and/or the entire cannula can have any desired size, shape, curvature, length, flexibility, etc.

Figure 18C:
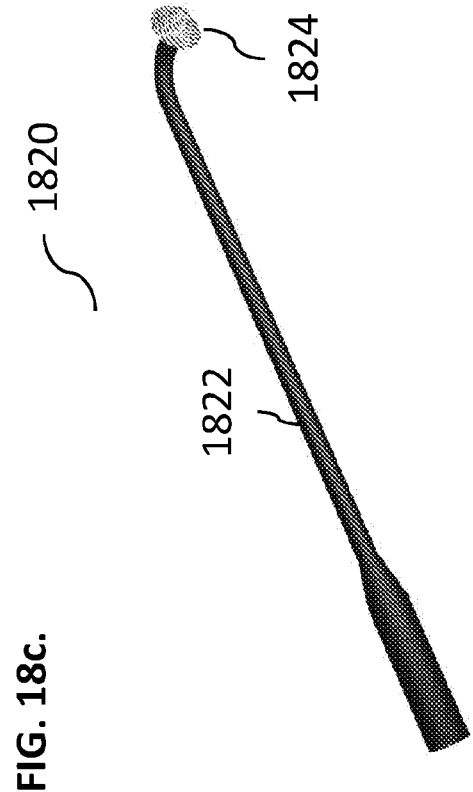
FIGS. 18a-c illustrate exemplary cannulas having a longer narrow section and a self-expanding cannula tip, according to some implementations of the current subject matter.
Figure 18A:
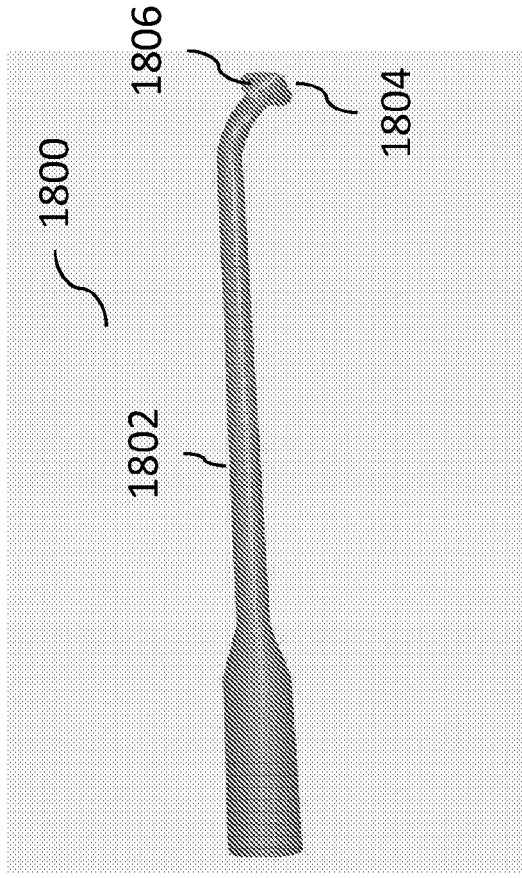
Figure 18B:
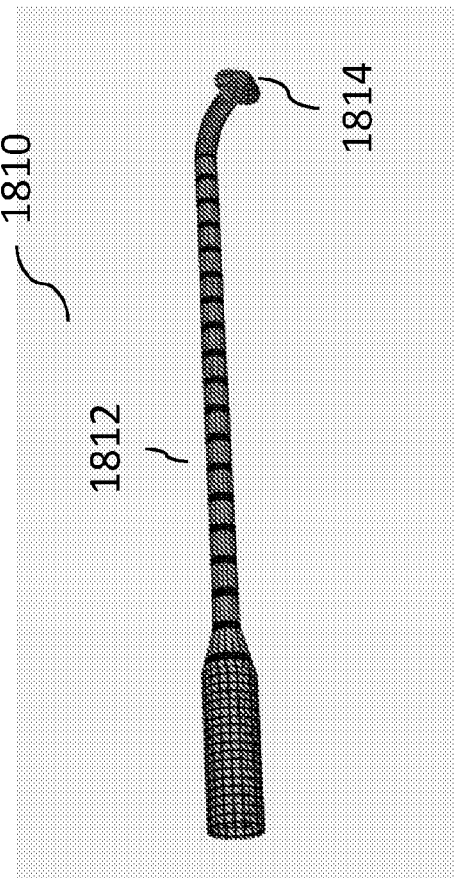

FIGS. 18a-c illustrate exemplary cannulas having a longer narrow section and a self-expanding cannula tip, according to some implementations of the current subject matter. The cannulas can have a variable diameter, where the longer narrow section allows reaching a vessel/atrial section with a larger diameter where the self-expanding cannula tip opens up (as shown in FIG. 18a), which can, in turn, allow for preferential perfusion/drainage of the target location (e.g., a vessel). As shown in FIG. 18a, a cannula 1800 can include a long narrow segment 1802, a self-expanding tip 1804 having multiple drainage orifices 1806. The cannula 1800 can be collapsed prior to insertion through an access orifice and/or access vessel and re-expanded at the target location (reaching the target location can be confirmed through, for example, x-ray, and/or any other scanning technology, and/or upon receiving an indication from a sensor that can be disposed on the cannula). The tip 1804 can have a larger diameter than at least one portion of the cannula 1800 and/or the narrow segment 1802 can act as a stabilizer. The shape and/or size of the tip 1804 can dependent on a particular implementation of the cannula 1800. The length of the segment 1802 can be determined based on a specific implementation and/or use of the cannula 1800. The number, size, location, shape, and/or other characteristics of orifices 1806 can be determined based on a particular implementation of the cannula 1800.

In some implementations, the cannula body can include a wire mesh, as shown, for example, in FIG. 18b, where cannula 1810 can be partially and/or fully covered by wire skeleton 1812. The cannula 1810 can a tip 1814 that can be located at the distant end of the wire skeleton 1812 and that can be stabilized at the target location. The tip 1814 can be similar to the tip 1804 shown in FIG. 18a. It can contain the same or different wiring as the wire skeleton 1812.

FIG. 18c illustrates an exemplary the cannula 1820, similar to cannulas 1800 and 1810, which can include a braided wire skeleton and a coating (e.g., a water-tight coating) 1822. A self-expanding tip 1824 of the cannula 1820 can be uncoated and can allow for targeted drainage and/or perfusion of vessels. The tip 1824 can be similar to the tips 1804 and 1814 and can contain the same or different wiring as the wire skeleton.

Figure 19:
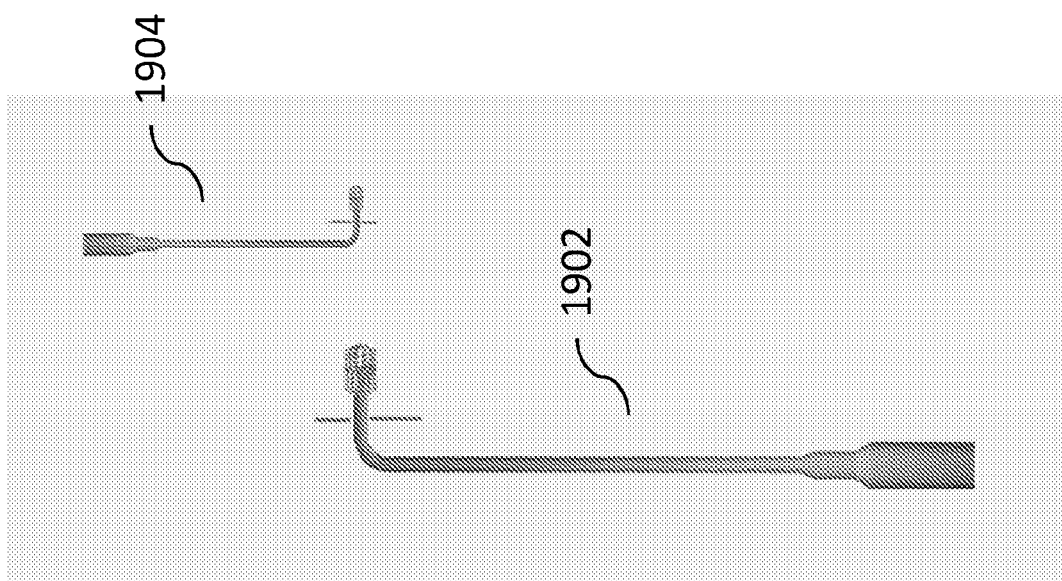
FIG. 19 illustrates a trans-parietal drainage and/or perfusal of a cavity, e.g., the left atrium in trans-septal fashion in either trans-femoral fashion, trans-subclavian fashion, and/or trans jugular fashion.

In some implementations, the cannulas shown in FIGS. 18a-c can be used to provide drainage and/or perfusion of vessels. For example, drainage/perfusion can be provided for the right atrium with venous trans-femoral, trans-jugular, or trans-subclavian access, etc. Similarly, the right ventricle, the pulmonary artery and/or its branches can be targeted, Further, the left atrium and/or the left ventricle and/or the aorta and/or its branches can be drained and/or perfused in trans-septal fashion in either trans-femoral fashion, as shown in FIG. 19, at 1902 or trans-jugular and trans-subclavian fashion at 1904. Further, the cannula tip can be stabilized in any hollow and/or solid organ at a specific position using local reversible and/or irreversible expansion.

Figure 20:
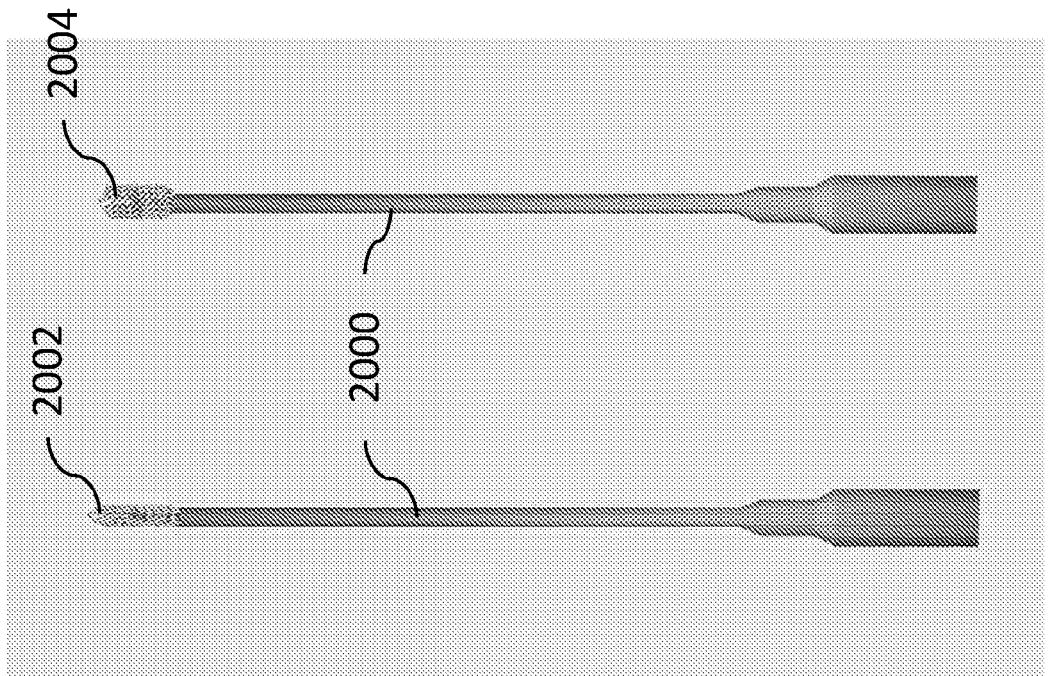
FIG. 20 illustrates an exemplary malleable cannula where the self-expanding tip has a contracted configuration and an expanded configuration, according to some implementations of the current subject matter.

In some implementations, for trans-venous access to the right atrium, the right ventricle, the pulmonary artery, the left atrium and the left ventricle (e.g., in transaortic fashion) and/or other compartments, a straight but malleable cannula configuration with self-expanding tip can be used. FIG. 20 illustrates an exemplary malleable cannula 2000 where the self-expanding tip has a contracted configuration, at 2002, and an expanded configuration, at 2004. The diameter of the tip in the expanded configuration 2004 can be greater than the diameter of the tip in the contracted configuration. In some implementations, the cannula 2000 can be used to perform targeted drainage and/or perfusion of any compartment.

III. Locking Mechanisms

In some implementation, the cannula can also include a locking mechanism, which can be a passive locking mechanism and/or an active locking mechanism. FIGS. 21-27 illustrate an exemplary cannula having a passive locking mechanism, according to some implementations of the current subject matter. FIGS. 28-32 illustrate an exemplary cannula having an active locking mechanism, according to some implementations of the current subject matter.

A. Passive Locking Mechanism

Figure 23B:
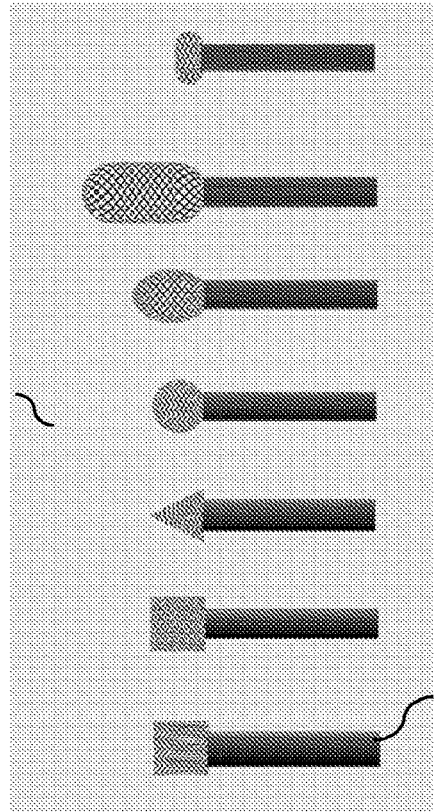
FIGS. 23a-c illustrate exemplary basket shapes, according to some implementations of the current subject matter.
Figure 23A:
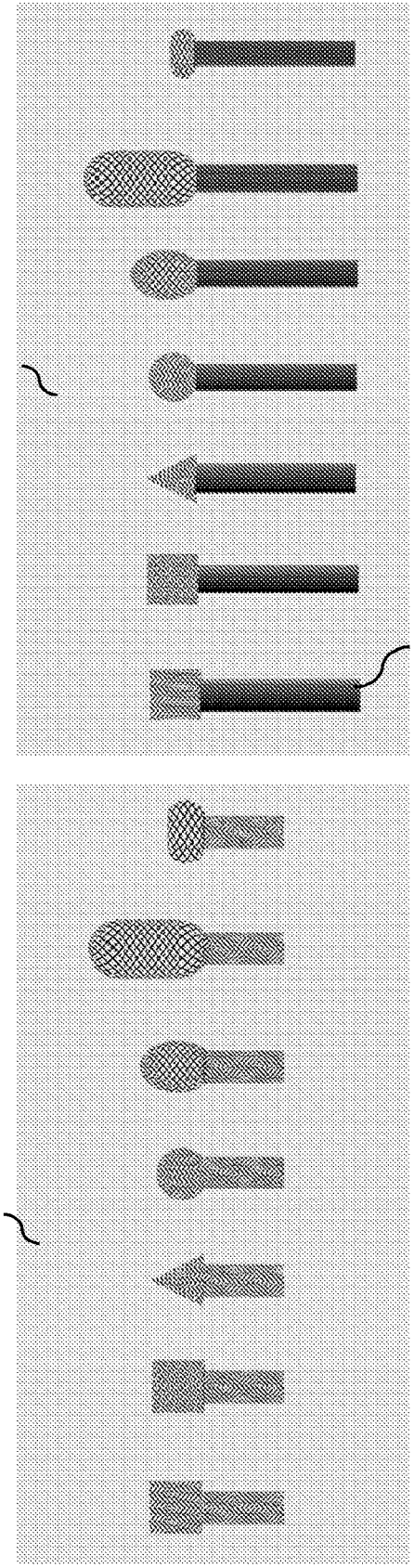
Figure 23C:
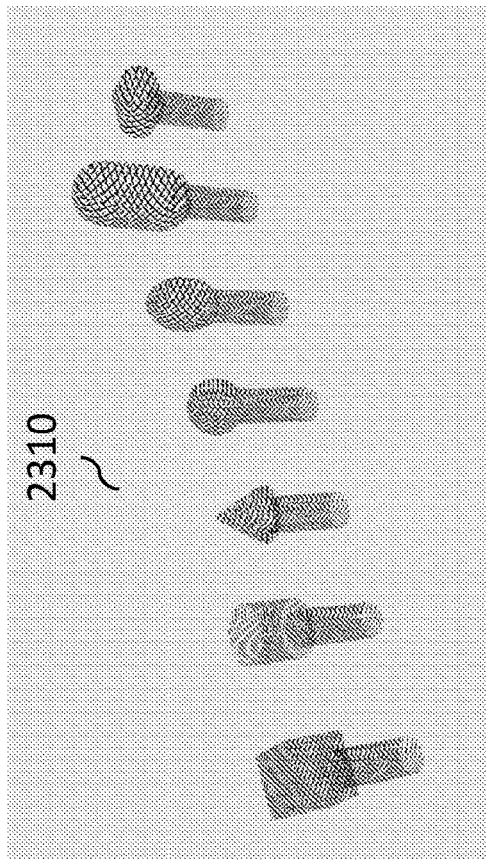
Figure 24:
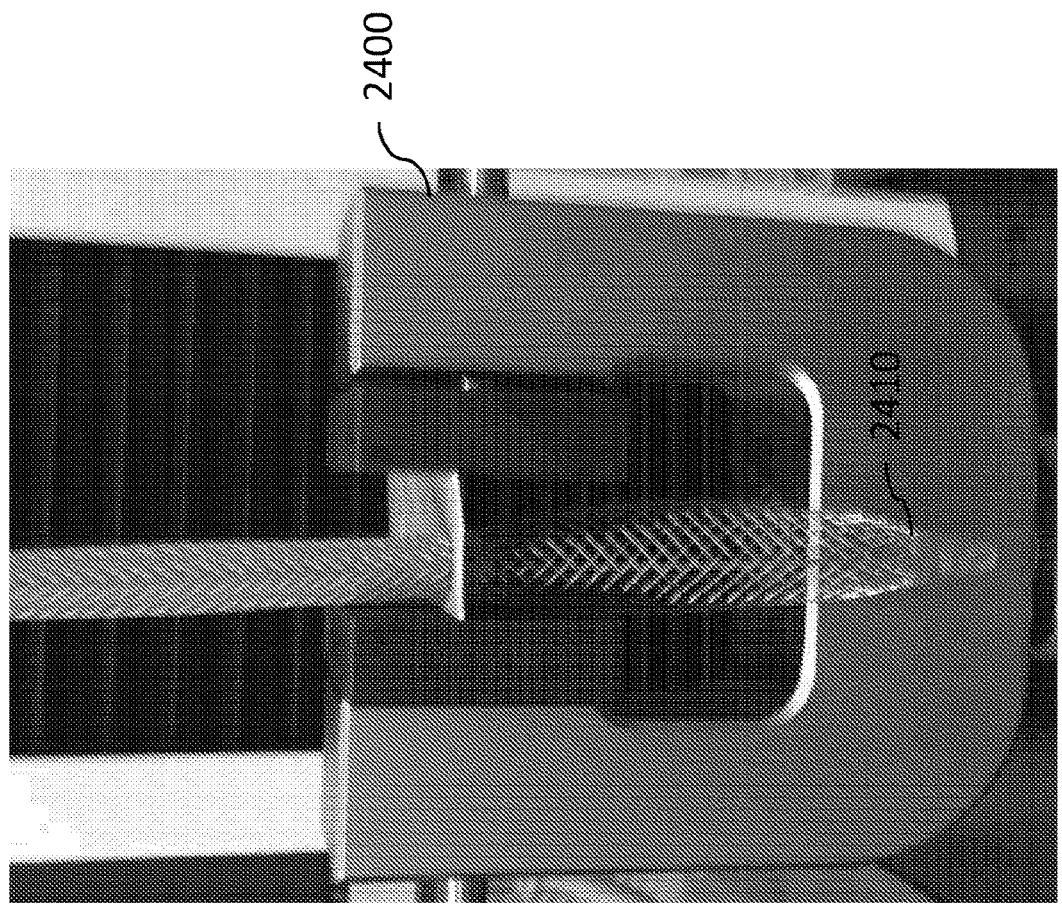
FIG. 24 illustrates exemplary lower claws of a traction bench with a braided cannula having a relatively narrow body covered with a watertight plastic coating, according to some implementations of the current subject matter.
Figure 27:
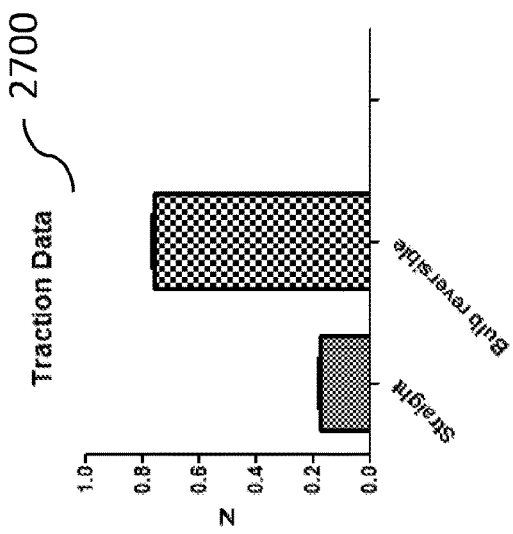
FIG. 27 illustrates another exemplary traction plot, according to some implementations of the current subject matter.
Figure 25:
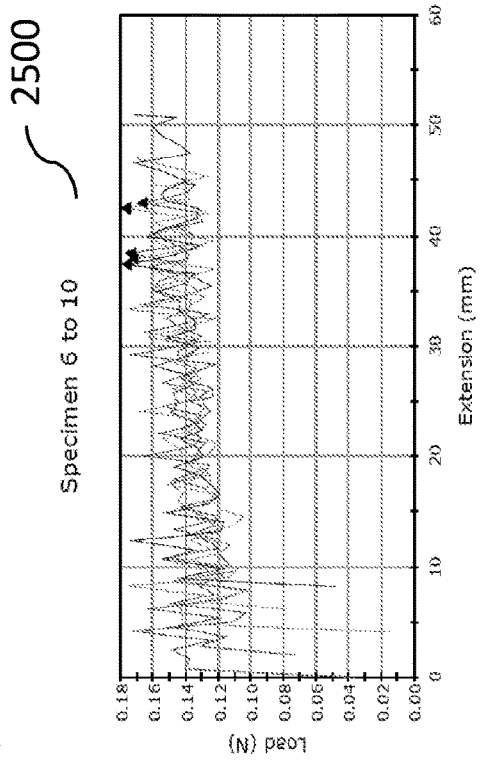
FIG. 25 illustrates exemplary traction plot, according to some implementations of the current subject matter.
Figure 26:
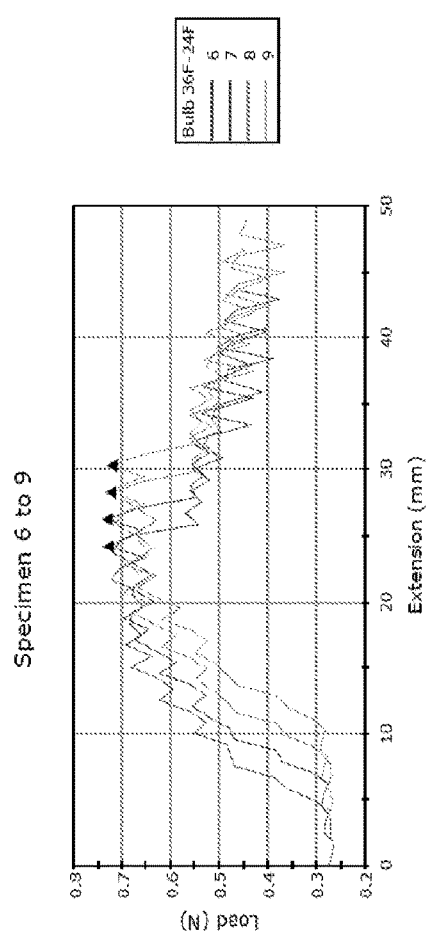
FIG. 26 illustrates another exemplary traction plot, according to some implementations of the current subject matter.

FIGS. 21-27 illustrate an exemplary cannula having a passive locking mechanism, according to some implementations of the current subject matter. Referring to FIG. 16d, an exemplary reversible locking mechanism is shown, where a pre-formed basket 1642 (e.g., a shape of a self-expanding tip, as discussed below) can expand beyond a narrow orifice. The resistance to pullback can be adjusted by the basket size, the basket configuration and the hoop strength of this self-expanding segment. Exemplary traction data is shown in FIGS. 25-27. If the form of the basket is consolidated with a traction member (which can be locked by simple bending at the other end of the device and/or by other mechanisms), as shown for example in FIGS. 29-30, the forces that may be required for removal can increase by at least one order of magnitude. In some exemplary implementations, the locking mechanisms can use a variety of mechanism, such as inverted cones with hooks (as shown in and discussed in connection with FIG. 28 (configuration 2800(G)). If the cones are pulled together, the hooks of one cone can capture filaments and/or hooks (e.g., on the opposite side) of the other cone and the shape change can become irreversible (as shown in and discussed in connection with FIG. 28 (configuration 2800(H)). The technical solutions that can allow to catch a filament can be applied for construction of an irreversible lock. By way of a non-limiting example, mechanisms similar to those used in a zipper can allow for creation a reversible lock. Alternatively, baskets can be designed in such a fashion that flattening the profile of the basket by stretching and/or other ways for insertion can require forces that are higher than the forces that may be required for tearing the access orifice of the target cavity and/or organ. Hence, the configuration change becomes quasi-permanent and/or "locked". However, in some circumstances, even this design may be un-locked by insertion of an adequate mandrel which can allow for collapsing the basket by stretching.

In some implementations, the self-expanding cannula tip can form a larger basket in a larger vascular zone as compared to the access vessel zone. The basket can characterize a shape and/or size of the self-expanding tip when the tip has been expanded in situ. The tip can be expanded using application of an external expansion force (e.g., using a mandrel, a bougie, a balloon, a pressurization mechanism, a retraction mechanism, and/or any other device). The passive stabilizing and/or locking mechanism can be used in connection with expansion of the cannula diameter beyond the access diameter. Several basket shapes/sizes with specific expansion forces can be used for stabilization of the self-expanding tip designed for targeted drainage and/or perfusion. In some implementations, an oversized basket can not only stabilize the tip in a larger compartment as compared to the access vessel (i.e., a locking mechanism), but can also do so in a rectilinear vessel configuration (i.e., friction). An example of the latter application is targeted drainage of the pulmonary artery, as discussed in, for example, von Segesser L. K. et al., "A Simple Way To Decompress The Left Ventricle During Venoarterial Bypass," Thorac. Cardiovasc. Surgeon, 2008:56, 337-341, the disclosure of which is incorporated herein by reference in its entirety.

Figure 21:
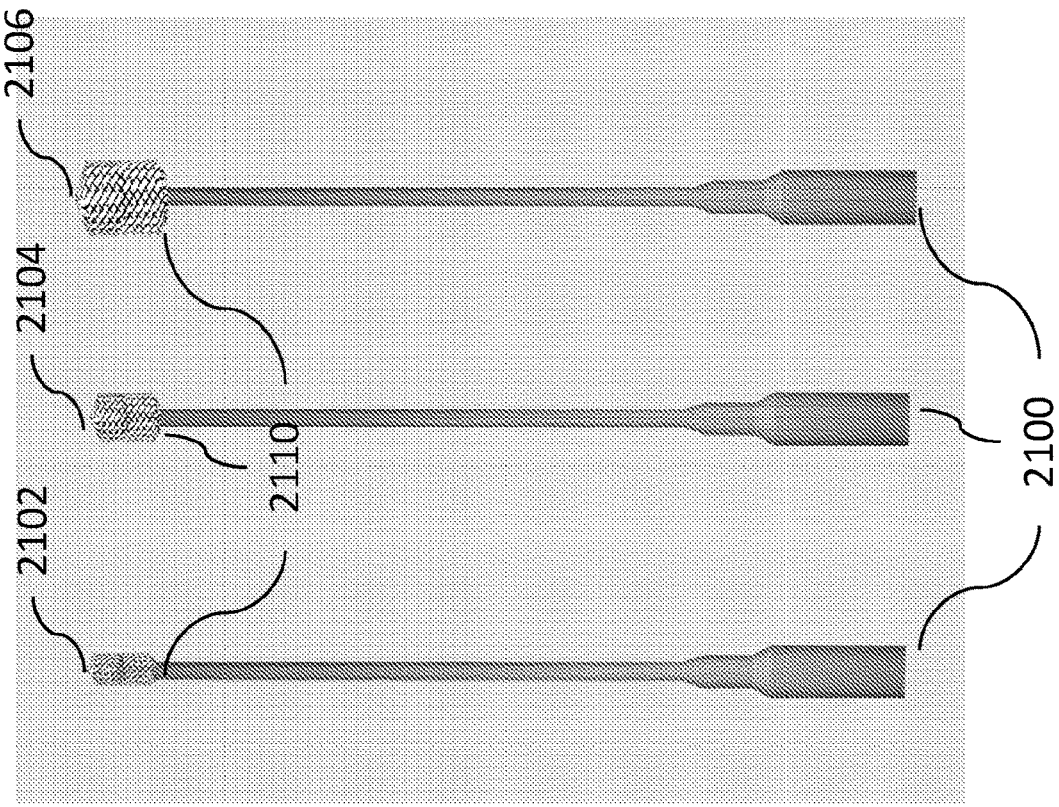
FIG. 21 illustrates exemplary cannula having a self-expandable tip, according to some implementations of the current subject matter.

FIG. 21 illustrates exemplary cannula 2100 having a self-expandable tip 2110, according to some implementations of the current subject matter. The tip 2110 can have baskets 2102-2106 of different sizes, according to some implementations of the current subject matter. The basket 2102 can be the smallest basket and the basket 2106 can be the largest basket, where the basket 2104 can have a size in between baskets 2102 and 2106. Basket size and expansion force can be sufficient for stabilization of the cannula tip 2110 in the target location (e.g., a vessel), depending on the anatomic configuration and/or wall quality. The baskets 2102-2106 can have a plurality of sizes and/or shapes, as will be discussed below. Further, specifically-designed cannula shapes can enhance positioning and/or the stability of the cannula 2100 in the target location (e.g., a vessel).

Figure 22:
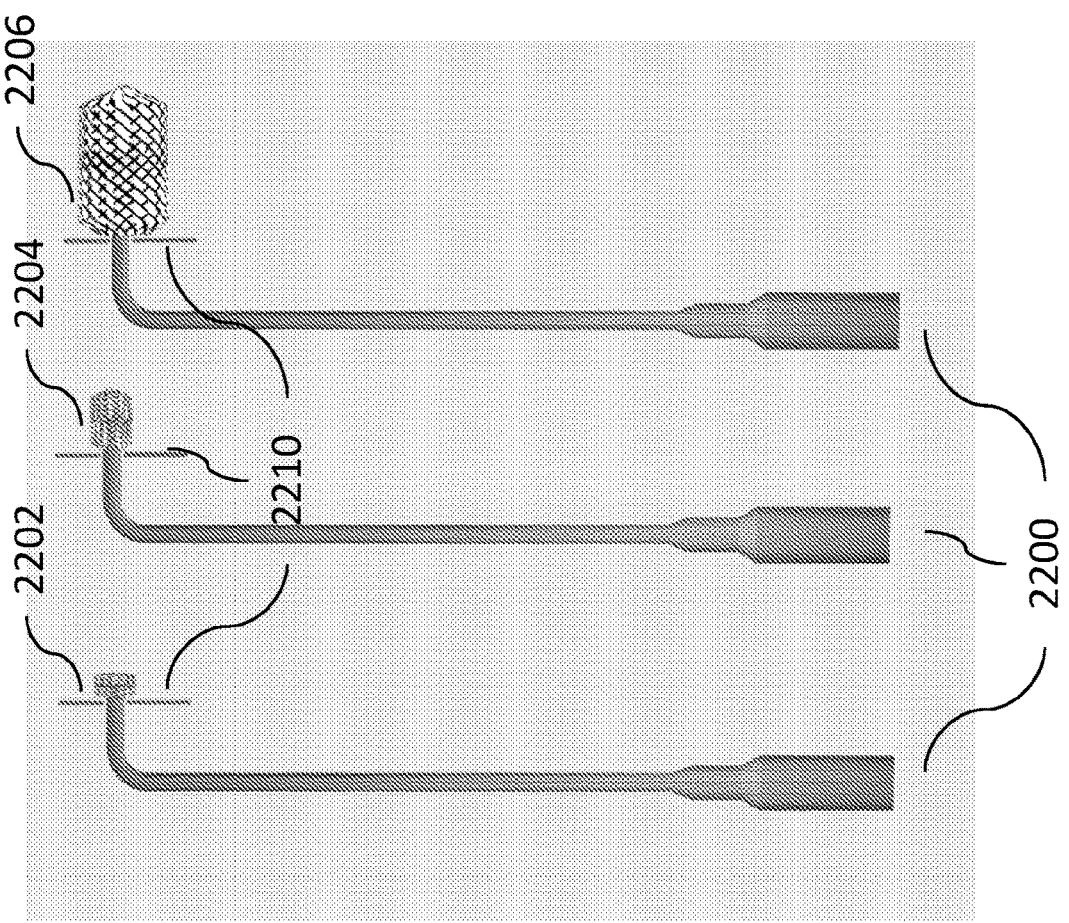
FIG. 22 illustrates an exemplary stabilization of a cannula tip, according to some implementations of the current subject matter.

FIG. 22 illustrates an exemplary stabilization of a cannula tip, according to some implementations of the current subject matter. As shown in FIG. 22, the cannula 2200 can include a tip 2210. In some exemplary non-limiting implementations, the cannula 2200 can be stabilized in the left atrium of the heart. The stabilization can be optimized using specifically-shaped angulated catheters (as shown by the curved cannulas 2200 in FIG. 22) in combination with different basket sizes (e.g., small size 2202, intermediate size 2204, large size 2206, and/or any other size). In some implementations, larger baskets can be used to prevent collapse of the left atrium in some cases.

In some implementations, the stabilizing and/or locking mechanism can be further enhanced by using various basket shapes, as shown in FIGS. 23a-c. As shown in FIG. 23a the shapes can include at least one of the following: a bulb, a ball, a cylinder with round, an oval, an asymmetric shape, a triangular shape, a square shape, a pentagonal shape, a hexagonal shape, a heptagonal shape, an octagonal shape, and/or any other shape, etc., base, profile and/or shape, pyramid, cone, double cone, inverted cone, inverted double cone, bell shape, in single, dual, multiple layers, single or multiple, uni- and/or multidirectional folds, plications, forming an inverted tulip-like structure or a tulip-like structure with a single or multiple small or large distal opening(s) etc., and/or optimized hoop strength of the cannula itself and the basket zone in uniform and or asymmetric fashion, and/or any other shapes and/or sizes. As shown in FIG. 23a, various geometric configurations of the cannula basket can be designed for tip stabilization using locking and/or friction mechanism. In some implementations, the cannula body and/or the cannula basket can be covered with a coating 2312 (e.g., a watertight coating that can be partially and/or fully made from a watertight material, and/or a permeable coating, a semi-permeable coating, and/or any other coating), as shown in FIG. 23b.

In some exemplary implementations, for trans-venous femoral access, a self-expanding cannula basket tip which can be larger than the vena cava can be stabilized in the right atrium, the right ventricle and/or the pulmonary artery and drain and/or perfuse the respective cardio-vascular section in a reversible fashion. After trans-septal insertion, the cannula tip can also be stabilized in the left atrium, in the left ventricle or in the aorta and thus, can be used to preferentially drain and/or inject arterialized blood. Taking advantage of the trans-septal routes (atrial and/or ventricular), any access vessel of sufficient size can be used to reach any target compartment of the cardio-vascular system and allow for cannula tip stabilization with the passive locking mechanisms described herein and/or the active locking mechanisms described below. Passive locking mechanism can be designed in a reversible and/or irreversible fashion.

FIG. 23c illustrates a three-dimensional view 2310 of the various baskets shown in FIG. 23a. The baskets can include braids having variable configurations, which can be based on use of shape memory materials. In addition to size and expansion force, specific stiffness of the basket braid sections can allow for adjustment of forces that may be required for cannula tip migration and/or expansion in situ.

Inventor of the current subject matter experimentally ascertained forces that may be required for cannula tip migration locked by an oversized basket in a cavity larger than the access diameter on a traction bench. FIG. 24 illustrates exemplary lower claws 2400 of a traction bench with a braided cannula 2410 having a relatively narrow 24 F body covered with a watertight plastic coating, which is inserted through a 24 F orifice. The basket in the space below opens up to size of 36 F. For comparison purposes, a straight 24 F cannula without basket expansion was also studied on the traction bench with the same parameters. FIG. 25 illustrates exemplary traction curves 2500 for the straight 24 F cannula pulled through the 24 F orifice. A mean load of 0.177±0.0129 N was required for 50 mm of distance. In contrast, for the 24 F cannula with the 36 F basket, a mean load of 0.759±0.041 N was required over a distance of 25 mm (as shown by the exemplary plot 2600 in FIG. 26), which is equivalent to 429% of the load measured for the straight control cannula (as shown by the exemplary plot 2700 in FIG. 27). FIG. 27 illustrates a difference in load that may be required for displacement of a straight 24 F cannula through a 24 F orifice versus a 24 F cannula with a 36 F basket through a 24 F orifice ($p<0.01$).

B. Active Locking Mechanism

FIGS. 28-32 illustrate an exemplary cannula having an active locking mechanism, according to some implementations of the current subject matter. Insome exemplary implementations, an active locking mechanism can be based on either an irreversible shape change of the basket due to specific stiff basket zones and/or less stiff basket zones, additional features like hooks, screws, VELCRO®, or an additional remote release mechanism that can be irreversible and/or reversible. As an example, a self-expanding cannula and its basket at the tip can be stretched with a mandrel for insertion over a guide wire. Once the cannula basket at the tip is in the target location (e.g., a vessel), the mandrel can be withdrawn and the cannula basket can open as discussed above as well as, as shown in FIG. 28, in a three-dimensional view of the braids with variable tip configurations.

Figure 28:
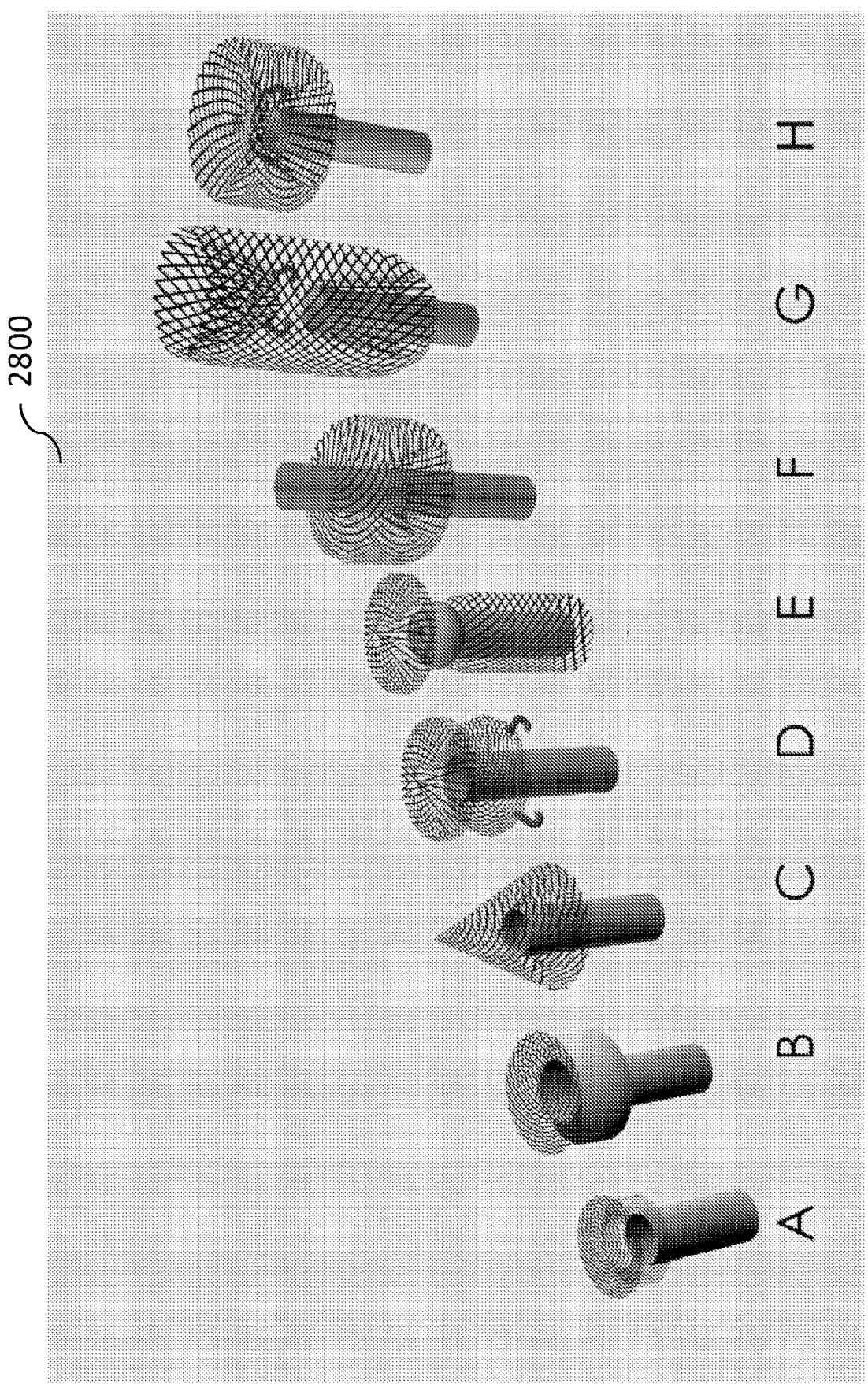
FIG. 28 illustrates basket configurations for reversible and/or irreversible locking, according to some implementations of the current subject matter.

FIG. 28 illustrates basket configurations 2800 A-H for reversible and/or irreversible locking, according to some implementations of the current subject matter. Configuration 2800(A) shows an exemplary basket with a waist. Using this configuration, extraction can require straightening of both basket compartments. Configuration 2800(B) illustrates an exemplary basket with a waist covered with watertight plastic and/or other stiffening materials. In this case, extraction with a covered section below the waist can require more force as compared to an uncovered configuration. The watertight coating can assist in sealing the cannula tip against the orifice. Additionally, the lower portion of the configuration 2800(B) can be coated; however, it can also be a balloon expandable section that can be inflated (e.g., using gas, liquid, etc. which may or may not harden).

Configuration 2800(C) illustrates an exemplary basket with a cone shape on top and a negative cone shape at the bottom. Here, extraction of this shape can require more load than a simple "olive" type basket. Configuration 2800(D) illustrates an exemplary larger dual basket as compared to the basket shown in configuration 2800(A). In this case, the basket can include additional anchoring hooks, barbs, spines, pins, etc. for irreversible stabilization in the target zone. If these additional anchoring hooks, barbs, spines, pins, etc. are designed in a retractable fashion, the attachment mechanism can be made reversible. Configuration 2800(E) illustrates an exemplary dual lumen design with a distal basket that can be placed in the left atrium (e.g., for injection) and a proximal additional lumen (e.g., for drainage) based on the braided, virtually wall-less cannula design, which may or may not be covered in part with a water-tight plastic. The tip of the proximal outer cannula can be fixed at a predetermined distance from the distal basket and assist in sealing the orifice in a trans-septal configuration. Further, the base of the distal basket may or may not be covered with a watertight plastic, cloth or other coverage in order to improve the seal at the orifice. Alternatively, the outer cannula can be advanced and/or retracted in an axial direction in order to squeeze the septal wall for additional sealing. This latter function can also be achieved using a spring mechanism, where the outer cannula can be advanced spontaneously towards the basket.

Configuration 2800(F) illustrates an exemplary basket that is disposed at a predefined distance (0 mm-X cm) from the cannula tip and can keep its orifice at a specific position. Configuration 2800(G) illustrates an exemplary basket that can include two inverted inner cones. The distal inner cone of the basket can have hooks and/or other appropriate means, e.g., an adjustable ratchet-type connecting system, for capture of the proximal basket. Configuration 2800(H) illustrates an exemplary two-basket configuration, where if the two baskets of this configuration are pulled together, the hooks of the distal basket can trap wires of the proximal basket and thus, the shape change can be become irreversible.

Figure 29:
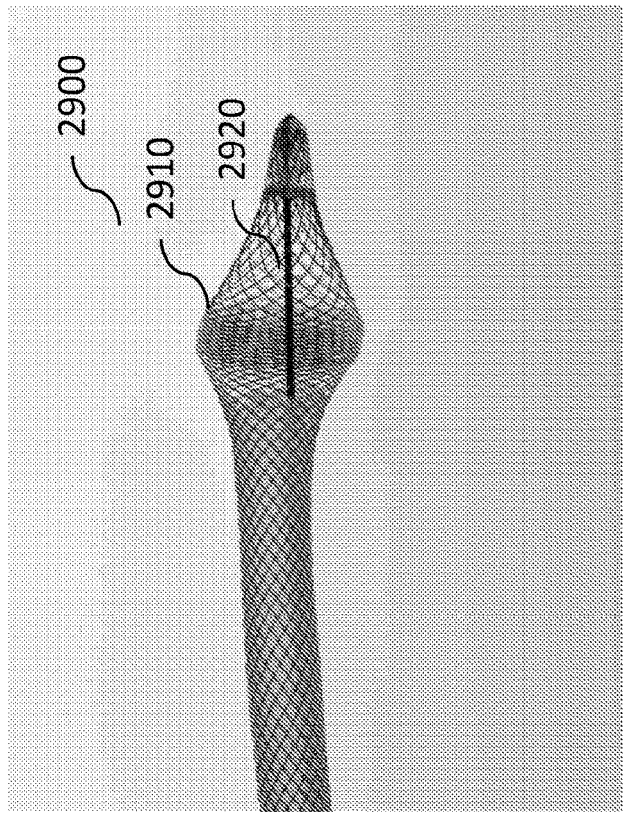
FIG. 29 illustrates an exemplary cannula having a basket and a locking wire that can allow for pullback of the cannula tip, thereby, enlarging the basket diameter, according to some implementations of the current subject matter.

In some implementations, the opened basket at the cannula tip can also be locked in the expanded position by a string, which can connect the cannula tip to the cannula sleeve. As long as the string is holding the cannula in the short configuration, the cannula basket cannot be collapsed and thus, can hold the cannula tip in the target zone. Similar mechanism can be used using a wire connecting the cannula tip to the cannula sleeve (as shown in FIG. 29). This locking wire may or may not be incorporated in the braid. FIG. 29 illustrates an exemplary cannula 2900 having a basket 2910 and a locking wire 2920 (e.g., a string, a screw, a tube and/or any other connection) that can allow for pullback of the cannula tip, thereby, enlarging the basket diameter, according to some implementations of the current subject matter. If the locking wire is securely attached to the cannula base, the basket cannot be collapsed anymore.

Figure 30:
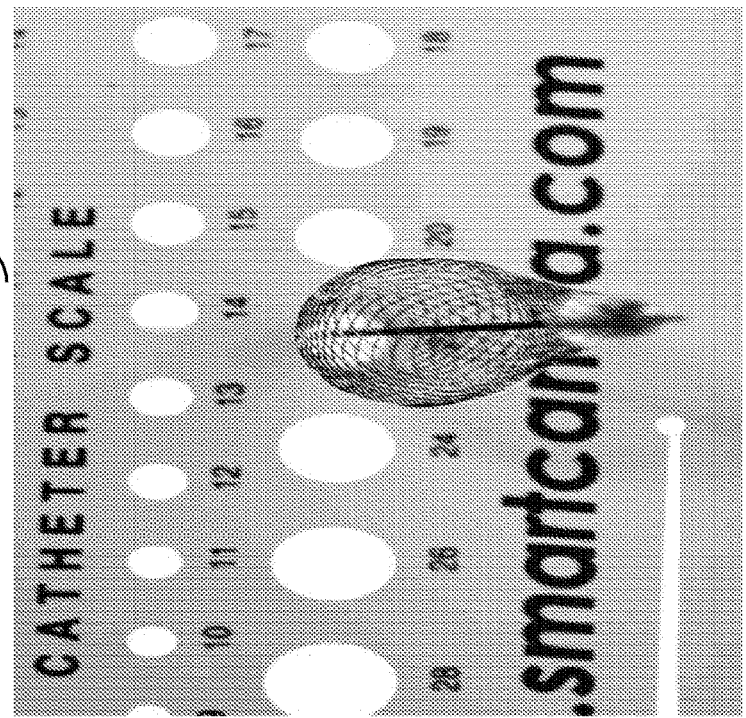
FIG. 30 illustrates an exemplary 24 F cannula with a 36 F basket and a locking wire that can be inserted through a 22 F orifice, according to some implementations of the current subject matter.

FIG. 30 illustrates an exemplary 24 F cannula with a 36 F basket and a locking wire that can be inserted through a 22 F orifice. If the locking wire is under traction, the basket can no longer be collapsed, and thus, the cannula tip cannot be pulled through the orifice without damaging the orifice, the cannula, or both.

Figure 31:
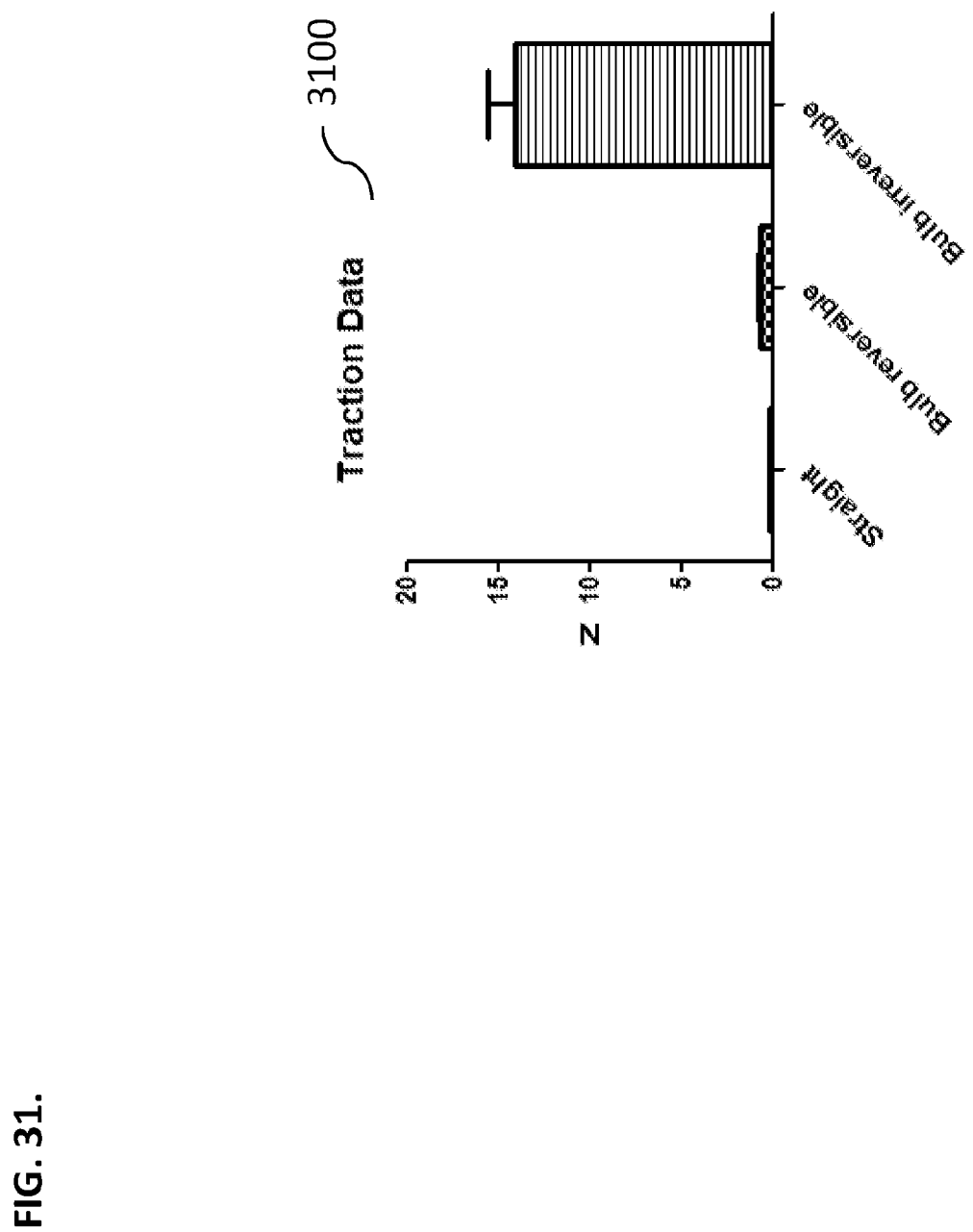
FIG. 31 illustrates an exemplary plot, according to some implementations of the current subject matter.

FIG. 31 illustrates an exemplary plot 3100 showing a comparison of the 24 F cannula with a 36 F basket (e.g., a bulb) that can be locked using a traction wire and that cannot be pulled through the 24 F orifice using a load of 14.11±3.27N. This force is 1859% of the load required to remove a cannula without a traction wire and 7971% of the load required for removal of a straight 24 F cannula.

The string, wire and/or any other locking mechanisms required for remote cannula and basket shortening can allow for remote control, adjustable control, reversibility, and/or any combination thereof. Other reversible and/or irreversible mechanisms can include tip retraction/inversion with removable strings, detachable wires based on screws, zip, key, bayonets, and/or other releasable systems including electrolytic separation with and/or without additional lock consolidating features like hooks, teeth, VELCRO®, irreversible shape change, etc. which may or may not be more suitable for permanent implantation.

In some implementations, the current subject matter cannula can include a dual lumen configuration. Dual lumen configurations with a locking and/or not locking basket for the inner catheter, with and/or without a similar locking and/or not locking basket configuration for the outer catheter can be used. Special designs can include an axially moveable basket for the inner, the outer and/or both catheters to secure the catheter position with reference to the intercavitary wall of the target cavity and/or a septum, e.g., atrial and/or ventricular or similar bodily structures which are not limited to the cardio-vascular system.

In some implementations, the current subject matter cannula can be implanted with and/or without guide wire. For the latter type implantation, a central channel can be used over the entire length of the cannula and the mandrel (co-axial design) or in case of a mono-rail system, only a (usually tip) section of the device can be designed for insertion over a guide wire the remainder of the device following the tip.

In some implementations, the current subject matter cannula can be manufactured (either partially and/or wholly) from shape memory materials including nitinol, elgiloy, etc. and/or plastics with similar characteristics molded and/or injection molded as one piece or multiple components co-extruded and/or assembled in sequential fashion including braids with or without watertight coverage (see previous patents) and with or without connecting fittings.

In some implementations, various techniques can be used for diameter reduction (collapsing) prior insertion and re-expansions in situ. This can include a braided configuration discussed above which can be stretched and/or collapsed simultaneously for the entire cannula if the plastic used for coverage is elastic, and/or part of it. Thinner wires and/or softer wires and/or softer plastic can be used for segments which are intended for preferential reduction of the diameter. Similar effects can be achieved by twisting and/or furling the device or parts of the device in order to unfurl it once it is in position. Further, a sheath, and/or a split sheath, which can be retracted and or removed, once the cannula, and/or its tip is in position, can be used (as shown in FIGS. 33a-39 and discussed below). Compression with a removable string and/or a removable cloth or envelope can be also used. Further, the basket and/or the cannula can be constructed completely and/or partially with hollow compartments that can be inflated for shape change with a gas or a fluid (reversible) or a hardening fluid (irreversible). Other activation modes of a spring loaded tip or segment can be based on a remote mechanical (possibly motorized), chemical, electrolytic, photosensitive, and/or thermo-sensitive (e.g. thermo-sensitive nitinol) segment holding the device in position during insertion.

In some implementations, the current subject matter cannula (e.g., basket at the cannula tip) can perform flow distribution and filtering. During perfusion, the basket can act as a jet dispersing device (which can be similar to the directional use cannulas as shown and discussed in connection with FIGS. 15a-e). As an example, the jet into free air for four (4) 1/min of flow with water through a 24 F cannula can be typically around 100 cm. In contrast, the basket type tip reduces the jet for the same flow to approximately 10 cm.

Figure 32:
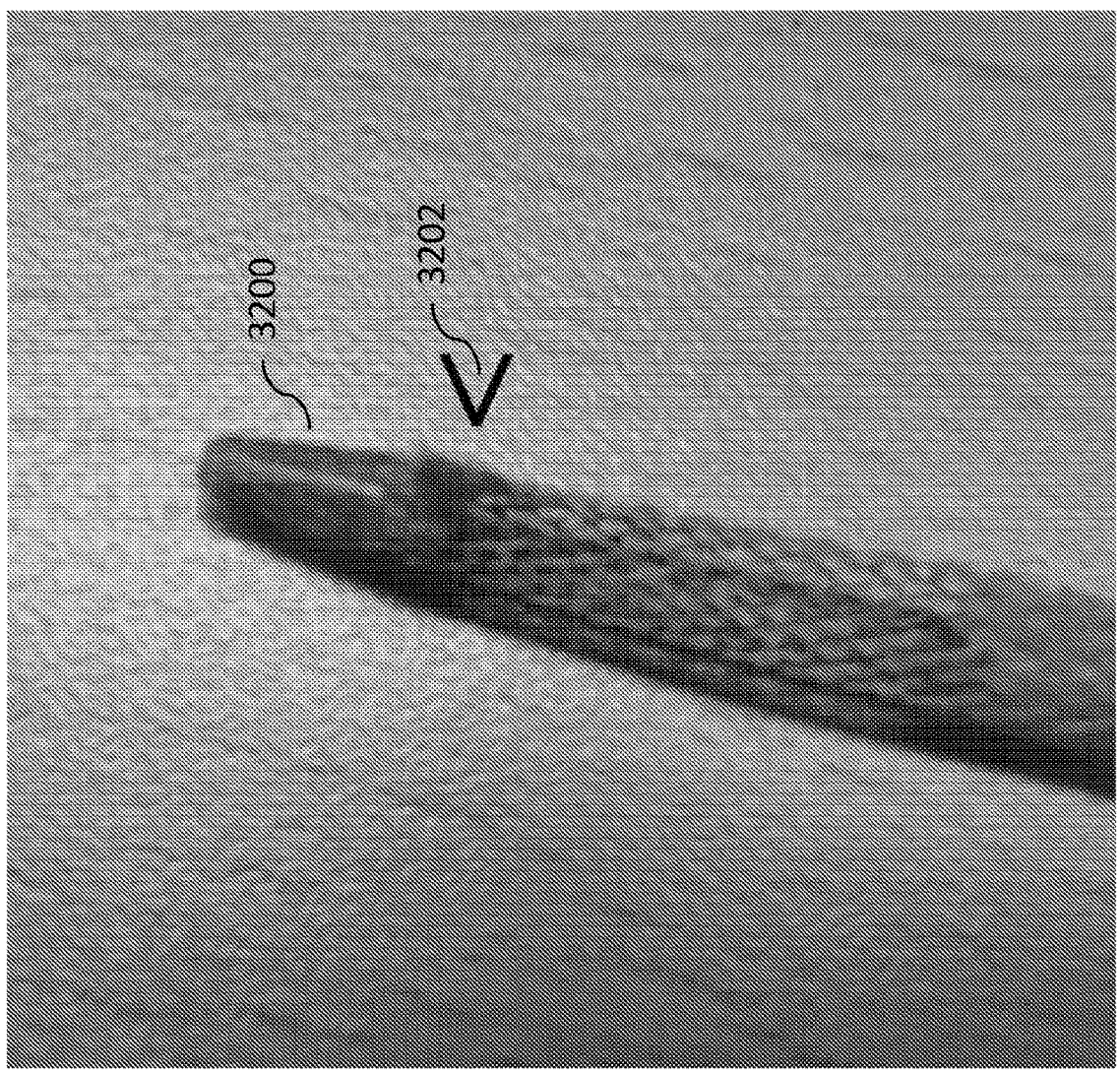
FIG. 32 illustrates an exemplary basket structure of the cannula tip, according to some implementations of the current subject matter.

Further, the basket structure of the cannula tip can capture foreign bodies in the pumped medium, as shown in FIG. 32. As shown in FIG. 32, basket type tip 3200 can act as filtering device: captured foreign materiel is visible (as shown by "<" 3202).

In some implementations, the current subject matter cannula can be an active locking cannula in combination with a pump. The locking cannulas discussed above can be combined with a pump indwelling in its distal, intermediate and/or proximal section. This combination can prevent cannula tip (i.e., pump inlet) displacement. In some implementations, the currents subject matter cannula can be used in hollow organs, e.g., biliary system, intestine, kidney, brain, solid organs after creation of a channel, e.g., liver, spleen, lung. It can be used in veterinary non-medical environment, e.g., technical applications where high cannula performance and targeted drainage and injection zones are critical.

IV. Self-Expanding Sheath

In some implementations, the current subject matter's self-expanding cannula can be used for a variety of cardio-pulmonary applications (e.g., cardio-pulmonary bypass, etc.) as well as other applications that are outside of cardio-pulmonary field. In some implementations, the cannula can be used as a sheath for introducing wires, catheters, devices, and/or any other objects and/or any combinations thereof into bodily cavities and/or solid organs within a body.

FIGS. 33a-e illustrate an exemplary cannula 3310 that can be used as a sheath for the purposes of introduction of objects into a body, according to some implementations of the current subject matter. For comparison purposes, FIGS. 33a-e also illustrate a conventional sheath 3350 that is typically used for introduction of objects. The conventional sheath 3350 typically includes a valve 3351 and has a rectilinear configuration of its body (center and left).

The current subject matter's self-expanding sheath 3310 can include a valve 3311, a covered central portion 3313, which will provide the seal, an uncovered portion 3312, and a tip 3315. An object can be advanced by entering through the valve 3311 (which can be coupled to other tubing (not shown in FIGS. 33a-e), then passed through the covered central portion 3313 and uncovered portion 3312 and exit at the tip 3315. The valve 3311 can also prevent any backflow of fluids in the event the sheath is introduced into a vessel having a high fluid pressure.

Figure 33B:
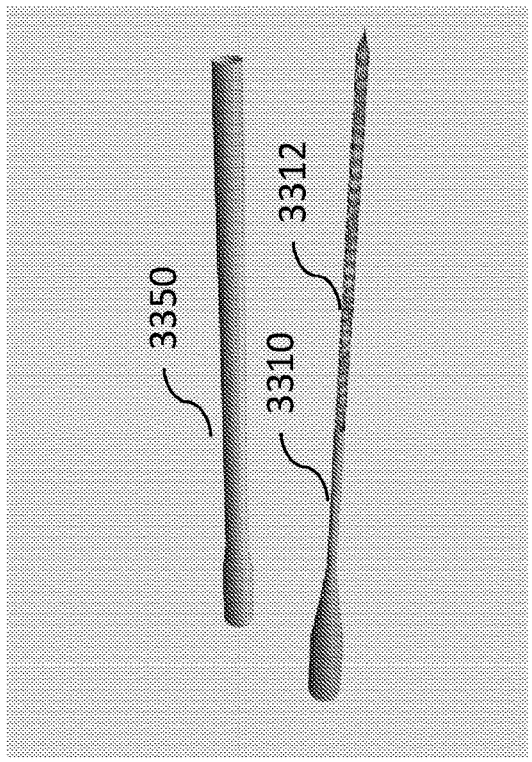
FIGS. 33a-e illustrate an exemplary cannula that can be used as a sheath for the purposes of introduction of objects into a body, according to some implementations of the current subject matter.

Prior to introduction of objects and prior to insertion of the sheath 3310 into a bodily organ (or cavity), the sheath 3310 can be collapsed (as shown in FIG. 33b). In the collapsed configuration, the sheath 3310 can be inserted through an access orifice and advanced to the target location (i.e., the bodily organ and/or cavity). In the collapsed configuration, one or both of the portions 3313 and 3312 as well as at least a portion of the tip 3315 can be collapsed (a fully collapsed sheath 3310 is shown in FIG. 33b).

Figure 33A:
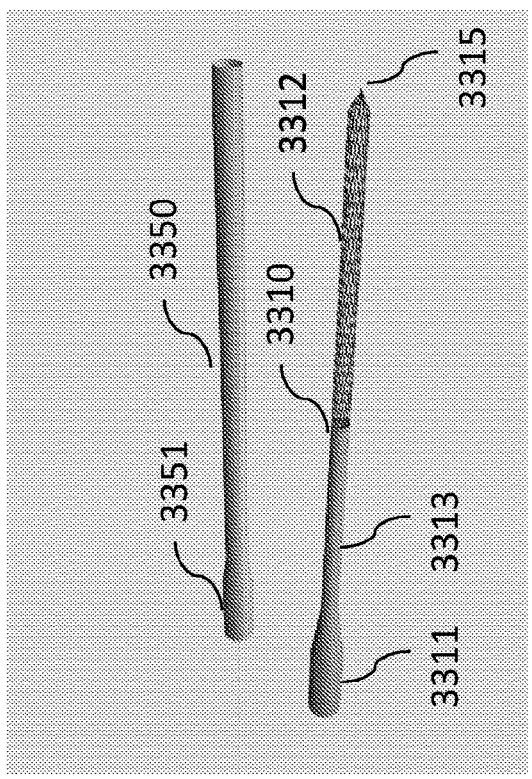

In the target location or in situ, the sheath 3310 can be expanded to a desired size (e.g., up to a surface of an interior wall of a vessel and/or any other size). The sheath 3310 can be expanded using a mandrel, a bougie, a balloon, a pressurization mechanism, a retraction mechanism, a releasable string, a split-sheath and/or any other suitable mechanism that can be coupled to the valve and/or using any other methods. Exemplary expansion/contraction mechanisms are disclosed in co-owned U.S. Pat. No. 8,992,455 to von Segesser, issued on Mar. 31, 2015, and entitled "Methods, apparatuses and systems for caval stenting for venous drainage," and co-owned U.S. Pat. No. 8,679,053 to von Segesser, issued Mar. 25, 2014, and entitled "High performance cannulas," the disclosures of which are reiterated and incorporated herein by reference in their entireties. An expanded configuration of the sheath 3310 is illustrated in FIG. 33a. By contrast, the conventional sheath 3350 is unable to contract or expand, thereby requiring large access orifices and/or large bodily channels for advancement. In the expanded configuration, the sheath 3310 can allow passage of wires, catheters, devices, and/or any other objects and/or any combinations thereof into bodily cavities and/or solid organs within a body, where such devices can have a larger size and/or diameter than the diameter of the sheath 3310 in the collapsed configuration.

Figure 33C:
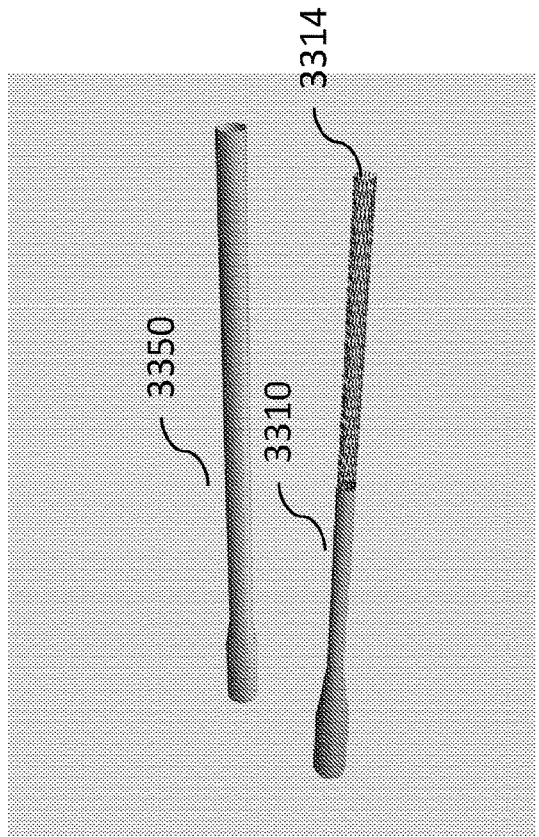
Figure 33E:
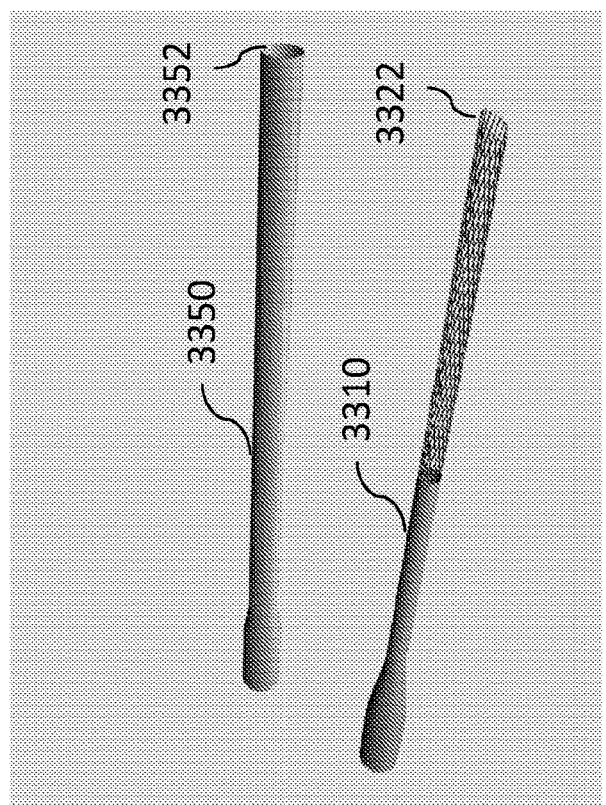
Figure 33D:
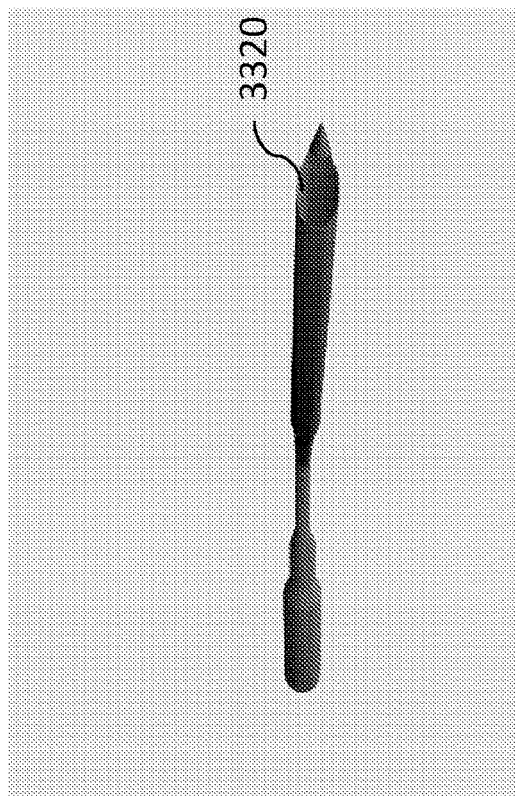

In some exemplary implementations, the self-expanding sheath 3310 can be manufactured at least in part from shape memory materials (e.g., nitinol and/or other metallic and/or synthetic materials). One or more portions of the sheath (e.g., portion 3313 and/or valve 3311) can be covered by a suitable material (e.g., plastic and/or any other materials). The covered portions can be disposed outside of the body. Additionally, the sheath may or may not include a valve that can prevent backflow if the sheath is inserted in a pressurized vessel and/or prevent aspiration if the sheath 3310 is inserted in a hollow body with a negative pressure. The uncovered part can be designed to be disposed in the target location (e.g., a lumen, an intravascular part, etc.). Further, the target vessel that receives the sheath can provide a seal, thereby no cover (e.g., plastic cover or any other cover) of the portion 3312 may be necessary. In some implementations, the sheath 3310 can include one or more orifices that can be disposed proximate to the tip 3315 (e.g., orifice 3314 as shown in FIG. 33c, orifice 3320 as shown in FIG. 33d, orifice 3322 as shown in FIG. 33e). The sheath 3310 can have any number of orifices, which can have any shape, size, etc. The orifices can be included in the sheath depending on a particular use of the sheath 3310.

In particular, FIG. 33d illustrates a sheath having a large orifice 3320, which can allow passage of large objects and/or devices despite the concentric self-expanding tip. The self-expanding nature of the sheath can allow the access orifice and the access vessel to have a small diameter, which can allow passage of the sheath in a collapsed state, whereas the lumen of the target vessel and/or the target hollow organ can be much larger. Thus, the sheath can provide sufficient space for passing a large object/device close to the tip. FIG. 33e illustrates an oblique section 3322 of the tip. This exemplary implementation can allow increasing the distal tip orifice circumference as compared to the cannula diameter, thereby allowing for larger objects/devices to pass without increased resistance.

Figure 34A:
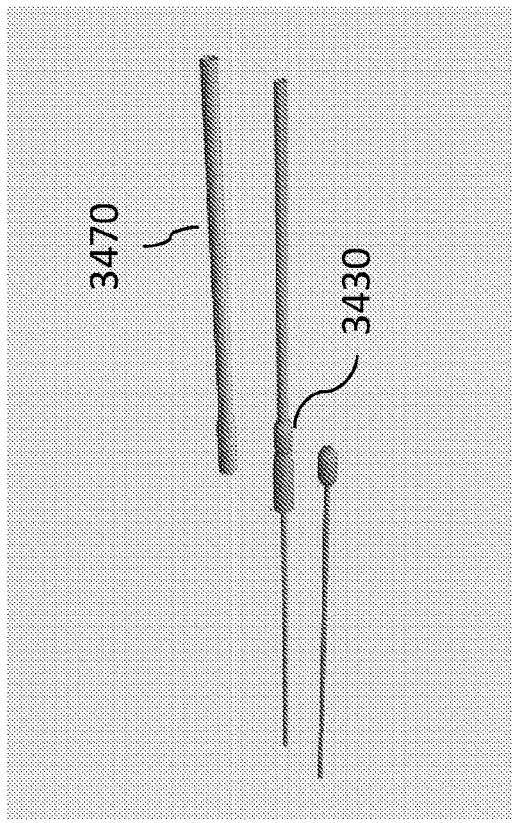
FIGS. 34a-d illustrate an exemplary passing of an object through the self-expanding sheath, according to some implementations of the current subject matter.
Figure 34B:
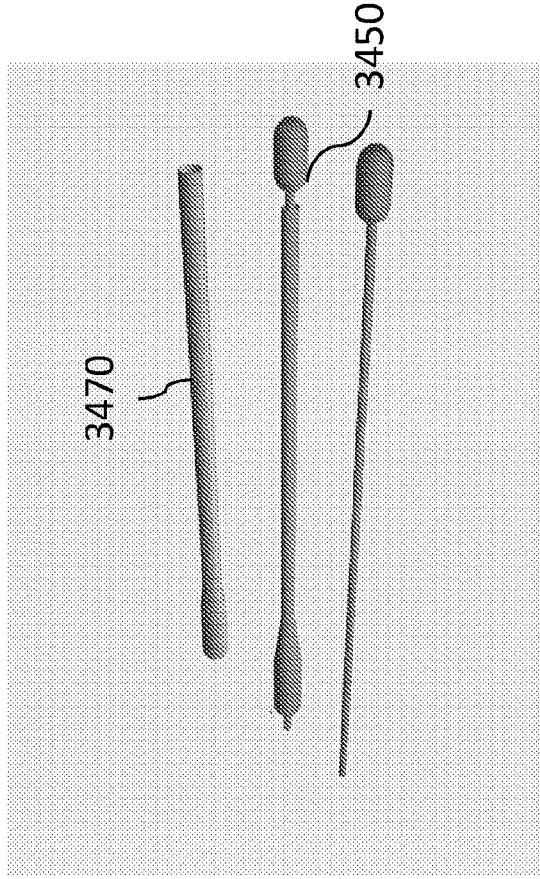
Figure 34C:
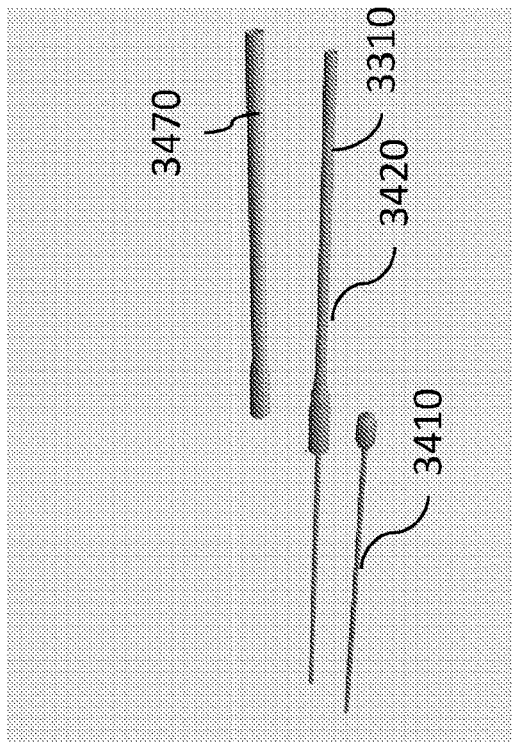
Figure 34D:
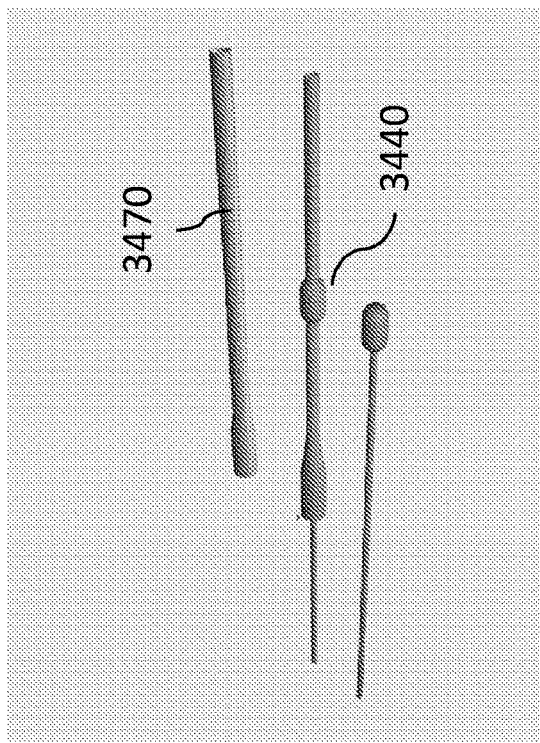

FIGS. 34a-d illustrate an exemplary passing of an object through the self-expanding sheath 3310 (as shown in FIG. 33a), according to some implementations of the current subject matter. As shown in FIGS. 34a-d, the self-expanding sheath 3310 can allow for passing of objects/devices, which can have a larger diameter than the nominal diameter of the expanded sheath 3310. A conventional introducer 3470 is also shown in FIGS. 34a-d for comparison purposes. As shown, the conventional introducer 3470 is unable to accommodate passage of an object/device 3410 in view of its size. The sheath 3310's expandable structure and/or an elastic coating that can allow for such passing. As shown in FIG. 34a, the sheath 3310 can accommodate insertion of the object/device 3410, where, at 3420, the object 3410 is shown being inserted into the sheath 3310 through its valve section. FIG. 34b illustrates, at 3430, the object 3410 being advanced through the sheath 3310 and into its covered section. In some implementations, the valve of the sheath 3310 can accommodate insertion of objects/devices that have a diameter larger than the nominal diameter of the self-expanding sheath. FIG. 34c illustrates, at 3440, the object 3410 being advanced trough the self-expanding section of the sheath 3310. Due to its self-expanding nature, the self-expanding section of the sheath can easily accommodate advancement of the object 3410 through the sheath 3310. FIG. 34d illustrates, at 3450, the object 3410 existing from the tip of the sheath 3310 and into the target location (not shown in FIG. 34d). The object can pass through an orifice that may be concentrically located with the tip (or in the tip) and/or any other orifice that may be disposed proximate to the tip of the sheath 3310.

Figure 35B:
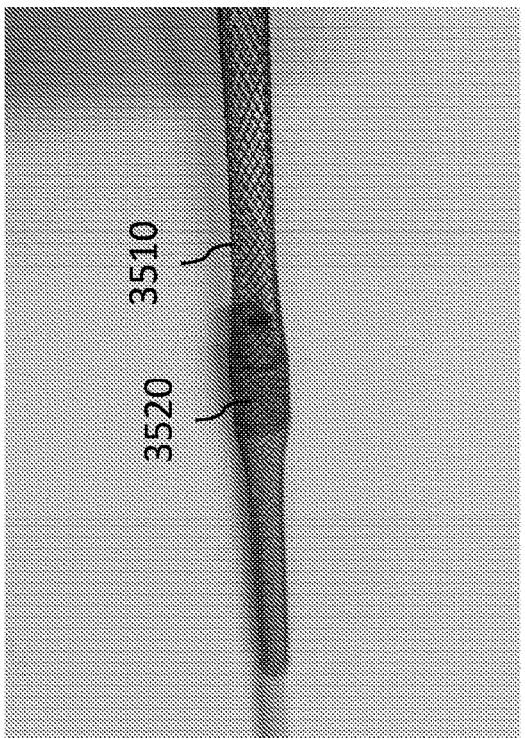
FIGS. 35a-c illustrate an exemplary self-expanding sheath having at least one of its sections being partially and/or fully covered, according to some implementations of the current subject matter.
Figure 35A:
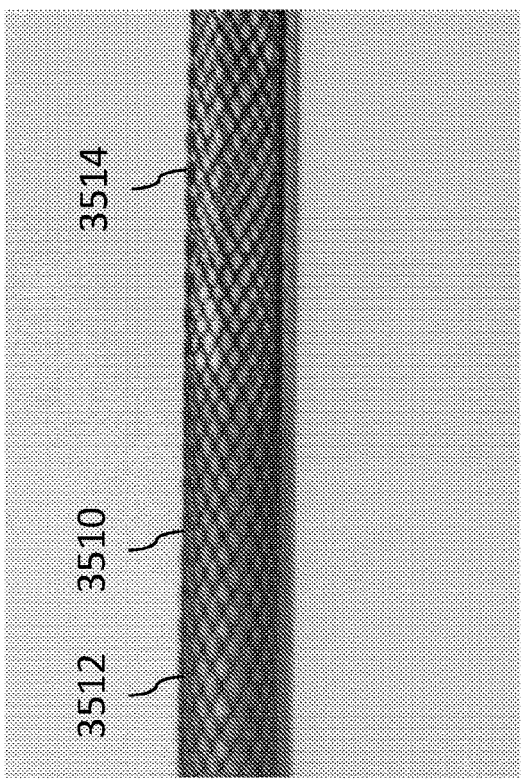
Figure 35C:
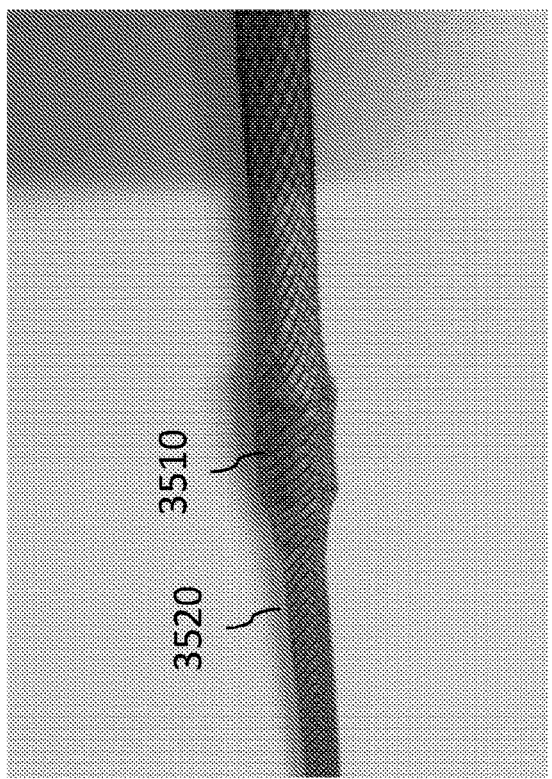

FIGS. 35a-c illustrate an exemplary self-expanding sheath having at least one of its sections being partially and/or fully covered, according to some implementations of the current subject matter. FIG. 35a illustrates an exemplary self-expanding sheath 3510 having a covered section 3512 and an uncovered section 3514. The sheath 3510 can be similar to the sheath 3310 shown in FIGS. 33a-33e. The sheath body can be covered completely and/or partially. The cover can be at least one of the following: a watertight coating, a porous coating, a semi-permeable coating, a permeable coating, and/or any other coating, a plastic cover, a metallic cover, a synthetic material cover, and/or any other desired cover, and/or any combination thereof. In some exemplary implementations, the cover may be required for a section of the self-expanding sheath when the sheath is used in pressurized applications at the point of insertion and/or outside of the body, whereas within the target vessel lumen and/or the target hollow organ the coverage might not be necessary.

FIG. 35b illustrates an exemplary self-expanding sheath 3510 having an uncovered section with a dilator 3520 being passed through it. In some exemplary implementations, the sheath 3510 can be an 18 F self-expanding sheath and the dilator 3520 can be an 18 F dilator with a 30 F hub, which can represent a larger object/device being passed through the sheath 3510 with smaller nominal diameter in expanded configuration. The insertion diameter of the self-expanding sheath can be smaller (e.g., 12 F). FIG. 35c illustrates an exemplary sheath 3510 having a covered section and a dilator 3520 being passed through it. The sheath can be an 18 F self-expanding sheath and the dilator can be an 18 F dilator with a 30 F hub, which can be the larger object/device passing through the sheath 3510 having a smaller nominal diameter in an expanded configuration. Similar to FIG. 35b, the insertion diameter of the self-expanding sheath 3510 can be even smaller (e.g., 12 F).

Figure 36A:
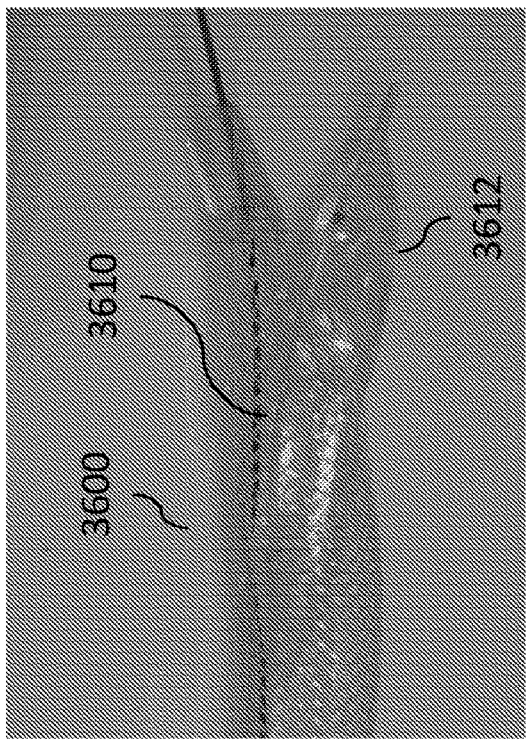
FIGS. 36a-c illustrate exemplary self-expanding sheath having variable elastic and/or non-elastic properties, according to some implementations of the current subject matter.
Figure 36B:
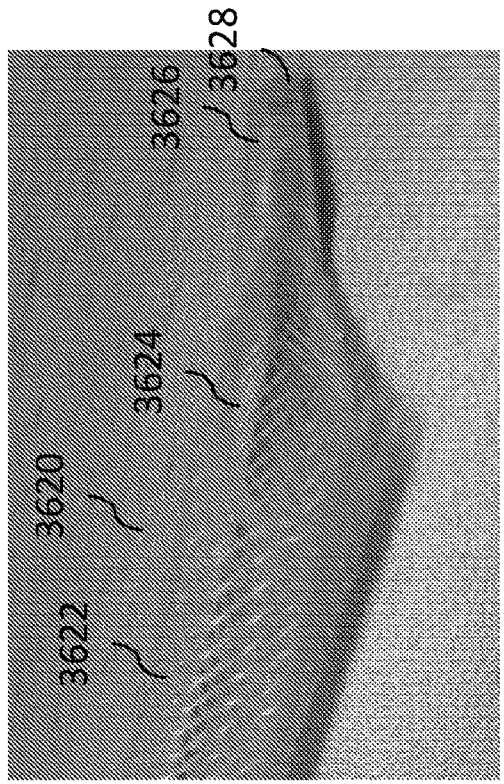
Figure 36C:
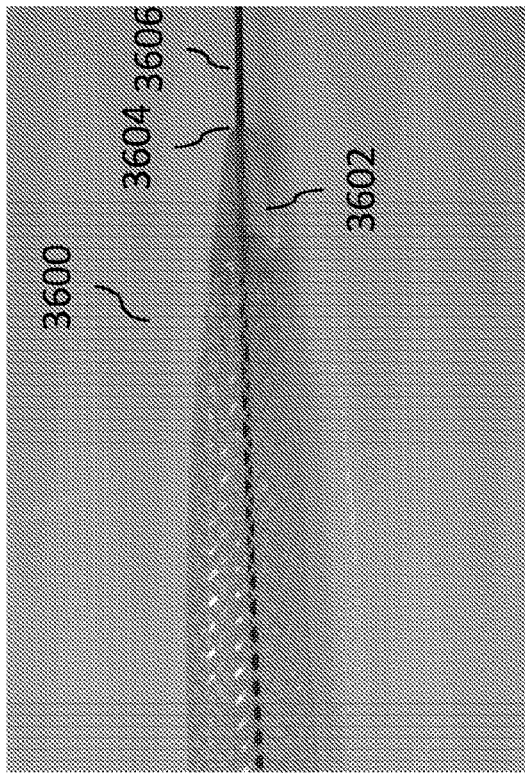

In some implementations, the self-expanding sheath and/or any its portions can be manufactured from various materials that can have various elastic and/or non-elastic properties. The materials can include at least one of the following: metallic wire(s), synthetic fiber(s), natural fiber(s), hollow fiber(s), woven, knitted, laced, interwoven, sealed, unsealed, materials, etc. and/or any combination thereof. Additionally, specific coatings can be applied, which can be used to change one or more physical properties of the sheath (e.g. lubrication, etc.), one or more mechanical or structural properties of the sheath, one or more pharmaceutical properties of the sheath (e.g., for thromboresistance, etc.), one or more chemical properties of the sheath, and/or any other properties of the sheath, and/or any combination thereof. In some exemplary implementations, the sheath can have one portion having greater elasticity and/or rigidity than other sections of the sheath. FIGS. 36a-c illustrate exemplary self-expanding sheath 3600 having variable elastic properties. As shown, the self-expanding sheath can have an 18 F tip 3602 and can be collapsed and can be expanded to 45 F. The sheath has an orifice 3604 at the tip 3602, which can accommodate insertion of a coaxial guidewire 3606 that allows feeding the sheath 3600 over it for insertion into a body. FIG. 36*b* illustrates that the sheath 3600 can have an orifice 3610, which can be created using dilatation of a portion of a surface of the sheath 3600 using a balloon 3612. Once the orifice is created, an object 3614 can be passed through it, as shown in FIG. 36*c*. Here, the object can be a 36 F bar, where the self-expanding sheath can have a 12 F tip and an expanded diameter of 45 F.

Figure 36D:
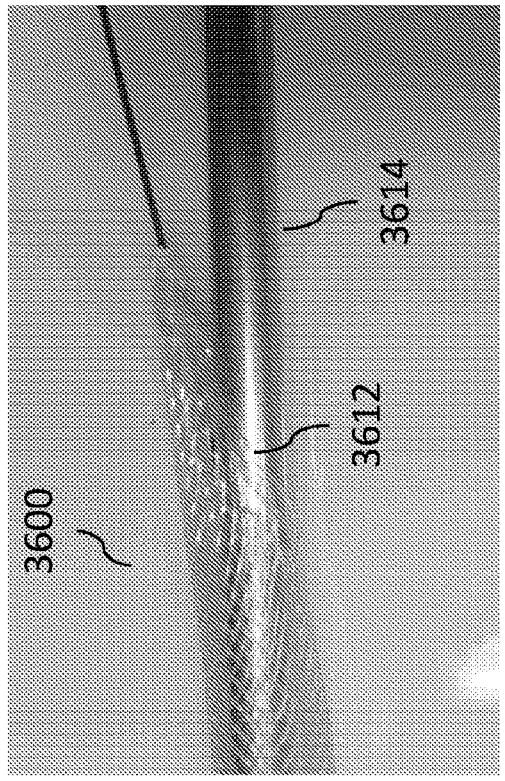
FIG. 36d illustrates an exemplary self-expanding sheath having a concentric orifice, according to some implementations of the current subject matter.

FIG. 36*d* illustrates an exemplary self-expanding sheath 3620, according to some implementations of the current subject matter. The self-expanding sheath 3620 can include a sheath body 3622, a concentric orifice 3624 (which can be a large concentric orifice), and a tip 3626. The orifice 3624 can be proximately located to the tip 3626. The tip 3626 can be an excentric tip and can include a channel 3628, which can allow para-axial insertion of an object/device, e.g., a guide-wire (e.g., mono-rail, etc.), a mandrel, and/or any other objects/devices. In some exemplary implementations, instead of being a self-expanding sheath 3620, a self-expanding cannula can have a similar elements and/or structure shown in FIG. 36*d*. The structure of the cannula/sheath 3620 can be used in various applications (e.g., arterial and/or any other applications as discussed herein) for providing a relatively straight exit flow and delivery of objects/devices without affecting and/or conflicting with the tip 3626.

Figure 37:
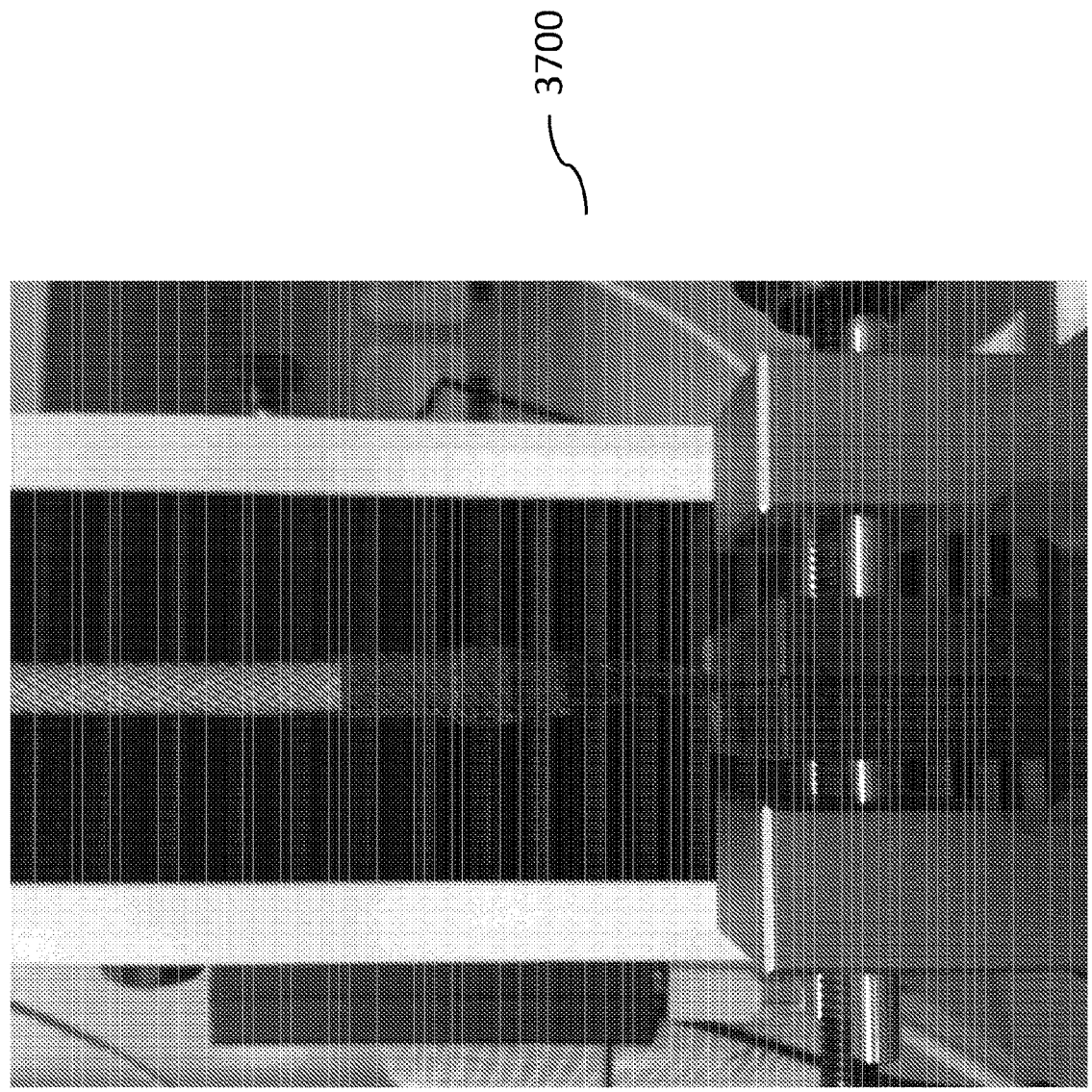
FIG. 37 illustrates a calibrated traction/compression bench.
Figure 38:
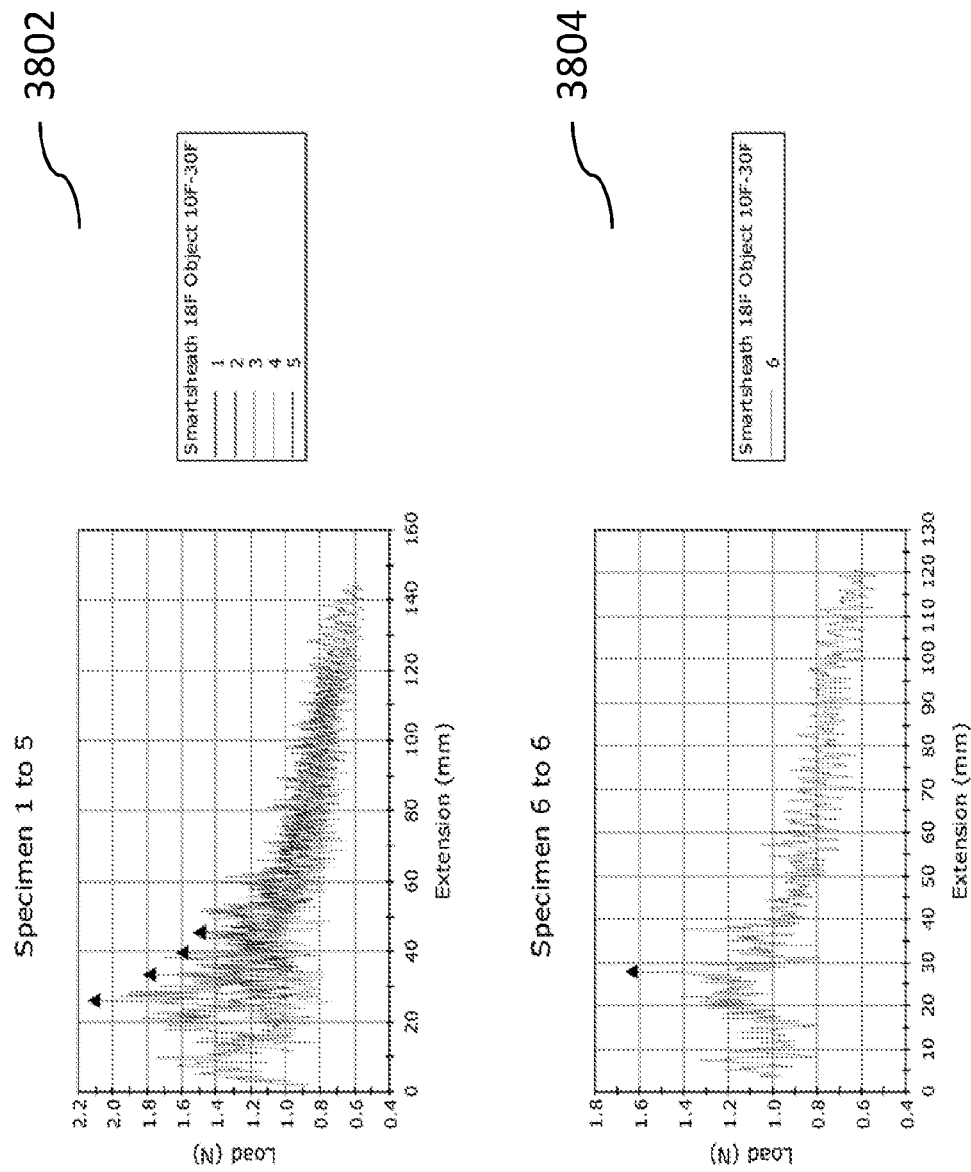
FIG. 38 illustrates exemplary experimental plots, according to some implementations of the current subject matter.

In some exemplary, experimental implementations, the forces that may be required for passing an object/device larger than the nominal diameter of the self-expanding sheath can be measured using a calibrated traction/compression bench 3700, as shown in FIG. 37. Here, a 10 F mandrel with a 30 F hub can be pulled through an 18 F self-expanding sheath. FIG. 38 illustrates exemplary experimental plots 3802 and 3804 showing traction curves for insertion of a 30 F hub mounted on a 10 F dilator through a non-optimized uncovered section of an 18 F self-expanding sheath, as shown in FIG. 37. The plots 3802 and 3804 illustrate that low forces around 1.7±0.2 N are required in reproducible fashion.

Figure 39:
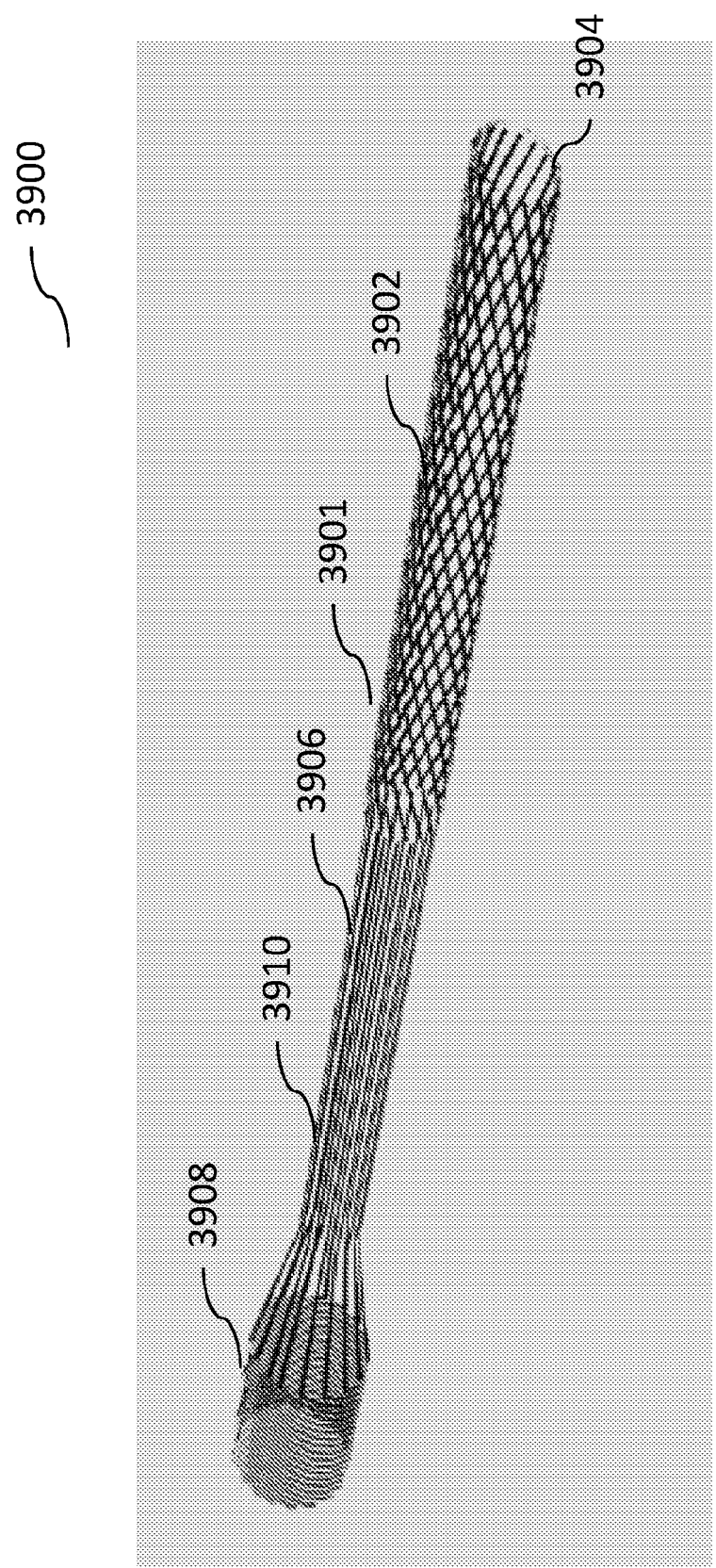
FIG. 39 illustrates an exemplary self-expanding sheath, according to some implementations of the current subject matter.

FIG. 39 illustrates an exemplary self-expanding sheath 3900, according to some implementations of the current subject matter. The sheath 3900 can include a body 3901, an expandable portion 3902, a tip 3904, an upper portion 3906 and a hub 3908. The sheath 3900 can be expandable and/or collapsible using an expanding mechanism (not shown in FIG. 39). The sheath 3900 can be manufactured using materials having elastic and/or non-elastic properties, e.g., nitinol, and any other suitable metals and/or plastics (e.g., the sheath can be manufactured from multiple components or laser/water jet cut from a single tube). In some implementations, the sheath 3900 can include passive and active mechanisms for enhancing/reducing the expansion force in some segments but not in others and/or throughout the entire sheath 3900. These include, but are not limited to, a traction mechanism, which can enlarge a braided structure 3902. The sheath 3900 can further include longitudinal traction members 3940 that can be disposed between at the tip 3904 of the sheath 3900 and the hub 3908. The longitudinal members 3910 can allow shortening/extending of the sheath. Shortening/extending a braided structure can results in an enlargement of its diameter and thus, the expansion force of a self-expanding device can be increased (in some cases, substantially). The longitudinal traction members 3910 connecting the tip 3904 and the hub 3908 can be arranged in separate layers inside, outside or interweaved with the expandable portion which may include part or all of the device length. Other means for local enlargement of the self-expanding sheath 3900 (e.g., within the channel of insertion) can include a suitable nose-cone for the object/device holder of the object/device to be advanced through the sheath, a step dilator, a balloon, and/or any other devices and/or any combination thereof. Further, the self-expanding sheath can include narrower (e.g., at the point of insertion) and larger (e.g., within the access and/or the target vessels) sections, as shown for example, in FIGS. 33*a-e*, and similarly, for the self-expanding cannula, as shown and described in FIG. 10*a*.

Figure 40B:
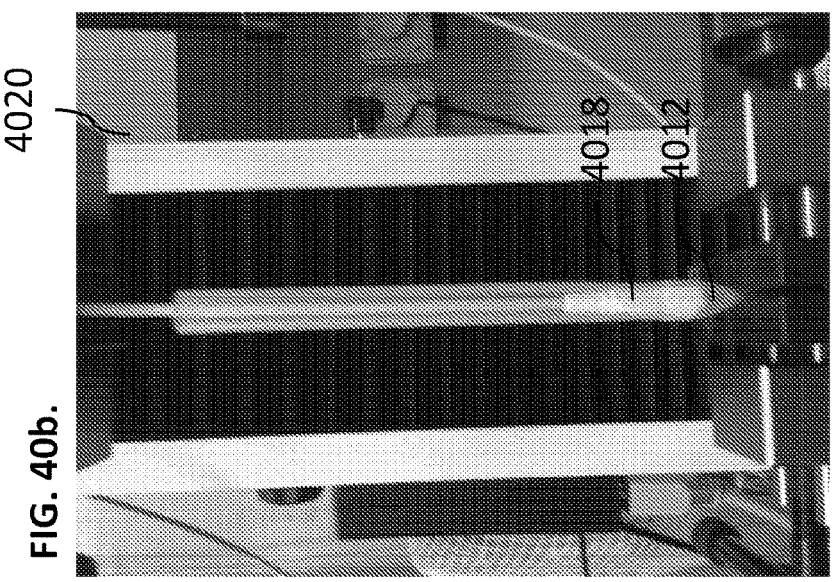
FIGS. 40a-c illustrate experimental use of a conventional rectilinear sheath.
Figure 40A:
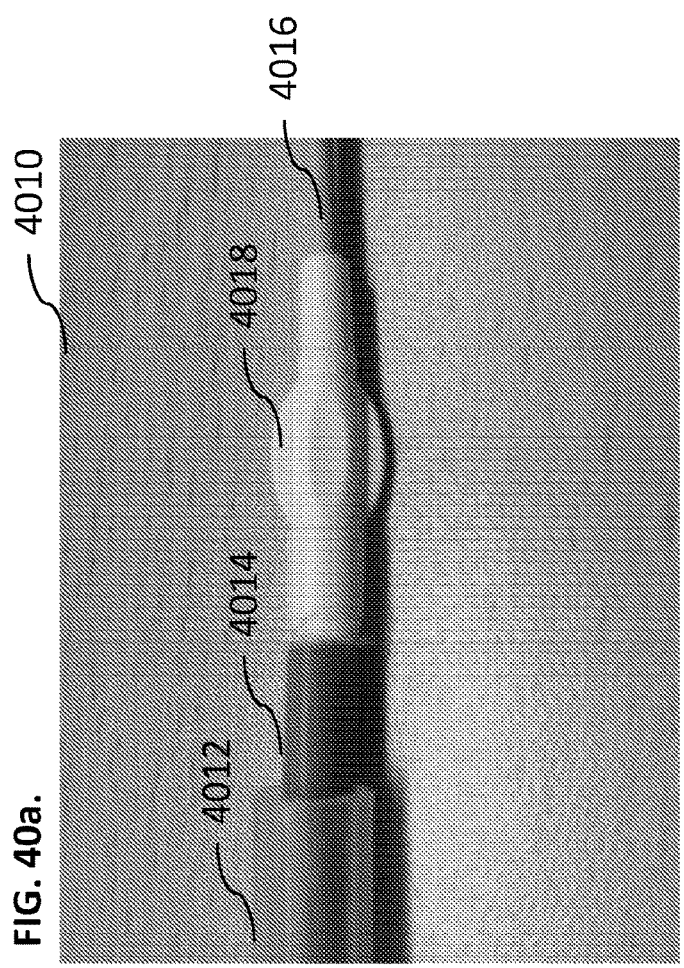
Figure 40C:
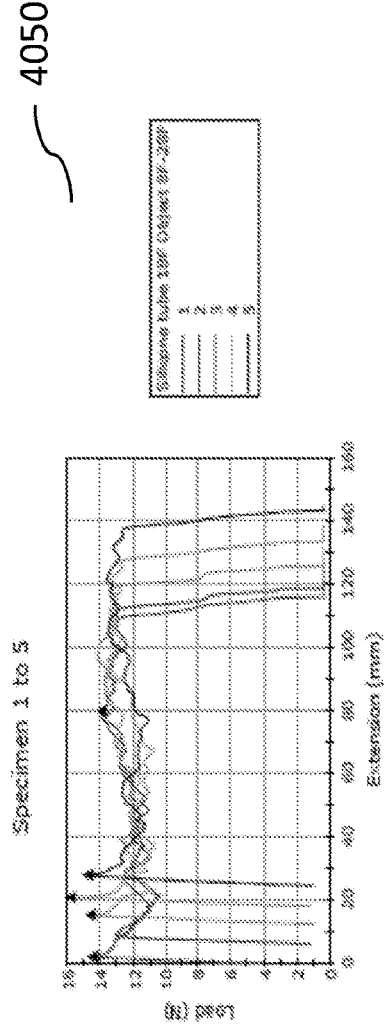
Figure 40C:
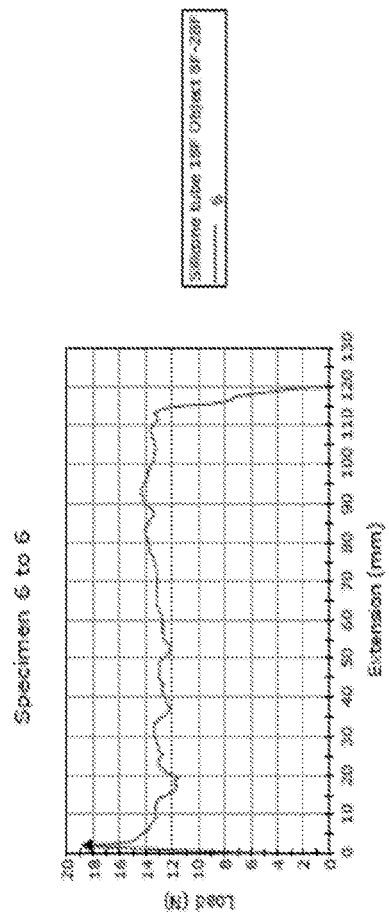

FIGS. 40*a-c* and 41*a-c* illustrate a comparison and various advantages of the current-subject matter's self-expanding sheath over the existing rectilinear sheaths. FIGS. 40*a-c* illustrate an apparatus 4010 that uses a conventional rectilinear sheath (as shown in FIG. 40*a*) and various experimental results (as shown in FIG. 40*c*) using traction bench (as shown in FIG. 40*b*).

Referring to FIG. 40*a*, the apparatus 4010 illustrates a conventional rectilinear sheath 4014 being inserted in a plastic tube 4012 (typically made from silicone) having an inner lumen measuring 18 F. The rectilinear sheath 4012 measuring 16 F (which is used for atraumatic insertion, where it is recommended to use a sheath one size below the luminal width) is inserted into the plastic tube 4012. The apparatus 4010 includes an 8 F dilator 4016 with a hub 4018 that passes through a 28 F orifice. Undoubtedly, it is impossible to pass the 28 F hub 4018 through the 16 F sheath 4012 without destroying the sheath 4012, the dilator 4016, the hub 4018, and/or the tube 4012. FIG. 40*b* illustrates a traction bench 4020 that was used to test the apparatus 4010. As shown in FIG. 40*b*, the traction bench 4020 is holding the tube 4012 (18 F lumen) and the 8 F dilator 4016 with the hub 4018 attempting to pass through a 28 F orifice. Clearly, the hub 4018 is larger than the luminal diameter of the tube 4012. FIG. 40*c* illustrates plots and a table 4050 showing forces that are required for traction of the hub 4018 through the tube 4012 with smaller diameter. As shown in FIG. 40*c*, the mean traction forces that are required to pull the 28 F hub 4018 through the 18 F tube 4012 over a distance of approximately 120 mm are on the order of approximately 15.33±1.66 N.

Figure 41A:
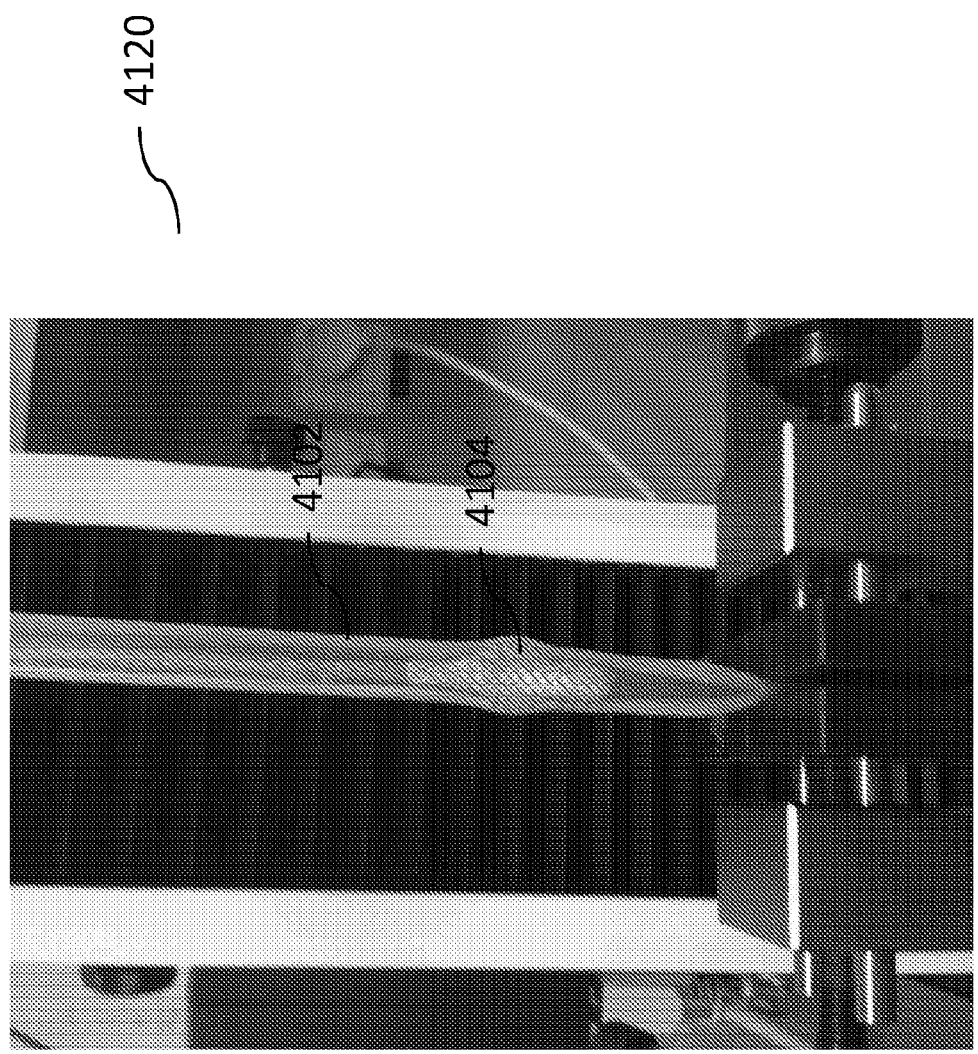
FIGS. 41a-c illustrate experimental use of a self-expandable sheath, according to some implementations of the current subject matter.
Figure 41B:
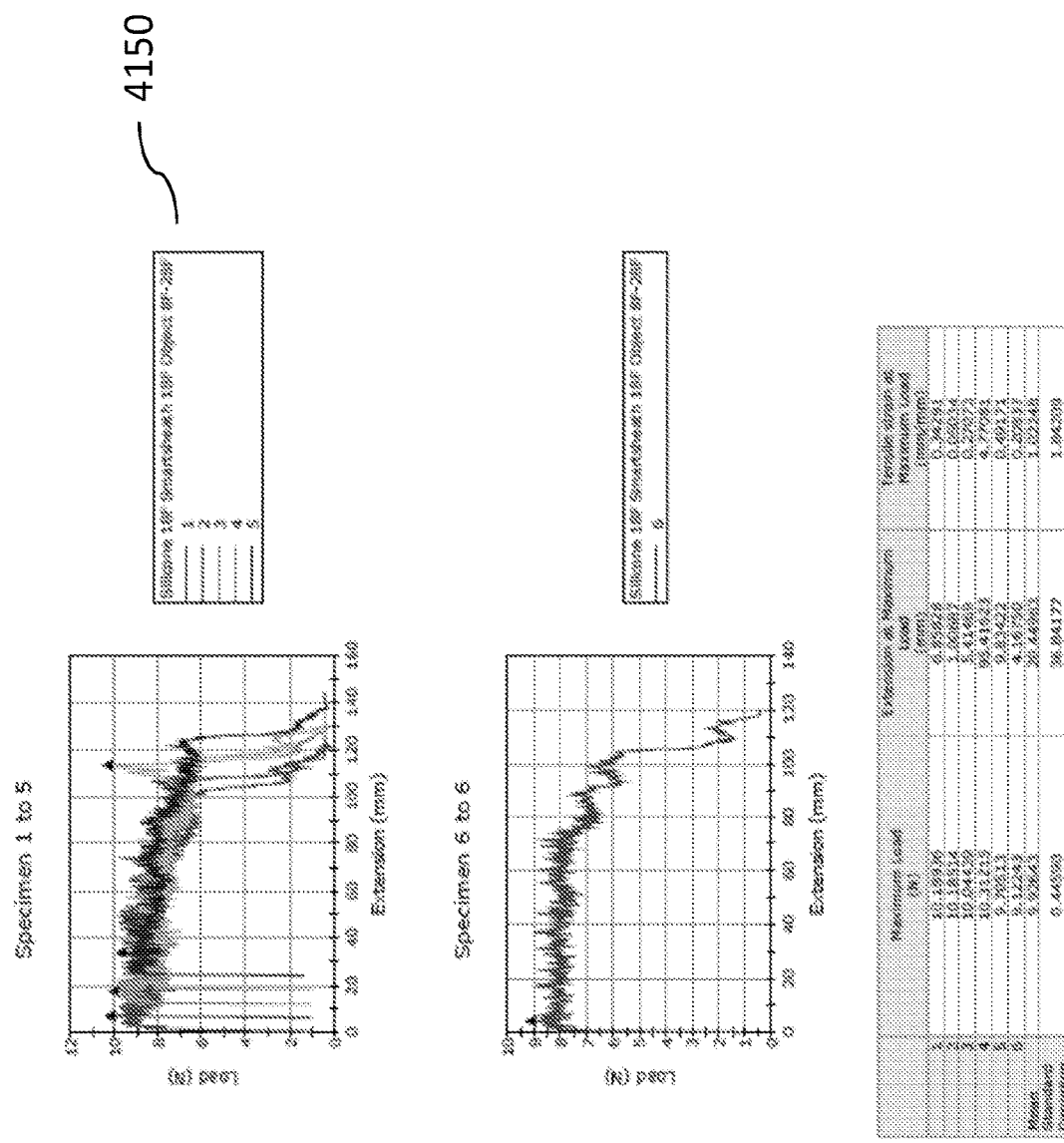
Figure 41C:
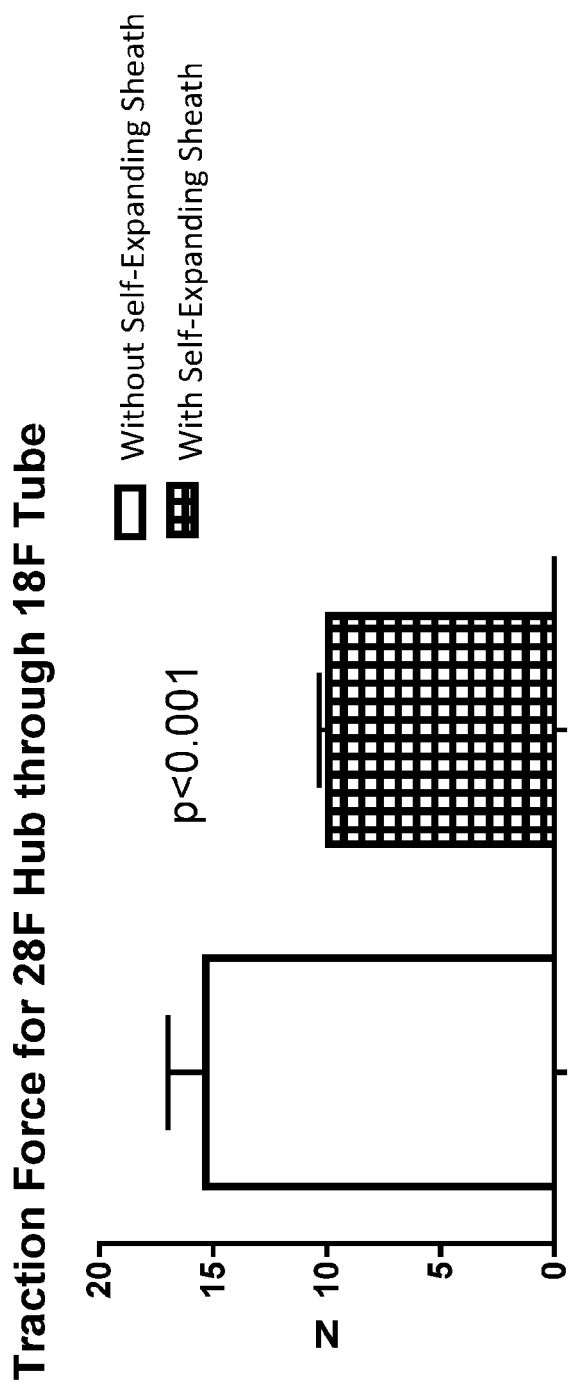

By comparison, FIG. 41*a* illustrates a current subject matter's self-expandable sheath (instead of the rectilinear sheath shown in FIG. 40*a*) 4102 being held in a traction bench 4120, where the self-expanding sheath 4102 and a 8 F dilator with a hub 4104 are being passed through a 28 F orifice. The measurements of forces required for traction of the hub through the self-expanding sheath 4102 within the smaller diameter tube are illustrated in FIG. 41*b* (plots and tables 4150). Clearly, the hub 4104 is larger than the luminal diameter of the 18 F sheath 4102 and the luminal diameter of the 18 F tube. In contrast to the conventional rectilinear sheath, the mean traction forces required to pull the 28 F hub through the 18 F self-expanding sheath within the 18 F silicone tube over a distance of approximately 120 mm approximately 9.93±0.45 N, which are significantly less than those required for the conventional sheath. FIG. 41*c* illustrates a plot 4160 showing comparison of forces required for using a conventional sheath (on the left side) and the current subject matter sheath (on the right side). The plot 4160 illustrates cumulated results for traction of six 28 F hubs through either a 18 F silicone tube (on the left side) and an 18 F self-expanding sheath positioned within a 18 F silicone tube (on the right side). Despite the additional material within the 18 F silicone tube due to the self-expanding sheath, the traction forces required are approximately 35% lower. This difference is statistically significant (p<0.001).

In some implementations, the current subject matter relates to an apparatus, such as a cannula, a sheath, and/or any other apparatus that can provide delivery of at least one of the following: a fluid, a gas, a powder, a device, an object, etc., and/or any combination thereof. The apparatus can include a first portion having an interior lumen, a narrow portion coupled to the first portion and having an interior lumen, an expandable portion having an interior lumen and being coupled to the narrow portion, the expandable portion being capable of having an expanded configuration and a collapsed configuration, and a tip being disposed at a distal end of the expandable portion. The interior lumens of the first portion, the narrow portion, and the expandable portion are communicatively coupled to allow passage of at least one of a fluid, a powder, a gas, an object, and a device.

In some implementations, the current subject matter can include one or more of the following optional features. A diameter of the narrow portion can be smaller than a diameter of the first portion. The first portion can be configured to be connectable to bypass tubing. In the collapsed configuration, the narrow portion and the expandable portion can have substantially equal diameters. In the collapsed configuration, the expandable portion can be inserted through an access orifice having a diameter substantially equal to or greater than the diameter of the expandable portion in the collapsed configuration, the access orifice being disposed on a target object configured to receive the device. Upon insertion of the expandable portion through the access orifice, the expandable portion can be advanced to a target location in the target object, wherein, at the target location, the expandable portion can be expanded into the expandable configuration.

In some implementations, the tip can include at least one orifice. The expandable portion can include at least one orifice as well. The orifice in the expandable portion can be positioned proximate the tip.

In some implementations, the apparatus can include a coating for covering at least a part of at least one of the following: the narrow portion, the expandable portion, and the tip. The coating can be a watertight coating.

In some implementations, the apparatus can permit flow of fluid through interior lumens of at least one of the following: the first portion, the narrow portion, the expandable portion, and the tip. The flow of fluid can be in at least one of the following directions: a single direction and multiple directions. The flow of fluid can be in at least one of the following directions: a retrograde direction and an antegrade direction. The flow of fluid in the retrograde direction can be substantially equal and/or unequal to the flow of fluid in the antegrade direction.

In some implementations, the apparatus can be a cannula (a bidirectional use cannula and/or unidirectional use cannula). The cannula can be at least one of the following: an arterial cannula, a venous cannula, and/or any combination thereof.

In some implementations, the expandable portion can include at least one diffuser for directing flow of fluid out of the apparatus. The expandable portion can include at least one deflector for deflecting flow of fluid out of the apparatus.

In some implementations, at least one of the narrow portion, the expandable portion, and the tip can be self-expanding.

In some implementations, at least one of the narrow portion, the expandable portion, and the tip can include a plurality of flexible filaments allowing the diameters of the at least one of the narrow portion, the expandable portion, and the tip to be varied using at least one mechanism. At least one mechanism can, upon actuation, serve to alter the configuration of at least one of the narrow portion, the expandable portion, and the tip between the collapsed configuration and the expanded configuration. The plurality of flexible filaments can include one or more materials that include at least one of the following: metal, shape-memory metal, alloy, plastic, textile fiber, synthetic fiber, natural fiber and any combination thereof. The plurality of flexible filaments can have a shape including at least one of the following: round, oval, flattened, triangular, rectangular and any combination thereof. The plurality of flexible filaments can include at least one of the following: elastic flexible filament, non-elastic flexible filament, textile fiber, flexible filaments that are braided together, flexible filaments that are knitted together, flexible filaments that are interwoven, flexible filaments that are interlaced, and/or any combination thereof. At least one flexible filament in the plurality of flexible filaments can be a covered flexible filament. At least one flexible filament in the plurality of flexible filaments can be an uncovered flexible filament. The mechanism can include at least one of the following: a mandrel, a bougie, a balloon, a pressurization mechanism, a retraction mechanism, an electric motor, a change in pressurization, a wrapping string, a balloon, a sheath, and/or any combination thereof.

In some implementations, the cannula can be insertable into at least one of the following: a hollow body, a solid body, and/or any combination thereof. The hollow body can include at least one of the following: a hollow organ in a patient, a vein, an artery, a urethra, a ureter, an intestine, an esophagus, a trachea, a bronchial tube, a pleural space, a peritoneum, and a vessel within a solid organ in the patient and/or another access device. The plurality of flexible filaments can form a plurality of openings in the cannula, the at least one of the hollow body and the solid body can be configured to at least partially cover at least one opening in the plurality of openings when the cannula is inserted into the at least one of the hollow body and the solid body.

In some implementations, the cannula can be a wall-less cannula. The cannula can be configured to be used in at least one of the following: a medical context, a non-medical context, percutaneous insertion, central cannulation, a tracheal tube, a chest tube, a drainage catheter, a heart surgery, hemofiltration, hemodialysis, a dialysis, and/or any combination thereof.

In some implementations, the tip can include at least one basket to stabilize placement of the tip at a target location. The basket can have a shape including at least one of the following: a bulb, a ball, a cylinder with round, an oval, an asymmetric shape, a triangular shape, a square shape, a pentagonal shape, a hexagonal shape, a heptagonal shape, an octagonal shape, a pyramid, a cone, a double cone, an inverted cone, an inverted double cone, a bell shape, a single layer shape, a dual layer shape, a multiple layer shape, single or multiple, uni- and/or multidirectional folds shape, plications, an inverted tulip-like structure, a tulip-like structure with a single or multiple small or large distal opening(s), a uniform shape, an asymmetric shape, and/or any combination thereof.

In some implementations, the expanded configuration can include at least one first expanded configuration and at least one second expanded configuration. A diameter of the expandable portion in the at least one second expanded configuration is greater than a diameter of the expandable portion in the at least one first configuration. In some implementation, this can allow for over-expansion of the cannula once the cannula is inserted beyond the access orifice. In some implementations, the expandable portion can include at least one portion having an elastic property to allow expansion of the expandable portion into at least one of the following: the at least one first expanded configuration and the at least one second expanded configuration. The expandable portion can also include at least one non-elastic section.

In some implementations, at least one of the expandable portion and the tip can include at least one portion containing at least one opening, wherein the at least one opening is configured for passing at least one of a fluid, a powder, a gas, an object, a device, and/or any combination thereof. That portion can be a non-elastic portion.

In some implementations, the expandable portion can be placed in the collapsed configuration using traction. The collapsed configuration can allow removal of the expandable portion from a target location.

In some implementations, the expandable portion can be placed in at least one of the collapsed configuration and the expanded configuration using at least one of the following mechanisms: a mandrel, a bougie, a balloon, a pressurization mechanism, a retraction mechanism, an electric motor, a change in pressurization, a wrapping string, a balloon, a sheath, and any combination thereof. The collapsed configuration can allow at least one of the placement and removal of at least the expandable portion from a target location.

In some implementations, the tip can include a basket having at least one expanded configuration and at least one collapsed configuration. The tip can be advanced to the target location in the collapsed configuration and expanded into the expandable configuration using the at least one of the mechanisms at the target location. Using at least one of the mechanisms, the tip can be placed into the collapsed configuration for removal from the target location. The basket can include at least one traction member for retaining the basket in the at least one expanded configuration. Release of the traction member can place the basket in the collapsed configuration.

In some implementations, the basket can include at least one locking mechanism (as discussed above) for retaining the basket in at least one expanded configuration, the locking mechanism is configured to stabilize the basket in the expanded configuration at the target location. The locking mechanism can include at least one of the following: an active locking mechanism, a passive locking mechanism, and any combination thereof. The locking mechanism can be configured to irreversibly retain the basket in the expanded configuration, thereby preventing the basket from being returned to the collapsed configuration. The locking mechanism can be configured to reversibly retain the basket in the expanded configuration, thereby allowing the basket to be returned into the collapsed configuration.

In some implementations, the apparatus can be a sheath. The sheath can be self-expandable. The sheath can be configured for delivery of at least one of the following: a fluid, a powder, a gas, an object, a device, and any combination thereof, to a target location. The sheath can include at least one of the following: at least one elastic section, at least one non-elastic section, at least one permanently deformable section, at least one temporarily deformable section, and/or any combination thereof. The sheath can include at least one lumen. The lumen can allow passage of at least one of the following: a fluid, a powder, a gas, an object, a device, and any combination thereof. The lumen in the sheath can include at least one of the following: a pressurized lumen, a depressurized lumen, a valve, a side arm, a split and any combination thereof.

In some implementations, the sheath can include a coating covering at least one portion of the sheath. The coating can be configured to change at least one property of the sheath including at least one of the following: a physical property, a chemical property, a mechanical property, a pharmaceutical property and any combination thereof.

In some implementations, the current subject matter relates to a cannula. The cannula can include a cannula housing having at least one lumen and at least one expandable portion. The expandable portion can have at least one expanded configuration and at least one collapsed configuration. A diameter of the lumen in the expanded configuration is greater than a diameter of the lumen in the collapsed configuration. In the expanded configuration, the lumen can allow passage of at least one of a fluid, a powder, a gas, an object, a device and any combination thereof. The expandable portion can be a self-expandable portion. The cannula housing can include a plurality of lumens. The cannula housing can include at least one orifice. The cannula housing can include at least one self-expanding tip.

In some implementations, the current subject matter relates to a sheath. The sheath can include a sheath housing having at least one lumen and at least one expandable portion. The expandable portion can have at least one expanded configuration and at least one collapsed configuration. A diameter of the lumen in the expanded configuration is greater than a diameter of the lumen in the collapsed configuration. In the expanded configuration, the lumen can allow passage of at least one of a fluid, a powder, a gas, an object, a device and any combination thereof. The expandable portion can be a self-expandable portion. The sheath housing can include a plurality of lumens. The sheath housing can include at least one orifice. The sheath housing can include at least one self-expanding tip.

Figure 42:
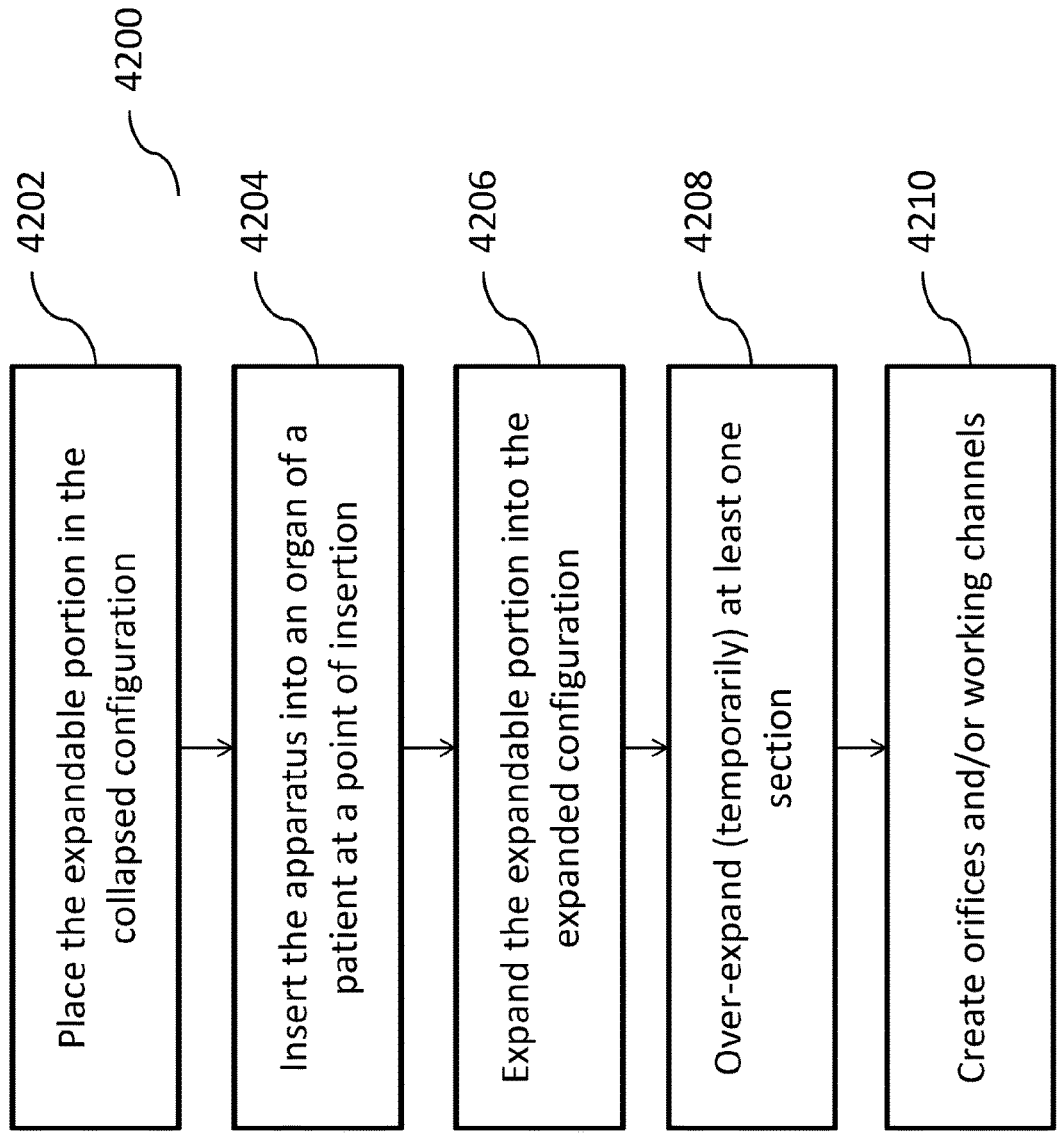
FIG. 42 illustrates an exemplary method, according to some implementations of the current subject matter.

FIG. 42 illustrates an exemplary method 4200 for using one or more of the above apparatuses (e.g., cannula, sheath, etc.), according to some implementations of the current subject matter. The method 4200 can include placing the expandable portion in the collapsed configuration (at 4202), inserting the apparatus into an organ of a patient at a point of insertion (at 4204), and expanding the expandable portion into the expanded configuration (at 4206), wherein in the expanded configuration, the expandable portion expands up to at least one of the following: a surface of an interior wall of the organ, the surrounding environment and the maximum diameter of the at least one lumen. In some implementations, at 4208, at least one section of the expandable portion can be optionally over-expanded, such as on temporary basis, where the section can include non-elastic section(s) and/or elastic section(s) of the expandable portion, as shown in FIGS. 34a-d, 37, and 38. This can allow passage of large objects, devices, streams, etc. and/or any combination thereof. Further, in some exemplary implementations, at 4210, orifice(s) and/or working channel(s) can be optionally created. This can be accomplished by local dilatation of the device structure, as shown, for example, in FIGS. 36a-c.

As used herein, the term "user" can refer to any entity including a person or a computer.

Although ordinal numbers such as first, second, and the like can, in some situations, relate to an order; as used in this document ordinal numbers do not necessarily imply an order. For example, ordinal numbers can be merely used to distinguish one item from another. For example, to distinguish a first event from a second event, but need not imply any chronological ordering or a fixed reference system (such that a first event in one paragraph of the description can be different from a first event in another paragraph of the description).

The foregoing description is intended to illustrate but not to limit the scope of the invention, which is defined by the scope of the appended claims. Other implementations are within the scope of the following claims.

The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and sub-combinations of the disclosed features and/or combinations and sub-combinations of several further features disclosed above. In addition, the logic flows depicted in the accompanying figures and/or described herein do not necessarily require the particular order shown, or sequential order, to achieve desirable results. Other implementations can be within the scope of the following claims.

What is claimed is:

1. An apparatus, comprising:
a first portion having a first interior lumen;
a narrow portion coupled to the first portion and having a second interior lumen, wherein a diameter of the narrow portion is smaller than a diameter of the first portion;
an expandable portion having a third interior lumen and being coupled to the narrow portion, the expandable portion being capable of having an expanded configuration and a collapsed configuration; and
a tip being disposed at a distal end of the expandable portion;
wherein the interior lumens of the first portion, the narrow portion, and the expandable portion are communicatively coupled to allow passage of at least one of a fluid, a powder, a gas, an object, and a device;
wherein the narrow portion, the expandable portion, and the tip are separately self-expanding;
wherein the tip includes at least one orifice.

2. The apparatus according to claim 1, wherein the first portion is configured to be connectable to bypass tubing.

3. The apparatus according to claim 1, wherein in the collapsed configuration, the narrow portion and the expandable portion have substantially equal diameters.

4. The apparatus according to claim 1, wherein in the collapsed configuration, the expandable portion is inserted through an access orifice having a diameter substantially equal to or greater than the diameter of the expandable portion in the collapsed configuration, the access orifice being disposed on a target object configured to receive the device.

5. The apparatus according to claim 4, wherein, upon insertion of the expandable portion through the access orifice, the expandable portion is advanced to a target location in the target object, wherein, at the target location, the expandable portion is expanded into the expandable configuration.

6. The apparatus according to claim 1, wherein the expandable portion includes at least one orifice.

7. The apparatus according to claim 6, wherein the orifice in the expandable portion is positioned proximate the tip.

8. The apparatus according to claim 1, further comprising a coating for covering at least a part of at least one of the following: the narrow portion, the expandable portion, and the tip.

9. The apparatus according to claim 8, wherein the coating is a watertight coating.

10. The apparatus according to claim 1, wherein the apparatus permits flow of fluid through interior lumens of at least one of the following: the first portion, the narrow portion, the expandable portion, and the tip.

11. The apparatus according to claim 10, wherein the flow of fluid is in at least one of the following directions: a single direction and multiple directions.

12. The apparatus according to claim 10, wherein the flow of fluid is in at least one of the following directions: a retrograde direction and an antegrade direction.

13. The apparatus according to claim 12, wherein the flow of fluid in the retrograde direction is substantially equal and/or unequal to the flow of fluid in the antegrade direction.

14. The apparatus according to claim 1, wherein the apparatus is a cannula.

15. The apparatus according to claim 14, wherein the cannula is at least one of the following: an arterial cannula and a venous cannula.

16. The apparatus according to claim 1, wherein the expandable portion includes at least one diffuser for directing flow of fluid out of the apparatus.

17. The apparatus according to claim 1, wherein the expandable portion includes at least one deflector for deflecting flow of fluid out of the apparatus.

18. The apparatus according to claim 1, wherein at least one of the narrow portion, the expandable portion, and the tip comprising a plurality of flexible filaments allowing the diameters of the at least one of the narrow portion, the expandable portion, and the tip to be varied using at least one mechanism.

19. The apparatus according to claim 18, further comprising at least one mechanism that, upon actuation, serves to alter the configuration of at least one of the narrow portion, the expandable portion, and the tip between the collapsed configuration and the expanded configuration.

20. The apparatus according to claim 18, wherein the plurality of flexible filaments comprises one or more materials that include at least one of the following: metal, shape-memory metal, alloy, plastic, textile fiber, synthetic fiber, natural fiber, and combinations thereof.

21. The apparatus according to claim 18, wherein the plurality of flexible filaments have a shape including at least one of the following: round, oval, flattened, triangular, rectangular and combinations thereof.

22. The apparatus according to claim 18, wherein the plurality of flexible filaments include at least one of the following: an elastic flexible filament, a non-elastic flexible filament, a textile fiber, flexible filaments that are braided together, flexible filaments that are knitted together, flexible filaments that are interwoven, flexible filaments that are interlaced, and any combination thereof.

23. The apparatus according to claim 18, wherein at least one flexible filament in the plurality of flexible filaments is a covered flexible filament.

24. The apparatus according to claim 18, wherein at least one flexible filament in the plurality of flexible filaments is an uncovered flexible filament.

25. The mechanism according to claim 18, wherein the at least one mechanism includes at least one of the following:

a mandrel, a bougie, a balloon, a pressurization mechanism, a retraction mechanism, an electric motor, a change in pressurization, a wrapping string, a balloon, a sheath and any combination thereof.

26. The apparatus according to claim 15, wherein the cannula is insertable into at least one of the following: a hollow body, a solid body, and any combination thereof.

27. The apparatus according to claim 26, wherein the hollow body includes at least one of the following: a hollow organ in a patient, a vein, an artery, a urethra, a ureter, an intestine, an esophagus, a trachea, a bronchial tube, a pleural space, a peritoneum, and a vessel within a solid organ in the patient and/or another access device.

28. The apparatus according to claim 26, wherein the plurality of flexible filaments form a plurality of openings in the cannula, the at least one of the hollow body and the solid body is configured to at least partially cover at least one opening in the plurality of openings when the cannula is inserted into the at least one of the hollow body and the solid body.

29. The apparatus according to claim 15, wherein the cannula is a wall-less cannula.

30. The apparatus according to claim 15, wherein the cannula is configured to be used in at least one of the following: a medical context, a non-medical context, percutaneous insertion, central cannulation, a tracheal tube, a chest tube, a drainage catheter, a heart surgery, hemofiltration, hemodialysis, and a dialysis.

31. The apparatus according to claim 1, wherein the tip includes at least one basket to stabilize placement of the tip at a target location.

32. The apparatus according to claim 31, wherein the at least one basket has a shape including at least one of the following: a bulb, a ball, a cylinder with round, an oval, an asymmetric shape, a triangular shape, a square shape, a pentagonal shape, a hexagonal shape, a heptagonal shape, an octagonal shape, a pyramid, a cone, a double cone, an inverted cone, an inverted double cone, a bell shape, a single layer shape, a dual layer shape, a multiple layer shape, single or multiple, uni- and/or multidirectional folds shape, plications, an inverted tulip-like structure, a tulip-like structure with a single or multiple small or large distal opening(s), a uniform shape, an asymmetric shape, and any combination thereof.

33. The apparatus according to claim 1, wherein the expanded configuration includes at least one first expanded configuration and at least one second expanded configuration, wherein a diameter of the expandable portion in the at least one second expanded configuration is greater than a diameter of the expandable portion in the at least one first configuration.

34. The apparatus according to claim 33, wherein the expandable portion includes at least one portion having an elastic property to allow expansion of the expandable portion into at least one of the following: the at least one first expanded configuration and the at least one second expanded configuration.

35. The apparatus according to claim 1, wherein at least one of the expandable portion and the tip include at least one portion containing at least one opening, wherein the at least one opening is configured for passing at least one of a fluid, a powder, a gas, an object, a device, and any combination thereof.

36. The apparatus according to claim 35, wherein the at least one portion is a non-elastic portion.

37. The apparatus according to claim 1, wherein the expandable portion is placed in the collapsed configuration using traction, wherein the collapsed configuration allowing removal of the expandable portion from a target location.

38. The apparatus according to claim 1, wherein the expandable portion is placed in at least one of the collapsed configuration and the expanded configuration using at least one of the following mechanisms: a mandrel, a bougie, a balloon, a pressurization mechanism, a retraction mechanism, an electric motor, a change in pressurization, a wrapping string, a balloon, a sheath, and any combination thereof;
wherein the collapsed configuration allowing at least one of the placement and removal of at least the expandable portion from a target location.

39. The apparatus according to claim 38, wherein the tip includes a basket having at least one expanded configuration and at least one collapsed configuration;
wherein the tip is advanced to the target location in the collapsed configuration and expanded into the expandable configuration using the at least one of the mechanisms at the target location;
wherein, using the at least one of the mechanisms, the tip is placed into the collapsed configuration for removal from the target location.

40. The apparatus according to claim 39, wherein the basket includes at least one traction member for retaining the basket in the at least one expanded configuration, wherein release of the at least one traction member places the basket in the collapsed configuration.

41. The apparatus according to claim 39, wherein the basket includes at least one locking mechanism for retaining the basket in at least one expanded configuration, the locking mechanism is configured to stabilize the basket in the at least one expanded configuration at the target location.

42. The apparatus according to claim 41, wherein the at least one locking mechanism includes at least one of the following: an active locking mechanism, a passive locking mechanism, and any combination thereof.

43. The apparatus according to claim 41, wherein the at least one locking mechanism is configured to irreversibly retain the basket in the at least one expanded configuration, thereby preventing the basket from being returned to the at least one collapsed configuration.

44. The apparatus according to claim 41, wherein the at least one locking mechanism is configured to reversibly retain the basket in the at least one expanded configuration, thereby allowing the basket to be returned into the at least one collapsed configuration.

45. The apparatus according to claim 1, wherein the apparatus is a sheath.

46. The apparatus according to claim 45, wherein the sheath is self-expandable.

47. The apparatus according to claim 45, wherein the sheath is configured for delivery of at least one of the following: a fluid, a powder, a gas, an object, a device, and any combination thereof, to a target location.

48. The apparatus according to claim 45, wherein the sheath includes at least one of the following: at least one elastic section, at least one non-elastic section, at least one permanently deformable section, at least one temporarily deformable section, and any combination thereof.

49. The apparatus according to claim 45, wherein the sheath includes at least one lumen, wherein the lumen allows passage of at least one of the following: a fluid, a powder, a gas, an object, a device, and any combination thereof.

50. The apparatus according to claim 49, wherein the at least one lumen in the sheath includes at least one of the following: a pressurized lumen, a depressurized lumen, a valve, a side arm, a split and any combination thereof.

51. The apparatus according to claim 45, further comprising a coating covering at least one portion of the sheath.

52. The apparatus according to claim 51, wherein the coating is configured to change at least one property of the sheath including at least one of the following: a physical property, a chemical property, a mechanical property, a pharmaceutical property and any combination thereof.

\* \* \* \* \*